(12) United States Patent
Nakagawa et al.

(10) Patent No.: US 9,989,849 B2
(45) Date of Patent: Jun. 5, 2018

(54) CHEMICALLY AMPLIFIED RESIST MATERIAL AND RESIST PATTERN-FORMING METHOD

(71) Applicant: JSR CORPORATION, Tokyo (JP)

(72) Inventors: Hisashi Nakagawa, Tokyo (JP);
Takehiko Naruoka, Tokyo (JP);
Tomoki Nagai, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days. days.

(21) Appl. No.: 15/347,113

(22) Filed: Nov. 9, 2016

(65) Prior Publication Data
US 2017/0131634 A1 May 11, 2017

(30) Foreign Application Priority Data

Nov. 9, 2015 (JP) .................................. 2015-219979
Nov. 7, 2016 (JP) .................................. 2016-217577

(51) Int. Cl.
*G03F 7/004* (2006.01)
*G03F 7/16* (2006.01)
(Continued)

(52) U.S. Cl.
CPC .......... *G03F 7/0046* (2013.01); *C07C 303/32* (2013.01); *C07C 309/07* (2013.01);
(Continued)

(58) Field of Classification Search
CPC ...... G03F 7/004; G03F 7/2002; G03F 7/0397; G03F 7/32; G03F 7/38; H01L 21/0274;
(Continued)

(56) References Cited

U.S. PATENT DOCUMENTS 4,037,021 A * 7/1977 Adams ................. C07D 317/26
428/441
8,124,326 B2 * 2/2012 Shirley ................. G03F 7/2022
430/322
(Continued)

FOREIGN PATENT DOCUMENTS

EP 0 622 682 A1 11/1994
JP H04-151156 A 5/1992
(Continued)

OTHER PUBLICATIONS

U.S. Appl. No. 15/239,136, filed Aug. 17, 2016, Nakagawa, et al.
(Continued)

*Primary Examiner* — Amanda C Walke
(74) *Attorney, Agent, or Firm* — Oblon, McClelland, Maier & Neustadt, L.L.P.

(57) ABSTRACT

A chemically amplified resist material comprises a polymer component that is capable of being made soluble or insoluble in a developer solution by an action of an acid, and a generative component that is capable of generating a radiation-sensitive sensitizer and an acid upon an exposure. The radiation-sensitive acid generating agent included in the generative component comprises a compound represented by the formula (B). $R^{B3}$ and $R^{B4}$ each independently represent a monovalent organic group, or taken together represent a cyclic structure together with the O—C—O. At least one of $R^{B3}$ and $R^{B4}$ comprises a halogen atom, a nitro group, a cyano group, a formyl group, a carbonyl group, a carboxy group, a sulfo group, a sulfonyl group or a combination thereof, or the cyclic structure having 4 to 30 ring atoms is a spiro cyclic structure, a fused cyclic structure or a bridged cyclic structure.

(Continued)

(B)

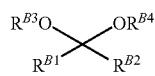

20 Claims, 2 Drawing Sheets

(51) Int. Cl.
*G03F 7/025* (2006.01)
*G03F 7/20* (2006.01)
*G03F 7/32* (2006.01)
*G03F 7/38* (2006.01)
*H01L 21/027* (2006.01)
*G03F 7/039* (2006.01)
*C08F 220/22* (2006.01)
*C07D 409/14* (2006.01)
*C07C 381/12* (2006.01)
*C08F 220/14* (2006.01)
*C07C 303/32* (2006.01)
*C08F 220/28* (2006.01)
*C07C 309/07* (2006.01)
*C08F 220/38* (2006.01)

(52) U.S. Cl.
CPC .......... *C07C 381/12* (2013.01); *C07D 409/14* (2013.01); *C08F 220/14* (2013.01); *C08F 220/22* (2013.01); *C08F 220/28* (2013.01); *C08F 220/38* (2013.01); *G03F 7/025* (2013.01); *G03F 7/0397* (2013.01); *G03F 7/168* (2013.01); *G03F 7/2002* (2013.01); *G03F 7/32* (2013.01); *G03F 7/38* (2013.01); *H01L 21/0274* (2013.01)

(58) Field of Classification Search
CPC ... C07C 381/12; C07C 303/32; C07C 309/07; C08F 220/14; C08F 220/28; C08F 220/22; C08F 220/38; C07D 409/14
USPC .... 430/270.1, 322, 325, 300, 331, 913, 330; 560/103, 1, 149, 9, 83; 526/243, 281
See application file for complete search history.

(56) References Cited

U.S. PATENT DOCUMENTS

| | | | | |
|---|---|---|---|---|
| 8,900,791 | B2* | 12/2014 | Tsuchimura | C07C 309/29 430/270.1 |
| 9,045,398 | B2* | 6/2015 | Suzuki | C07C 309/06 |
| 9,156,785 | B2* | 10/2015 | Aqad | C07C 63/72 |
| 9,244,347 | B2* | 1/2016 | Komuro | C07C 381/12 |
| 9,720,323 | B2* | 8/2017 | Kotake | G03F 7/0392 |
| 2006/0269879 | A1* | 11/2006 | Elian | G03F 7/203 430/394 |
| 2011/0151540 | A1* | 6/2011 | Taran | C12N 9/16 435/197 |
| 2013/0224659 | A1* | 8/2013 | Ohashi | C08F 220/18 430/285.1 |
| 2013/0344435 | A1* | 12/2013 | Utsumi | G03F 7/039 430/270.1 |
| 2014/0377706 | A1* | 12/2014 | Hatakeyama | G03F 7/32 430/296 |
| 2015/0086926 | A1* | 3/2015 | Ohashi | C07C 381/12 430/285.1 |
| 2015/0140493 | A1* | 5/2015 | Enomoto | C07D 317/22 430/322 |
| 2015/0241779 | A1* | 8/2015 | Enomoto | G03F 7/203 430/270.1 |
| 2016/0004160 | A1* | 1/2016 | Tagawa | G03F 7/38 430/296 |
| 2016/0187773 | A1* | 6/2016 | Enomoto | G03F 7/2022 430/270.1 |
| 2016/0194300 | A1* | 7/2016 | Enomoto | H01L 21/0271 216/87 |
| 2016/0195809 | A1* | 7/2016 | Ochiai | G03F 7/038 430/270.1 |
| 2016/0357103 | A1 | 12/2016 | Nagahara et al. | |

FOREIGN PATENT DOCUMENTS

| | | |
|---|---|---|
| JP | H04-162040 A | 6/1992 |
| JP | H05-005995 A | 1/1993 |
| JP | H05-197148 A | 8/1993 |
| JP | H06-194834 A | 7/1994 |
| JP | H08-146608 A | 6/1996 |
| JP | H10-083079 A | 3/1998 |
| JP | 2002-174894 A | 6/2002 |
| JP | 2006-227632 A | 8/2006 |
| JP | 2008-543033 A | 11/2008 |
| JP | 2009-134088 A | 6/2009 |
| JP | 2015-061831 A | 4/2015 |
| JP | 2015-078366 A | 4/2015 |
| JP | 2015-098471 A | 5/2015 |
| JP | 2015-134904 A | 7/2015 |
| JP | 2015-187252 A | 10/2015 |
| WO | WO 2005/069076 A1 | 7/2005 |
| WO | WO 2006/035790 A1 | 4/2006 |
| WO | WO 2006/125509 A2 | 11/2006 |
| WO | WO 2011/086389 A1 | 7/2011 |
| WO | WO 2014/129556 A1 | 8/2014 |
| WO | WO 2014/185065 A1 | 11/2014 |
| WO | WO 2014/208076 A1 | 12/2014 |
| WO | WO 2014/208102 A1 | 12/2014 |
| WO | WO 2014/208103 A1 | 12/2014 |
| WO | WO 2014/208104 A1 | 12/2014 |
| WO | WO 2015/019616 A1 | 2/2015 |
| WO | WO 2015/022779 A1 | 2/2015 |
| WO | WO 2015/049871 A1 | 4/2015 |
| WO | WO 2015/052914 A1 | 4/2015 |
| WO | WO 2015/125788 A1 | 8/2015 |
| WO | WO 2015/178464 A1 | 11/2015 |

OTHER PUBLICATIONS

U.S. Appl. No. 15/241,274, filed Aug. 19, 2016, Nakagawa, et al.
U.S. Appl. No. 15/241,315, filed Aug. 19, 2016, Nakagawa, et al.
U.S. Appl. No. 15/241,345, filed Aug. 19, 2016, Nakagawa, et al.
U.S. Appl. No. 15/259,160, filed Sep. 8, 2016, Nakagawa, et al.
U.S. Appl. No. 15/259,200, filed Sep. 8, 2016, Nakagawa, et al.
U.S. Appl. No. 15/347,033, filed Nov. 9, 2016, Nakagawa, et al.
S. Tagawa et al., "Super High Sensitivity Enhancement by Photo-Sensitized Chemically Amplified Resist (PS-CAR) Process", Journal of Photopolymer Science & Technology, 2013, vol. 26, No. 6, pp. 825-830.
S. Tagawa et al., "Super High Sensitivity Enhancement by Photo-Sensitized Chemically Amplified Resist (PS-CAR) Process", Journal of Photopolymer Science and Technology, vol. 26, No. 6 (2013), pp. 825-830.

* cited by examiner

CHEMICALLY AMPLIFIED RESIST MATERIAL AND RESIST PATTERN-FORMING METHOD

CROSS-REFERENCE TO RELATED APPLICATIONS

The present application claims priority to Japanese Patent Application No. 2015-219979, filed Nov. 9, 2015, and to Japanese Patent Application No. 2016-217577, filed Nov. 7, 2016. The contents of these applications are incorporated herein by reference in their entirety.

BACKGROUND OF THE INVENTION

Field of the Invention

The present invention relates to a chemically amplified resist material, and a resist pattern-forming method.

Discussion of the Background

Lithography in which EUV (extreme-ultraviolet) is utilized (hereinafter, may be referred to as "EUV lithography") attracts attention as one of element technologies for manufacture of the next-generation semiconductor devices. The EUV lithography is a pattern formation technology in which EUV having a wavelength of 13.5 nm is utilized as an exposure light. It is demonstrated that the EUV lithography enables an extremely fine pattern (line width: no greater than 20 nm, for example) to be formed in an exposure step of a manufacture process of the semiconductor devices.

However, since hitherto-developed EUV sources have low power, the exposure treatment tends to require a long time period. Thus, the EUV lithography has a disadvantage of being inferior in practical use. To overcome this disadvantage, a technique for increasing the sensitivity of a resist material which is a photosensitive resin has been developed (see Japanese Unexamined Patent Application, Publication No. 2002-174894).

SUMMARY OF THE INVENTION

According to one aspect of the present invention, a chemically amplified resist material comprises a polymer component that is capable of being made soluble or insoluble in a developer solution by an action of an acid, and a generative component that is capable of generating a radiation-sensitive sensitizer and an acid upon an exposure. The generative component comprises a radiation-sensitive acid-and-sensitizer generating agent and a radiation-sensitive sensitizer generating agent, the radiation-sensitive sensitizer generating agent and a radiation-sensitive acid generating agent, or all the radiation-sensitive acid-and-sensitizer generating agent, the radiation-sensitive sensitizer generating agent and the radiation-sensitive acid generating agent. The radiation-sensitive acid-and-sensitizer generating agent is capable of generating, upon an exposure to a first radioactive ray having a wavelength of no greater than 250 nm without an exposure to a second radioactive ray having a wavelength of greater than 250 nm, an acid and a radiation-sensitive sensitizer that absorbs only the second radioactive ray, but the radiation-sensitive acid-and-sensitizer generating agent substantially does not generate the acid and the radiation-sensitive sensitizer upon an exposure to the second radioactive ray without an exposure to the first radioactive ray. The radiation-sensitive sensitizer generating agent is capable of generating, upon the exposure to the first radioactive ray without the exposure to the second radioactive ray, the radiation-sensitive sensitizer that absorbs the second radioactive ray, but the radiation-sensitive sensitizer generating agent substantially does not generate the radiation-sensitive sensitizer upon the exposure to the second radioactive ray without the exposure to the first radioactive ray. The radiation-sensitive acid generating agent is capable of generating the acid upon the exposure to the first radioactive ray without the exposure to the second radioactive ray, but the radiation-sensitive acid generating agent substantially does not generate the acid upon the exposure to the second radioactive ray without the exposure to the first radioactive ray. The radiation-sensitive sensitizer generating agent comprises a compound represented by formula (B).

In the formula (B), $R^{B1}$ and $R^{B2}$ each independently represent a hydrogen atom, a halogen atom, an amino group or a monovalent organic group that comprises a carbon atom which bonds to the carbon atom to which $R^{B3}O$ and $R^{B4}O$ bond, or $R^{B1}$ and $R^{B2}$ taken together represent a cyclic structure having 3 to 30 ring atoms together with the carbon atom to which $R^{B1}$ and $R^{B2}$ bond; and $R^{B3}$ and $R^{B4}$ each independently represent a monovalent organic group having 1 to 20 carbon atoms, or taken together represent a cyclic structure having 4 to 30 ring atoms together with O—C—O to which $R^{B3}$ and $R^{B4}$ bond, wherein at least one of $R^{B3}$ and $R^{B4}$ comprises a halogen atom, a nitro group, a cyano group, a formyl group, a carbonyl group, a carboxy group, a sulfo group, a sulfonyl group or a combination thereof, or the cyclic structure having 4 to 30 ring atoms is a spiro cyclic structure, a fused cyclic structure or a bridged cyclic structure.

According to another aspect of the present invention, a resist pattern-forming method comprises applying the chemically amplified resist material on at least one face of a substrate to form a resist film. The resist film is patternwise exposed to a radioactive ray having a wavelength of no greater than 250 nm. The resist film patternwise exposed is floodwise exposed to a radioactive ray having a wavelength of greater than 250 nm. The resist film floodwise exposed is baked. The resist material film baked is developed with a developer solution.

DESCRIPTION OF THE EMBODIMENTS

Figure 1:
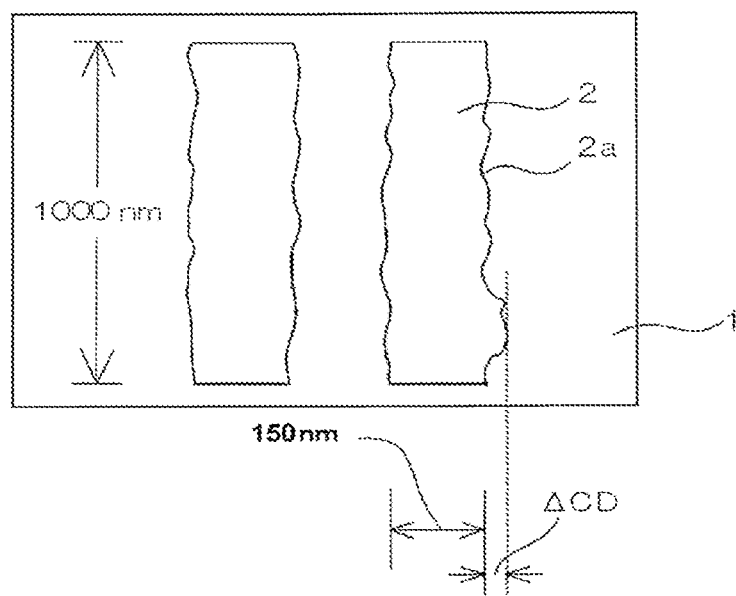
FIG. 1 shows a schematic plan view illustrating the nanoedge roughness of a pattern.

According to an embodiment of the invention made for solving the aforementioned problems, a chemically amplified resist material contains: (1) a polymer component that is capable of being made soluble or insoluble in a developer solution by an action of an acid; and (2) a component (may be also referred to as "generative component") that is capable of generating a radiation-sensitive sensitizer and an acid upon an exposure, wherein the generative component (2) contains the following components (a) and (b), the following components (b) and (c), or all of the following components (a) to (c):

(a) a radiation-sensitive acid-and-sensitizer generating agent that is capable of generating, upon an exposure to a first radioactive ray having a wavelength of no greater than 250 nm without an exposure to a second radioactive ray having a wavelength of greater than 250 nm, an acid and a radiation-sensitive sensitizer that absorbs only the second radioactive ray, but the radiation-sensitive acid-and-sensitizer generating agent substantially does not generate the acid and the radiation-sensitive sensitizer upon an exposure to the second radioactive ray without an exposure to the first radioactive ray;

(b) a radiation-sensitive sensitizer generating agent that is capable of generating, upon the exposure to the first radioactive ray without the exposure to the second radioactive ray, the radiation-sensitive sensitizer that absorbs the second radioactive ray, but the radiation-sensitive sensitizer generating agent substantially does not generate the radiation-sensitive sensitizer upon the exposure to the second radioactive ray without the exposure to the first radioactive ray; and (c) a radiation-sensitive acid generating agent that is capable of generating an acid upon the exposure to the first radioactive ray without the exposure to the second radioactive ray, but the radiation-sensitive acid generating agent substantially does not generate the acid upon the exposure to the second radioactive ray without the exposure to the first radioactive ray, wherein the component (b) includes a compound represented by the following formula (B) (hereinafter, may be also referred to as "(B) compound" or "compound (B)"):

(B)

wherein, in the above formula (B), $R^{B1}$ and $R^{B2}$ each independently represent a hydrogen atom, a halogen atom, an amino group or a monovalent organic group that bonds to the carbon atom to which $R^{B3}O$ and $R^{B4}O$ bond via a carbon atom, or $R^{B1}$ and $R^{B2}$ taken together represent a cyclic structure having 3 to 30 ring atoms together with the carbon atom to which $R^{B1}$ and $R^{B2}$ bond; and $R^{B3}$ and $R^{B4}$ each independently represent a monovalent organic group having 1 to 20 carbon atoms, or taken together represent a cyclic structure having 4 to 30 ring atoms together with O—C—O to which $R^{B3}$ and $R^{B4}$ bond, wherein at least one of $R^{B3}$ and $R^{B4}$ includes a halogen atom, a nitro group, a cyano group, a formyl group, a carbonyl group, a carboxy group, a sulfo group, a sulfonyl group or a combination thereof, or the cyclic structure having 4 to 30 ring atoms is a spiro cyclic structure, a fused cyclic structure or a bridged cyclic structure.

According to another embodiment of the invention made for solving the aforementioned problems, a resist pattern-forming method includes: an application step of applying the chemically amplified resist material according to the above embodiment of the present invention on at least one face of a substrate; a patternwise exposure step of patternwise exposing to a radioactive ray having a wavelength of no greater than 250 nm (hereinafter, may be also referred to as "first radioactive ray"), the resist film obtained by the applying; a floodwise exposure step of floodwise exposing to a radioactive ray having a wavelength of greater than 250 nm (hereinafter, may be also referred to as "second radioactive ray"), the resist film obtained after the patternwise exposure step; a baking step of baking the resist film obtained after the floodwise exposure step; and a development step of developing with a developer solution, the resist film obtained after the baking step.

The phrases "substantially does not generate the acid and the radiation-sensitive sensitizer upon an/the exposure to (or, irradiation with) the second radioactive ray without an/the exposure to (or, irradiation with) the first radioactive ray", "substantially does not generate the radiation-sensitive sensitizer upon an/the exposure to (or, irradiation with) the second radioactive ray without an/the exposure to (or, irradiation with) the first radioactive ray" and "substantially does not generate the acid upon an/the exposure to (or, irradiation with) the second radioactive ray without an/the exposure to (or, irradiation with) the first radioactive ray" as referred to mean that the acid and/or the radiation-sensitive sensitizer is/are not generated through the exposure to (or, irradiation with) the second radioactive ray, or that even in the case where the acid and/or the radiation-sensitive sensitizer is/are generated through the exposure to (or, irradiation with) the second radioactive ray, the amount of the acid and/or the radiation-sensitive sensitizer generated in the patternwise unexposed regions to the second radioactive ray is so small that the difference in the concentration of the acid and/or the radiation-sensitive sensitizer between the light-exposed regions and the light-unexposed regions in the patternwise exposure can be maintained at a level to permit the pattern formation, and consequently the amount of the acid and/or the radiation-sensitive sensitizer thus generated is so small that either the patternwise exposed region or the patternwise unexposed regions alone can be dissolved in the developer solution in the development step. The "organic group" as referred to means a group that includes at least one carbon atom. The "ring atom" as referred to means the number of atoms constituting a ring of a cyclic structure, and in the case of polycyclic structures, the "ring atom" means the number of atoms constituting the polycycle. The "polymer" as referred to falls under a concept that involves oligomers.

According to the chemically amplified resist material and the resist pattern-forming method of the embodiments of the present invention, in a case where a radioactive ray having a wavelength of no greater than 250 nm such as EUV, an electron beam, a KrF excimer laser beam and an ArF excimer laser beam is used as patterning exposure light, both sensitivity and lithography performances such as nanoedge roughness can be attained at a high level.

Hereinafter, embodiments of the present invention will be described in detail. It is to be noted that the present invention is not limited to the following embodiments.

Chemically Amplified Resist Material

The chemically amplified resist material according to an embodiment of the present invention contains: (1) a polymer component that is capable of being made soluble or insoluble in a developer solution by an action of an acid; and (2) a generative component that is capable of generating a radiation-sensitive sensitizer and an acid upon an exposure, wherein the generative component (2) contains the following components (a) and (b), the following components (b) and (c), or all of the following components (a) to (c):

(a) a radiation-sensitive acid-and-sensitizer generating agent that is capable of generating, upon the irradiation with a first radioactive ray having a wavelength of no greater than 250 nm without the irradiation with a second radioactive ray having a wavelength of greater than 250 nm, an acid and a radiation-sensitive sensitizer that absorbs only the second radioactive ray, but the radiation-sensitive acid-and-sensitizer generating agent substantially does not generate the acid and the radiation-sensitive sensitizer upon the irradiation with the second radioactive ray without the irradiation with the first radioactive ray;

(b) a radiation-sensitive sensitizer generating agent that is capable of generating, upon the irradiation with the first radioactive ray without the irradiation with the second radioactive ray, the radiation-sensitive sensitizer that absorbs the second radioactive ray, but the radiation-sensitive sensitizer generating agent substantially does not generate the radiation-sensitive sensitizer upon the irradiation with the second radioactive ray without the irradiation with the first radioactive ray; and (c) a radiation-sensitive acid generating agent that is capable of generating the acid upon the irradiation with the first radioactive ray without the irradiation with the second radioactive ray, but the radiation-sensitive acid generating agent substantially does not generate the acid upon the irradiation with the second radioactive ray without the irradiation with the first radioactive ray.

Moreover, the chemically amplified resist material may typically contain a solvent in addition to the polymer component (1) and the generative component (2), and may further contain an acid diffusion control agent, radical trapping agent, crosslinking agent, other additive, and the like.

Herein, the generative component (2) may be incorporated into a part of a polymer or low-molecular weight compound constituting the polymer component (1), and may be a component that is different from the polymer component (1). In this case, a part of the generative component (2) may be a component that is different from the polymer component (1), or the entirety of the generative component (2) may be a component that is different from the polymer component (1).

(1) Polymer Component

The polymer component (1) is a component that is capable of being made soluble or insoluble in a developer solution by an action of an acid. The polymer component (1) contains, for example, a first polymer (hereinafter, may be also referred to as "(A) polymer" or "polymer (A)") having a structural unit (hereinafter, may be also referred to as "structural unit (I)") that includes a group that is capable of generating a polar group by an action of an acid through dissociation of an acid-labile group (hereinafter, may be also referred to as "polar group protected by an acid-labile group"), as well as a calixarene (hereinafter, may be also referred to as "(C) polymer" or "polymer (C)") having the structural unit (I), and the like. Also, the polymer component (1) may contain a component other than the component that is capable of being made soluble or insoluble in a developer solution by an action of an acid as long as the polymer (A) or the polymer (C) is included. In specific examples, the polymer component (1) may further contain a second polymer (hereinafter, may be also referred to as "(B) polymer" or "polymer (B)") not having the structural unit (I). The term "calixarene" as referred to means a cyclic oligomer derived from a plurality of aromatic rings to which a hydroxy group bonds, or a plurality of heteroaromatic rings to which a hydroxy group bonds, through linking to be cyclic via a hydrocarbon group.

The polymer (A) and the polymer (B) may further have a structural unit that includes: a fluorine atom (hereinafter, may be also referred to as "structural unit (II)"); and a structural unit (III) that includes a phenolic hydroxyl group and a structural unit (IV) that includes a lactone structure, a cyclic carbonate structure, a sultone structure or a combination thereof, and may further have other structural unit than the structural units (I) to (IV).

(A) Polymer and (B) Polymer

The polymer (A) has the structural unit (I). Also, the polymer (A) may further have structural units (II) to (IV), as well as other structural unit. The polymer (B) is different from the polymer (A). The polymer (B) preferably has the structural unit (II), and may have the structural unit (III) and the structural unit (IV), as well as other structural unit.

Structural Unit (I)

The structural unit (I) includes a polar group protected by an acid-labile group. When the polymer (A) has the structural unit (I), the sensitivity and lithography performances of the chemically amplified resist material can be further improved. The structural unit (I) is exemplified by a structural unit represented by the following formula (a-1) (hereinafter, may be also referred to as "structural unit (I-1)"), a structural unit represented by the following formula (a-2) (hereinafter, may be also referred to as "structural unit (I-2)"), and the like. In the following formulae (a-1) and (a-2), the group represented by $-CR^{A2}R^{A3}R^{A4}$ or $-CR^{A6}R^{A7}R^{A8}$ corresponds to the acid-labile group.

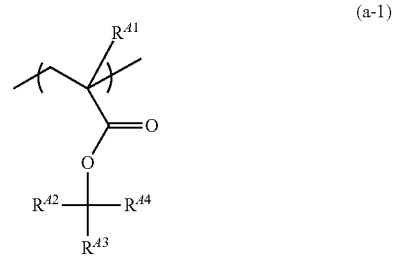

(a-1)

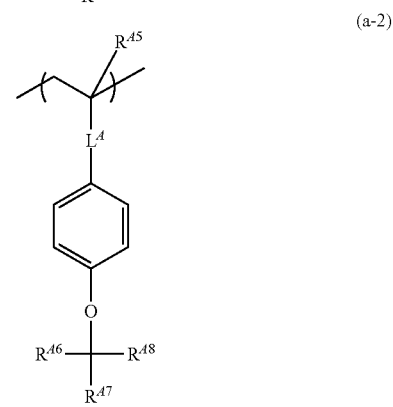

(a-2)

In the above formula (a-1), $R^{A1}$ represents a hydrogen atom, a fluorine atom, a methyl group or a trifluoromethyl group; $R^{A2}$ represents a monovalent hydrocarbon group having 1 to 20 carbon atoms; $R^{A3}$ and $R^{A4}$ each independently represent a monovalent chain hydrocarbon group having 1 to 20 carbon atoms or a monovalent alicyclic hydrocarbon group having 3 to 20 carbon atoms, or these groups taken together represent an alicyclic structure having 3 to 20 ring atoms together with the carbon atom to which these groups bond.

In the above formula (a-2), $R^{A5}$ represents a hydrogen atom, a fluorine atom, a methyl group or a trifluoromethyl group; $R^{A6}$ represents a hydrogen atom, a monovalent hydrocarbon group having 1 to 20 carbon atoms or a monovalent oxyhydrocarbon group having 1 to 20 carbon atoms; $R^{47}$ and $R^{48}$ each independently represent a monovalent hydrocarbon group having 1 to 20 carbon atoms or a monovalent oxyhydrocarbon group having 1 to 20 carbon atoms; and $L^A$ represents a single bond, —O—, —COO— or —CONH—.

The monovalent hydrocarbon group having 1 to 20 carbon atoms which may be represented by $R^{42}$, $R^{46}$, $R^{47}$ or $R^{48}$ is exemplified by a chain hydrocarbon group having 1 to 30 carbon atoms, an alicyclic hydrocarbon group having 3 to 30 carbon atoms, an aromatic hydrocarbon group having 6 to 30 carbon atoms, and the like.

Examples of the monovalent chain hydrocarbon group having 1 to 30 carbon atoms include:

alkyl groups such as a methyl group, an ethyl group, a n-propyl group and an i-propyl group;

alkenyl groups such as an ethenyl group, a propenyl group and a butenyl group;

alkynyl groups such as an ethynyl group, a propynyl group and a butynyl group; and the like.

Examples of the monovalent alicyclic hydrocarbon group having 3 to carbon atoms include:

saturated monocyclic hydrocarbon groups such as a cyclopropyl group, a cyclobutyl group, a cyclopentyl group, a cyclohexyl group, a cyclopentyl group, a cyclooctyl group, a cyclodecyl group and a cyclododecyl group; unsaturated monocyclic hydrocarbon groups such as a cyclopropenyl group, a cyclobutenyl group, a cyclopentenyl group, a cyclohexenyl group, a cyclooctenyl group and a cyclodecenyl group;

saturated polycyclic hydrocarbon groups such as a bicyclo[2.2.1]heptanyl group, a bicyclo[2.2.2]octanyl group and a tricyclo[3.3.1.1$^{3,7}$]decanyl group;

unsaturated polycyclic hydrocarbon groups such as a bicyclo[2.2.1]heptenyl group and a bicyclo[2.2.2]octenyl group; and the like.

Examples of the monovalent aromatic hydrocarbon group having 6 to 30 carbon atoms include:

aryl groups such as a phenyl group, a tolyl group, a xylyl group, a mesityl group, a naphthyl group, a methylnaphthyl group, an anthryl group and a methylanthryl group;

aralkyl groups such as a benzyl group, a phenethyl group, a naphthylmethyl group and an anthrylmethyl group; and the like.

$R^{42}$ represents preferably a chain hydrocarbon group or a cycloalkyl group, more preferably an alkyl group or a cycloalkyl group, and still more preferably a methyl group, an ethyl group, a propyl group, a cyclopentyl group, a cyclohexyl group, a cyclooctyl group or an adamantyl group.

Examples of the monovalent chain hydrocarbon group having 1 to 20 carbon atoms and monovalent alicyclic hydrocarbon group having 3 to 20 carbon atoms which may be represented by $R^{43}$ or $R^{44}$ include groups similar to those exemplified in connection with $R^{42}$, $R^{46}$, $R^{47}$ and $R^{48}$, and the like.

Examples of the alicyclic structure having 3 to 20 ring atoms which may be taken together represented by the groups $R^{43}$ and $R^{44}$ together with the carbon atom to which $R^{43}$ and $R^{44}$ bond include:

monocyclic cycloalkane structures such as a cyclopropane structure, a cyclobutane structure, a cyclopentane structure, a cyclopentene structure, a cyclopentadiene structure, a cyclohexane structure, a cyclooctane structure and a cyclodecane structure;

polycyclic cycloalkane structures such as a norbornane structure, an adamantane structure, a tricyclodecane structure and a tetracyclododecane structure; and the like.

$R^{43}$ and $R^{44}$ represent preferably an alkyl group, a monocyclic cycloalkane structure taken together represented by $R^{43}$ and $R^{44}$ together with the carbon atom to which $R^{43}$ and $R^{44}$ bond, a norbornane structure or an adamantane structure, and more preferably a methyl group, an ethyl group, a cyclopentane structure, a cyclohexane structure or an adamantane structure.

Examples of the monovalent oxyhydrocarbon group having 1 to 20 carbon atoms which may be represented by $R^{46}$, $R^{47}$ or $R^{48}$ include groups obtained by incorporating an oxygen atom between two adjacent carbon atoms of the monovalent hydrocarbon group having 1 to 20 carbon atoms exemplified in connection with $R^{42}$, $R^{46}$, $R^{47}$ and $R^{48}$, and the like.

$R^{46}$, $R^{47}$ and $R^{48}$ preferably represent a chain hydrocarbon group, and an oxygen atom-containing alicyclic hydrocarbon group.

$L^A$ represents preferably a single bond or —COO—, and more preferably a single bond.

In light of the copolymerizability of a monomer that gives the structural unit (I), $R^{41}$ represents preferably a hydrogen atom or a methyl group, and more preferably a methyl group.

In light of the copolymerizability of a monomer that gives the structural unit (I), $R^{45}$ represents preferably a hydrogen atom or a methyl group, and more preferably a hydrogen atom.

Examples of the structural unit (I-1) include structural units represented by the following formulae (a-1-a) to (a-1-d) (hereinafter, may be also referred to as "structural units (I-1-a) to (I-1-d)"), and the like. Moreover, examples of the structural unit (I-2) include a structural unit represented by the following formula (a-2-a) (hereinafter, may be also referred to as "structural unit (I-2-a)"), and the like.

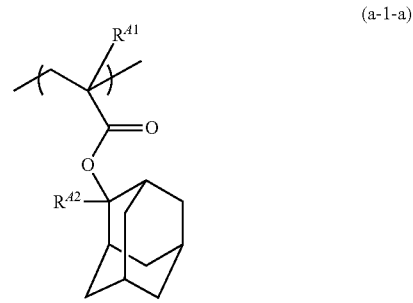

(a-1-a)

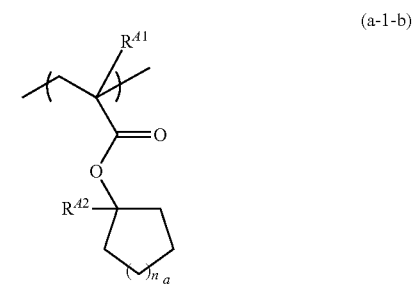

(a-1-b)

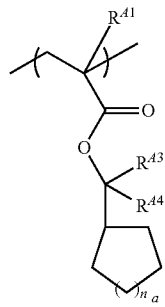

(a-1-c)

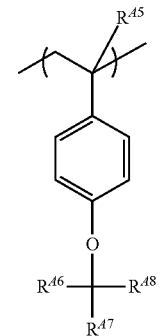

(a-1-d)

(a-2-a)

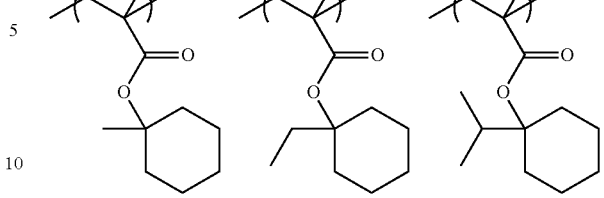

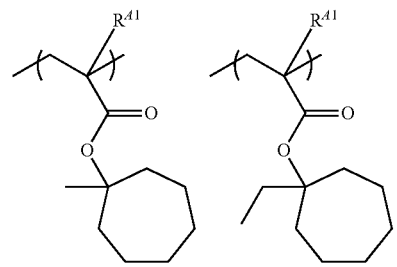

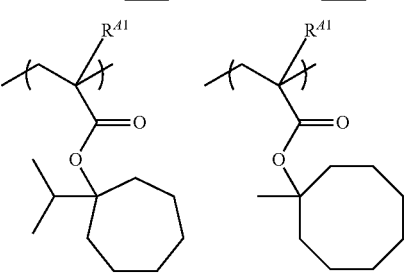

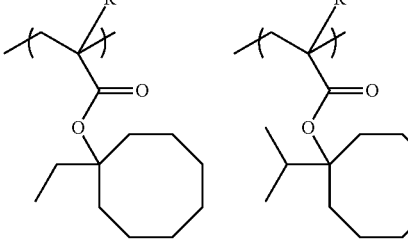

In the above formulae (a-1-a) to (a-1-d), $R^{A1}$ to $R^{A4}$ are as defined in the above formula (a-1); and $n_a$ is an integer of 1 to 4. In the above formula (a-2-a), $R^{A5}$ to $R^{A8}$ are as defined in the above formula (a-2).

In the above formulae (a-1-b) and (a-1-d), $n_a$ is preferably 1, 2 or 4, and more preferably 1.

Examples of the structural units (I-1-a) to (I-1-d) include structural units represented by the following formulae, and the like.

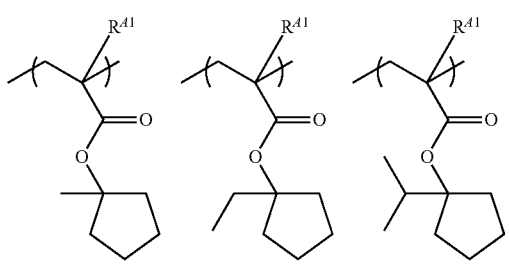

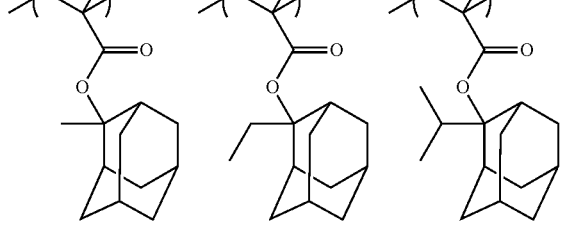

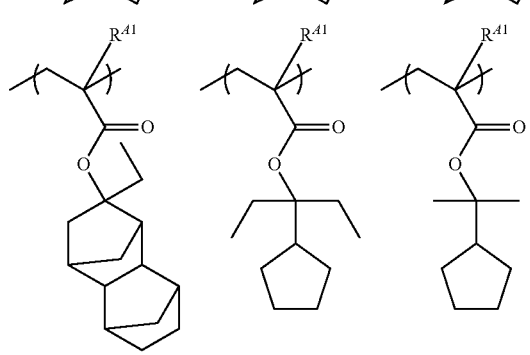

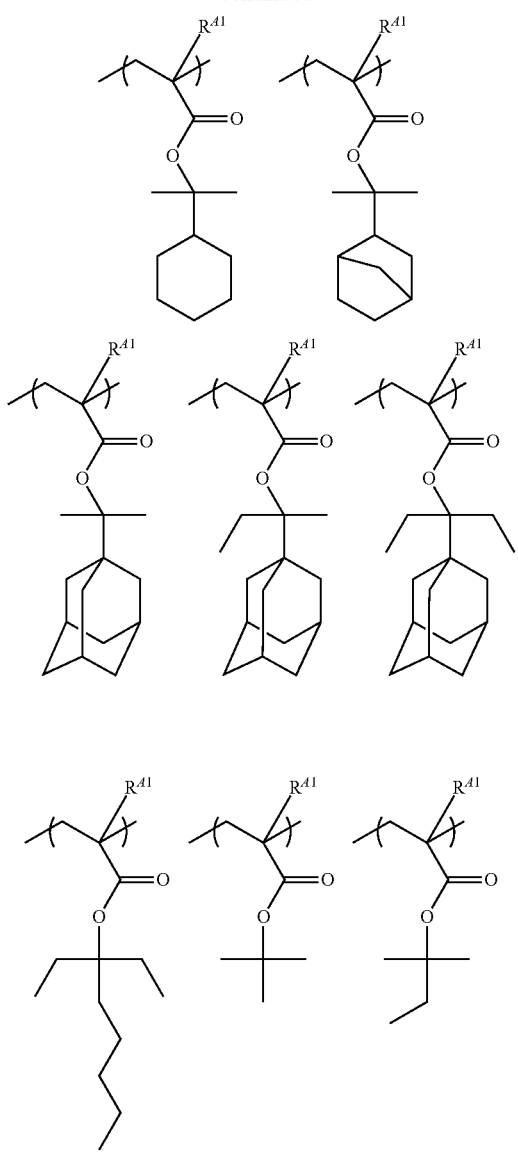

In the above formulae, $R^{A1}$ is as defined in the above formula (a-1).

Examples of the structural unit (I-2) include structural units represented by the following formulae, and the like.

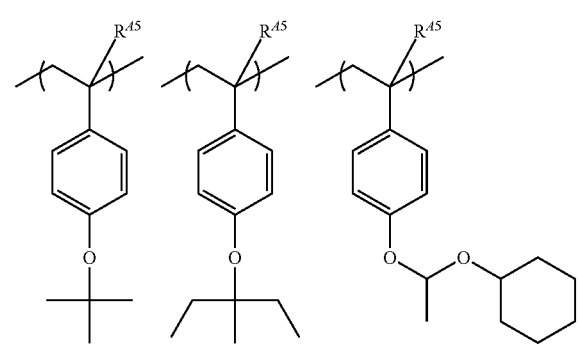

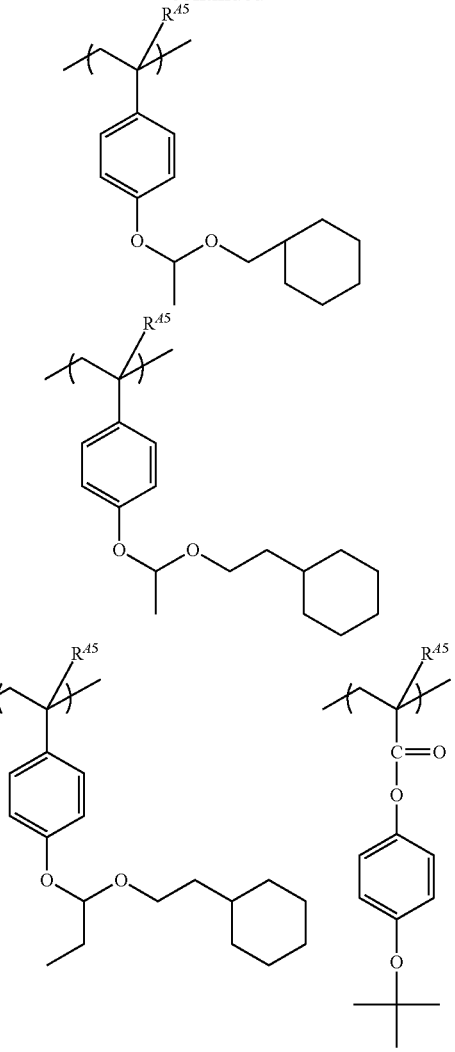

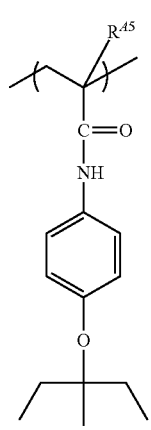

In the above formulae, $R^{A5}$ is as defined in the above formula (a-2).

As the structural unit (I), the structural units (I-1-a) to (a-2-a) are preferred, and a structural unit derived from 2-methyl-2-adamantyl (meth)acrylate, a structural unit derived from 2-i-propyl-2-adamantyl (meth)acrylate, a structural unit derived from 1-methyl-1-cyclopentyl (meth)acrylate, a structural unit derived from 1-ethyl-1-cyclohexyl (meth)acrylate, a structural unit derived from 1-i-propyl-1-cyclopentyl (meth)acrylate, a structural unit derived from 2-cyclohexylpropan-2-yl (meth)acrylate, and a structural unit derived from 2-(adamantan-1-yl)propan-2-yl (meth)acrylate are more preferred.

The lower limit of the proportion of the structural unit (I) with respect to the total structural units constituting the polymer (A) is preferably 10 mol %, more preferably 20 mol %, still more preferably 30 mol %, and particularly preferably 45 mol %. On the other hand, the upper limit of the proportion of the structural unit (III) with respect to the total structural units constituting the polymer (A) or the polymer (F) is preferably 80 mol %, more preferably 70 mol %, still more preferably 65 mol %, and particularly preferably 60 mol %. When the proportion of the structural unit (III) falls within the above range, a contrast in terms of dissolution in the developer solution between the patternwise exposed regions and the patternwise unexposed regions of the resist film formed from the chemically amplified resist material can be sufficiently established, and consequently the resolution and the like may be improved.

Structural Unit (II)

The structural unit (II) includes a fluorine atom, but those corresponding to the structural unit (I) are excluded. The structural unit (II) typically does not include a salt structure. Examples of the structural unit (II) include structural units represented by the following formulae (f-1) to (f-4), and the like.

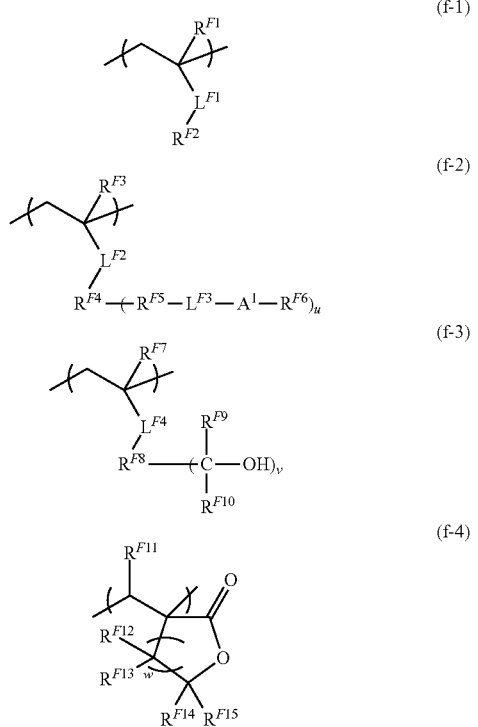

In the above formula (f-1), $R^{F1}$ represents a hydrogen atom, a fluorine atom, a methyl group or a trifluoromethyl group; $L^{F1}$ represents a single bond, an oxygen atom, a sulfur atom, —CO—O—, —SO$_2$—O—NH—, —CO—NH— or —O—CO—NH—; and $R^{F2}$ represents a monovalent fluorinated hydrocarbon group having 1 to 20 carbon atoms.

In the above formula (f-2), $R^{F3}$ represents a hydrogen atom, a fluorine atom, a methyl group or a trifluoromethyl group; $L^{F2}$ represents a single bond, an oxygen atom, a sulfur atom, —CO—O—, —SO$_2$—O—NH—, —CO—NH— or —O—CO—NH—; $R^{F4}$ represents a single bond, a hydrocarbon group having 1 to 20 carbon atoms and having a valency of (u+1), or a structure obtained by incorporating an oxygen atom, a sulfur atom, —NR$^{FF1}$—, a carbonyl group, —CO—O— or —CO—NH— into the end on the $R^{F5}$ side of the hydrocarbon group having 1 to 20 carbon atoms and having a valency of (u+1), wherein $R^{FF1}$ represents a hydrogen atom or a monovalent hydrocarbon group having 1 to 10 carbon atoms; $R^{F5}$ represents a single bond or a divalent organic group having 1 to 20 carbon atoms; $L^{F3}$ represents a single bond or a divalent fluorinated chain hydrocarbon group having 1 to 20 carbon atoms; $A^1$ represents an oxygen atom, —NR$^{FF2}$—, —CO—O—* or —SO$_2$—O—*, wherein $R^{FF2}$ represents a hydrogen atom or a monovalent hydrocarbon group having 1 to 10 carbon atoms, and * denotes a binding site to $R^{F6}$; $R^{F6}$ represents a hydrogen atom or a monovalent organic group having 1 to 30 carbon atoms; and u is an integer of 1 to 3, wherein in a case where u is 1, $R^{F4}$ may represent a single bond, and in a case where u is 2 or 3, a plurality of $R^{F5}$s may be identical or different, a plurality of $L^{F3}$s may be identical or different, a plurality of $A_1$s may be identical or different, and a plurality of $R^{F6}$s may be identical or different.

In the above formula (f-3), $R^{F7}$ represents a hydrogen atom, a fluorine atom, a methyl group, a trifluoromethyl group or a monovalent carbonyloxy hydrocarbon group having 2 to 20 carbon atoms; $L^{F4}$ represents a single bond, an oxygen atom, a sulfur atom, —CO—O—, —SO$_2$—O—NH—, —CO—NH— or —O—CO—NH—; $R^{F8}$ represents a single bond or a divalent organic group having 1 to 20 carbon atoms; $R^{F9}$ and $R^{F10}$ each independently represent an alkyl group having 1 to 10 carbon atoms or a fluorinated alkyl group having 1 to 10 carbon atoms, wherein either $R^{F9}$ or $R^{F10}$ represents the fluorinated alkyl group; and v is an integer of 1 to 3, wherein in a case where v is 2 or 3, a plurality of $R^{F9}$s may be identical or different, and a plurality of $R^{F10}$s may be identical or different.

In the above formula (f-4), $R^{F11}$ represents a hydrogen atom, a fluorine atom, a methyl group or a trifluoromethyl group; $R^{F12}$ and $R^{F13}$ each independently represent a hydrogen atom, a halogen atom, a hydroxy group or a monovalent organic group having 1 to 20 carbon atoms; w is an integer of 1 to 4, wherein in a case where w is no less than 2, a plurality of $R^{F12}$s may be identical or different, and a plurality of $R^{F13}$s may be identical or different, and at least two of one or more $R^{F12}$s and one or more $R^{F13}$s may taken together represent a cyclic structure having 3 to 20 ring atoms together with the carbon atom or the carbon chain to which the at least two of one or more $R^{F12}$s and one or more $R^{F13}$s bond; and $R^{F14}$ and $R^{F15}$ each independently represent a hydrogen atom or a monovalent organic group having 1 to 20 carbon atoms, wherein at least one of $R^{F14}$ and $R^{F15}$ represents a monovalent organic group having 1 to 20 carbon atoms and having at least one fluorine atom substituting for a hydrogen atom thereof, and wherein $R^{F14}$ and $R^{F15}$ may taken together represent a cyclic structure having 3 to 20 ring atoms together with the carbon atom to which $R^{F14}$ and $R^{F15}$ bond.

$R^{F1}$, $R^{F3}$ and $R^{F11}$ represent preferably a hydrogen atom or a methyl group, and more preferably a methyl group. $R^{F7}$ represents preferably a hydrogen atom, a methyl group or a monovalent carbonyloxy hydrocarbon group, more preferably a methyl group or an alkoxycarbonyl group, and still more preferably a methyl group or an ethoxycarbonyl group.

$L^{F1}$, $L^{F2}$ and $L^{F4}$ represent preferably a single bond, an oxygen atom or —CO—O—, and more preferably —CO—O—.

The monovalent fluorinated hydrocarbon group having 1 to 20 carbon atoms which is represented by $R^{F2}$ is exemplified by a group obtained from a monovalent hydrocarbon group having 1 to 20 carbon atoms by substituting a part or all of hydrogen atoms included therein with a fluorine atom. Examples of the monovalent hydrocarbon group having 1 to 20 carbon atoms include groups similar to those exemplified above in connection with $R^{A2}$, $R^{A6}$, $R^{A7}$ and $R^{A8}$, and the like.

$R^{F2}$ represents preferably a fluorinated chain hydrocarbon group, more preferably a fluorinated alkyl group, and still more preferably a fluorinated methyl group or a fluorinated ethyl group.

The hydrocarbon group having 1 to 20 carbon atoms and having a valency of (u+1) which may be represented by $R^{F4}$ is exemplified by a group obtained from the monovalent hydrocarbon group having 1 to 20 carbon atoms, which is exemplified in connection with $R^{A2}$, $R^{A6}$, $R^{A7}$ and $R^{A8}$, by further eliminating u hydrogen atom(s), and the like.

$R^{FF1}$ represents preferably a hydrogen atom or an alkyl group having 1 to 10 carbon atoms, and more preferably a hydrogen atom, a methyl group or an ethyl group.

$R^{F4}$ represents preferably a single bond, a chain hydrocarbon group having 1 to 20 carbon atoms and having a valency of (u+1), or an aromatic hydrocarbon group having 6 to 20 carbon atoms and having a valency of (u+1), and more preferably a single bond, a chain hydrocarbon group having 1 to 10 carbon atoms and having a valency of (u+1) or an aromatic hydrocarbon group having 6 to 10 carbon atoms and having a valency of (u+1).

The divalent organic group having 1 to 20 carbon atoms which may be represented by $R^{F5}$ or $R^{F8}$ is exemplified by a divalent hydrocarbon group, a group obtained by incorporating a divalent hetero atom-containing group between two adjacent carbon atoms or at the end on the atomic bonding side of the divalent hydrocarbon group, a group obtained by substituting with a substituent, a part or all of hydrogen atoms included in the divalent hydrocarbon group or the group obtained by incorporating a divalent hetero atom-containing group between two adjacent carbon atoms or at the end on the atomic bonding side of the divalent hydrocarbon group, and the like.

Examples of the divalent hydrocarbon group having 1 to 20 carbon atoms include:

chain hydrocarbon groups, e.g., alkanediyl groups such as a methanediyl group, an ethanediyl group, a propanediyl group and a butanediyl group;

alkenediyl groups such as an ethenediyl group, a propenediyl group and a butenediyl group; and alkynediyl groups such as an ethynediyl group, a propynediyl group and a butynediyl group;

alicyclic hydrocarbon groups, e.g., monocyclic cycloalkanediyl groups such as a cyclopropanediyl group, a cyclobutanediyl group, a cyclopentanediyl group and a cyclohexanediyl group;

monocyclic cycloalkenediyl groups such as a cyclopropenediyl group and a cyclobutenediyl group;

polycyclic cycloalkanediyl groups such as a norbornanediyl group, an adamantanediyl group, a tricyclodecanediyl group and a tetracyclododecanediyl group; and polycyclic cycloalkenediyl groups such as a norbornenediyl group and a tricyclodecenediyl group;

aromatic hydrocarbon groups, e.g., arenediyl groups such as a benzenediyl group, a toluenediyl group, a xylenediyl group and a naphthalenediyl group;

arenediyl(cyclo)alkanediyl groups such as a benzenediylmethanediyl group and a naphthalenediylcyclohexanediyl group; and the like.

The hetero atom-containing group as referred to means a group that includes a hetero atom having a valency of no less than 2 in a structure thereof. The hetero atom-containing group may include one, or two or more hetero atoms. The term "hetero atom" as referred to means an atom other than a hydrogen atom and a carbon atom. Alternatively, the hetero atom-containing group may have only the hetero atom.

The hetero atom having a valency of no less than 2 which is included in the hetero atom-containing group is not particularly limited as long as the hetero atom has a valency of no less than 2, and examples thereof include an oxygen atom, a nitrogen atom, a sulfur atom, a silicon atom, a phosphorus atom, a boron atom, and the like.

Examples of the hetero atom-containing group include —O—, —S—, —NR$^{HE}$—, —PR$^{HE}$—, —SO—, —SO$_2$—, —SO$_2$O—, —OPO(OR$^{HE}$)O—, —PO$_2$—, —PO$_2$O—, —CO—, —COO—, —COS—, —CONR$^{HE}$—, —OCOO—, —OCOS—, —OCONR$^{HE}$—, —SCONR$^{HE}$—, —SCSNR$^{HE}$—, —SCSS— group, and the like, wherein R$^{HE}$ represents a hydrogen atom or a monovalent hydrocarbon group having 1 to 20 carbon atoms.

Examples of the substituent include halogen atoms such as a fluorine atom, a chlorine atom, a bromine atom and an iodine atom, a hydroxy group, a carboxy group, a nitro group, a cyano group, and the like.

$R^{F5}$ and $R^{F8}$ represent preferably a single bond, a divalent hydrocarbon group, or a group obtained by incorporating an oxygen atom between two adjacent carbon atoms of the divalent hydrocarbon group having 1 to 20 carbon atoms, more preferably a single bond, a divalent chain hydrocarbon group having 1 to 20 carbon atoms, a group obtained by incorporating an oxygen atom between two adjacent carbon atoms of the divalent chain hydrocarbon group, or a divalent aromatic hydrocarbon group having 1 to 20 carbon atoms, and still more preferably a single bond, an alkanediyl group, an alkanediyloxyalkanediyl group or an arenediyl group.

The divalent fluorinated chain hydrocarbon group having 1 to 20 carbon atoms which may be represented by $L^{F3}$ is exemplified by a divalent fluorinated chain hydrocarbon obtained by substituting with a fluorine atom, a part or all of hydrogen atoms included in the divalent chain hydrocarbon group exemplified in connection with $R^{F5}$ and $R^{F8}$, and the like.

$L^{F3}$ represents preferably a single bond or a divalent fluorinated chain hydrocarbon group having 1 to 10 carbon atoms, and more preferably a single bond or a fluorinated alkanediyl group having 1 to 10 carbon atoms.

$A^1$ preferably represents an oxygen atom or —CO—O—.

$R^{FF2}$ represents preferably a hydrogen atom or an alkyl group having 1 to 10 carbon atoms, and more preferably a hydrogen atom, a methyl group or an ethyl group.

The monovalent organic group having 1 to 20 carbon atoms which may be represented by $R^{F6}$, $R^{F12}$, $R^{F13}$, $R^{F14}$ or $R^{F15}$ is exemplified by a monovalent hydrocarbon group, a group obtained by incorporating a divalent hetero atom-containing group between two adjacent carbon atoms or at the end on the atomic bonding side of the monovalent hydrocarbon group, a group obtained by substituting with a substituent, a part or all of hydrogen atoms included in the monovalent hydrocarbon group or the group obtained by incorporating a divalent hetero atom-containing group between two adjacent carbon atoms or at the end on the atomic bonding side of the monovalent hydrocarbon group, and the like.

Examples of the monovalent hydrocarbon group include monovalent hydrocarbon groups similar to those exemplified above in connection with $R^{42}$, $R^{46}$, $R^{47}$ and $R^{48}$. In addition, examples of the hetero atom-containing group and the substituent include groups similar to those exemplified above in connection with $R^{F5}$ and $R^{F8}$, and the like.

$R^{F6}$ represents preferably a hydrogen atom or a monovalent chain hydrocarbon group having 1 to 30 carbon atoms, more preferably a hydrogen atom or an alkyl group having 1 to 30 carbon atoms, and still more preferably a hydrogen atom or an alkyl group having 1 to 10 carbon atoms. Wherein, in the case where $L^{F3}$ represents the single bond, $R^{F6}$ preferably includes a fluorine atom.

$R^{F12}$ and $R^{F13}$ represent preferably a hydrogen atom or a monovalent hydrocarbon group having 1 to 12 carbon atoms, more preferably a monovalent hydrocarbon group having 1 to 12 carbon atoms, and still more preferably a phenyl group, a cycloalkyl group, or a hydroxy group-substituted fluorine atom-containing alkyl group.

$R^{F14}$ and $R^{F15}$ represent preferably a hydrogen atom, a monovalent hydrocarbon group having 1 to 12 carbon atoms or a monovalent hydroxy substituted fluorinated hydrocarbon group having 3 to 12 carbon atoms, more preferably a hydrogen atom, an alkyl group having 1 to 12 carbon atoms or a hydroxyfluorinated alkyl group having 3 to 12 carbon atoms, and still more preferably a hydrogen atom, a methyl group, an ethyl group or a hydroxydi(trifluoromethyl)ethyl group.

$R^{F9}$ and $R^{F10}$ represent preferably a methyl group, an ethyl group, a propyl group, a fluorinated methyl group, a fluorinated ethyl group or a fluorinated propyl group, more preferably a fluorinated methyl group or a fluorinated ethyl group, still more preferably a fluorinated methyl group, and particularly preferably a trifluoromethyl group.

In the formula (f-2), u is preferably 1 or 2, and more preferably 1. In the formula (f-3), v is preferably 1 or 2, and more preferably 1. In the formula (f-4), w is preferably 1 or 2, and more preferably 1.

The structural unit (II) is preferably a structural unit represented by any one of the following formulae.

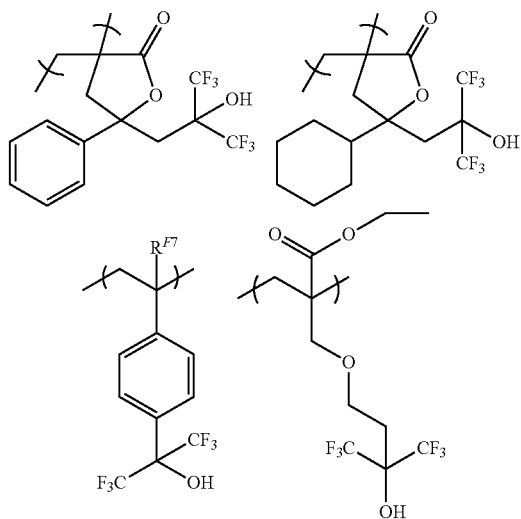

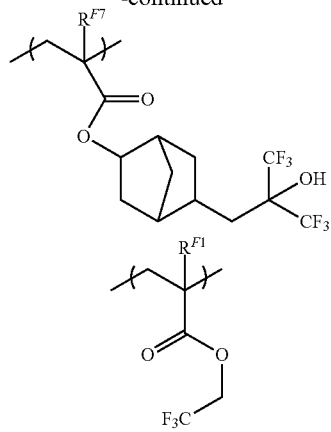

In the above formulae, $R^{F1}$ is as defined in the above formula (f-1); and $R^{F7}$ is as defined in the above formula (f-3).

In the case where the polymer (A) has the structural unit (II), the lower limit of the proportion of the structural unit (II) with respect to the total structural units constituting the polymer (A) is preferably 3 mol %, more preferably 5 mol %, and still more preferably 10 mol %. On the other hand, the upper limit of the proportion of the structural unit (II) with respect to the total structural units constituting the polymer (A) is preferably 40 mol %, more preferably 35 mol %, and still more preferably 30 mol %. When the proportion of the structural unit (II) with respect to the total structural units constituting the polymer (A) falls within the above range, the sensitivity in the case of the use of EUV and the like as patterning exposure light can be more improved. On the other hand, when the proportion of the structural unit (II) with respect to the total structural units constituting the polymer (A) is greater than the upper limit, the rectangularity of the cross-sectional shape of the resist pattern may be deteriorated.

In the case where the polymer component (1) includes the polymer (B), and the polymer (B) has the structural unit (II), the lower limit of the proportion of the structural unit (II) with respect to the total structural units constituting the polymer (B) is preferably 3 mol %, more preferably 5 mol %, and still more preferably 10 mol %. On the other hand, the upper limit of the proportion of the structural unit (II) with respect to the total structural units constituting the polymer (B) is preferably 40 mol %, more preferably 35 mol %, and still more preferably 30 mol %. When the proportion of the structural unit (II) with respect to the total structural units constituting the polymer (B) falls within the above range, the sensitivity in the case of the use of EUV and the like as patterning exposure light can be more improved. On the other hand, when the proportion of the structural unit (II) with respect to the total structural units constituting the polymer (B) is greater than the upper limit, the rectangularity of the cross-sectional shape of the resist pattern may be deteriorated.

Structural Unit (III)

The structural unit (III) includes a phenolic hydroxyl group, wherein those corresponding to the structural unit (I) and the structural unit (II) are excluded. When the polymer (A) or the polymer (B) has the structural unit (III), the sensitivity can be more improved in the case of the irradiation with a KrF excimer laser beam, EUV (extreme ultraviolet ray), an electron beam or the like in the patternwise exposure step described later.

A part or all of hydrogen atoms included in an aromatic ring to which the phenolic hydroxyl group bonds may be substituted by a substituent. Examples of the substituent include groups similar to those exemplified in connection with $R^{F5}$ and $R^{F8}$, and the like.

Examples of the structural unit (III) include structural units represented by the following formulae (h-1) to (h-5) (hereinafter, may be also referred to as "structural units (III-1) to (III-5)"), and the like.

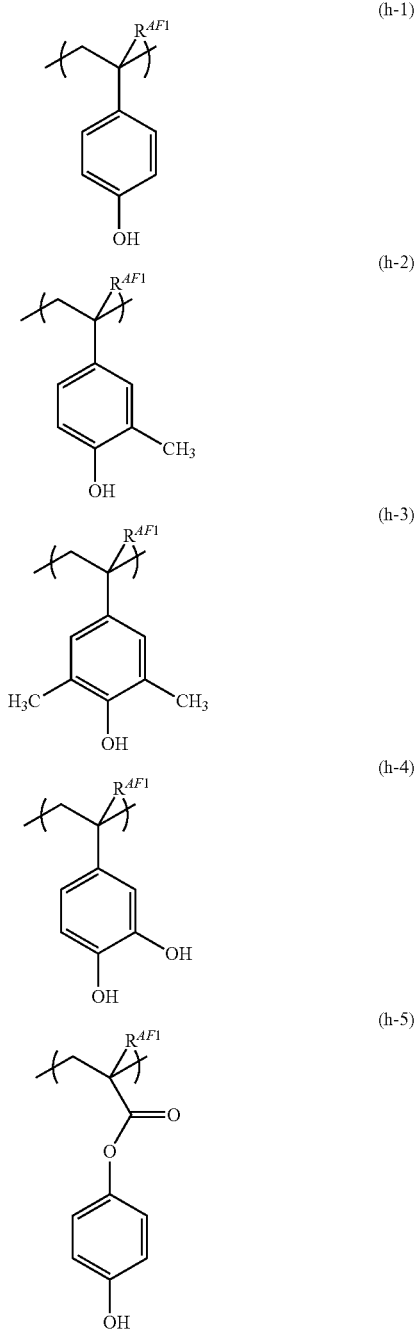

In the above formulae (h-1) to (h-6), $R^{AF1}$ represents a hydrogen atom or a methyl group.

$R^{AF1}$ represents preferably a hydrogen atom.

The structural unit (III) is preferably structural unit (III-1) or (III-2), and more preferably (III-1).

In the case where the polymer (A) has the structural unit (III), the lower limit of the proportion of the structural unit (III) with respect to the total structural units constituting the polymer (A) is preferably 1 mol %, more preferably 20 mol %, and still more preferably 40 mol %. On the other hand, the upper limit of the proportion of the structural unit (III) with respect to the total structural units constituting the polymer (A) is preferably 90 mol %, more preferably 70 mol %, and still more preferably 60 mol %. When the proportion of the structural unit (III) falls within the above range, the sensitivity of the chemically amplified resist material can be more improved.

In the case where the polymer component (1) includes the polymer (B), and the polymer (B) has the structural unit (III), the lower limit of the proportion of the structural unit (III) with respect to the total structural units constituting the polymer (B) is preferably 1 mol %, more preferably 30 mol %, and still more preferably 50 mol %. On the other hand, the upper limit of the proportion of the structural unit (III) with respect to the total structural units constituting the polymer (A) is preferably 90 mol %, more preferably 80 mol %, and still more preferably 75 mol %. When the proportion of the structural unit (III) falls within the above range, the sensitivity of the chemically amplified resist material can be more improved.

It is to be noted that the structural unit (III) may be formed by a method including: polymerizing a monomer obtained from hydroxystyrene by substitution of the hydrogen atom of an —OH group with an acetyl group or the like; and thereafter subjecting the obtained polymer to a hydrolysis reaction in the presence of an amine, or the like.

Structural Unit (IV)

The structural unit (IV) includes a lactone structure, a cyclic carbonate structure, a sultone structure or a combination thereof, wherein those corresponding to the structural units (I) to (III) are excluded. When the structural unit (IV) is further included, the polymer (A) and the polymer (B) can have more appropriately adjusted solubility in the developer solution, and as a result, the lithography performances of the chemically amplified resist material can be further improved. Also, the adhesiveness of the resist film formed from the chemically amplified resist material to the substrate can be improved. The lactone structure as referred to herein means a structure which has one ring including a group represented by —O—C(O)— (lactone ring). Moreover, the cyclic carbonate structure as referred to means a structure which has one ring including a group represented by —O—C(O)—O— (cyclic carbonate ring). The sultone structure as referred to means a structure which has one ring including a group represented by —O—S(O)$_2$— (sultone ring). Examples of the structural unit (IV) include structural units represented by the following formulae, and the like.

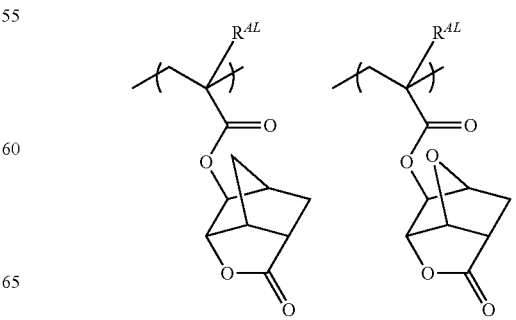

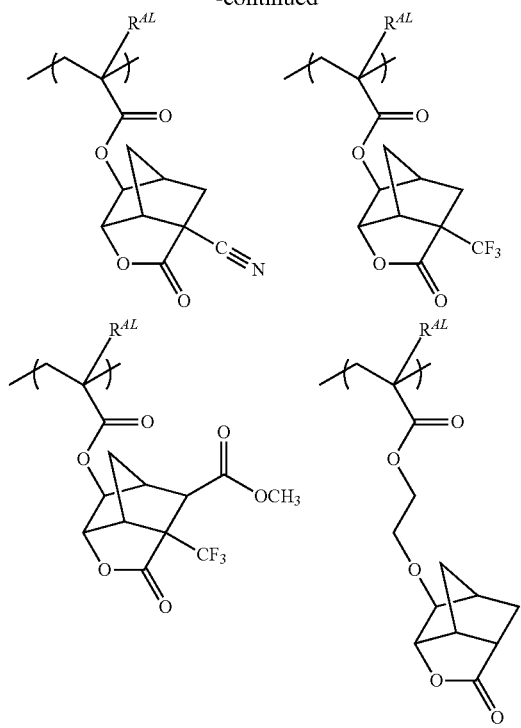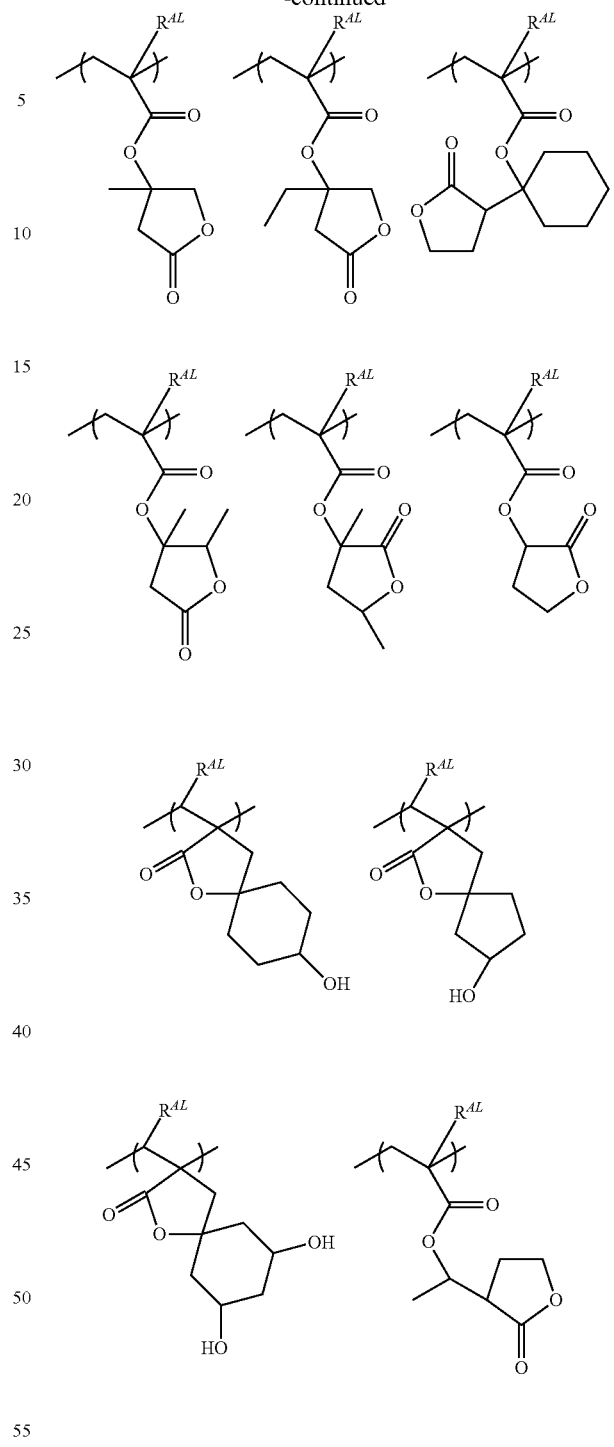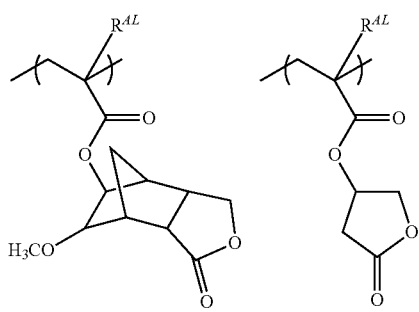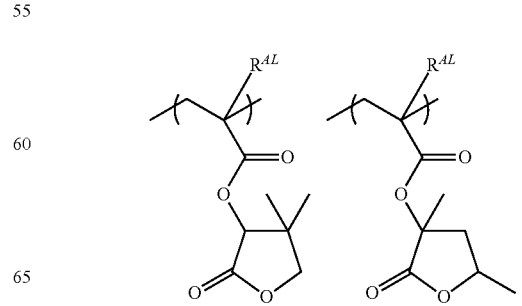

-continued
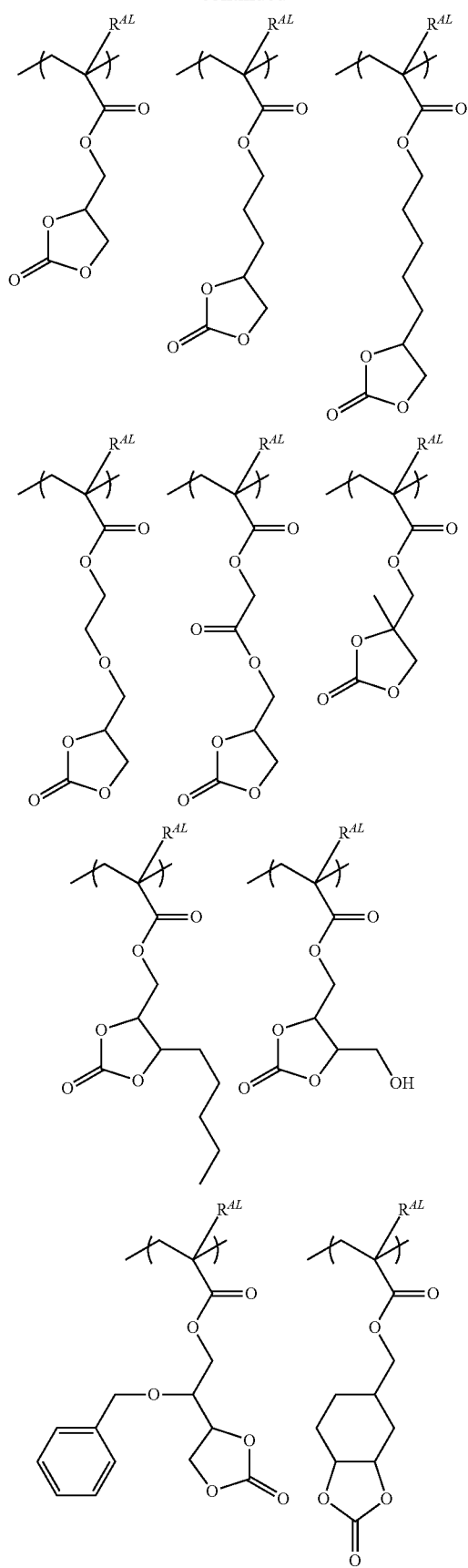
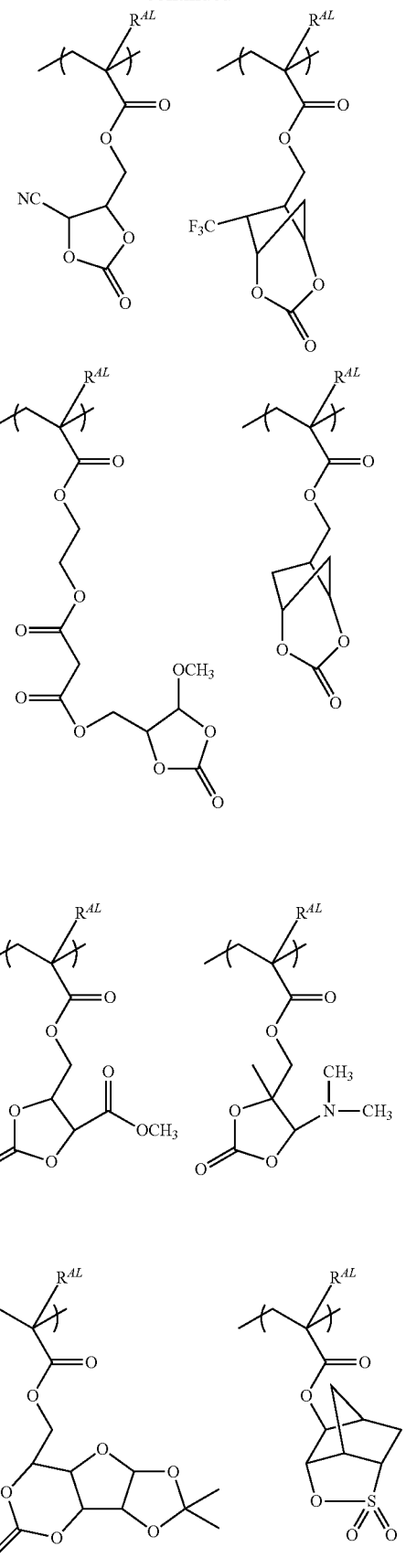

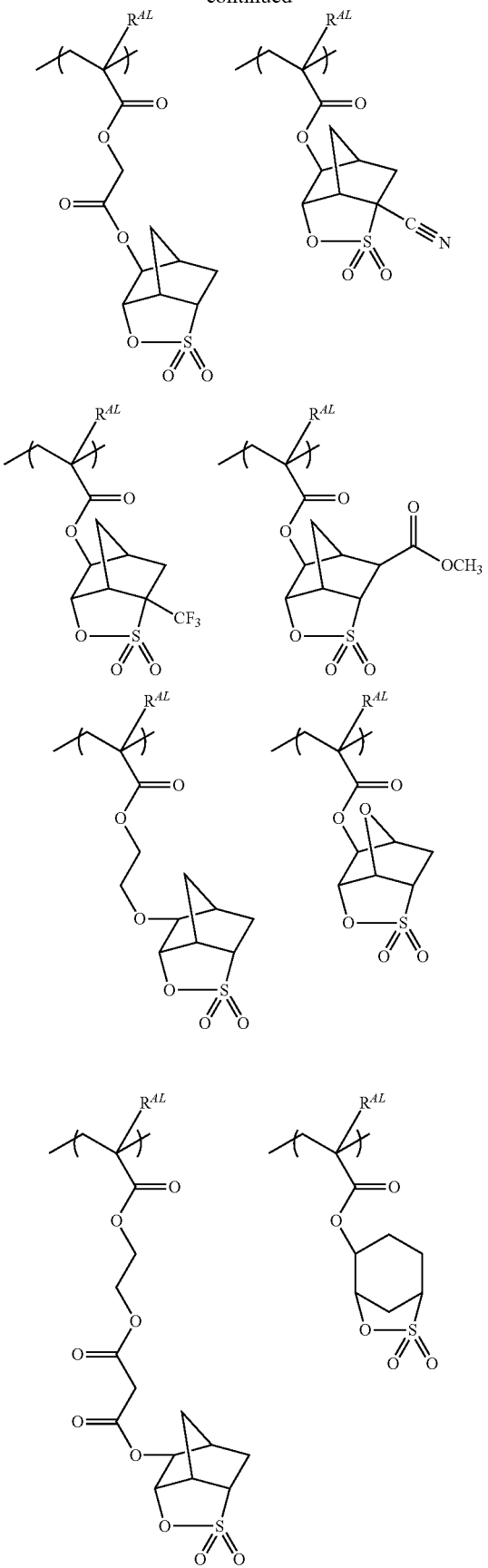
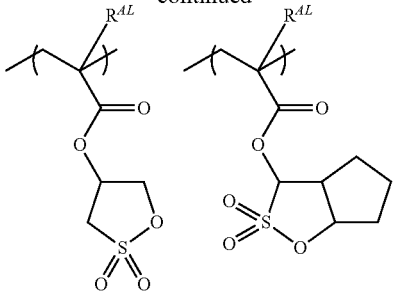

In the above formulae, $R^{AL}$ represents a hydrogen atom, a fluorine atom, a methyl group, or a trifluoromethyl group.

In light of the copolymerizability of a monomer that gives the structural unit (IV), $R^{AL}$ represents preferably a hydrogen atom or a methyl group, and more preferably a methyl group.

Of these, as the structural unit (IV), a structural unit that includes a norbornanelactone structure, a structural unit that includes an oxanorbornanelactone structure, a structural unit that includes a γ-butyrolactone structure, a structural unit that includes an ethylene carbonate structure, and a structural unit that includes a norbornanesultone structure are preferred, and a structural unit derived from norbornanelacton-yl (meth)acrylate, a structural unit derived from oxanorbornanelacton-yl (meth)acrylate, a structural unit derived from cyano-substituted norbornanelacton-yl (meth)acrylate, a structural unit derived from norbornanelacton-yloxycarbonylmethyl (meth)acrylate, a structural unit derived from butyrolacton-3-yl (meth)acrylate, a structural unit derived from butyrolacton-4-yl (meth)acrylate, a structural unit derived from 3,5-dimethylbutyrolacton-3-yl (meth)acrylate, a structural unit derived from 4,5-dimethylbutyrolacton-4-yl (meth)acrylate, a structural unit derived from 1-(butyrolacton-3-yl)cyclohexan-1-yl (meth)acrylate, a structural unit derived from ethylene carbonate-ylmethyl (meth)acrylate, a structural unit derived from cyclohexene carbonate-ylmethyl (meth)acrylate, a structural unit derived from norbornanesultone-yl (meth)acrylate, and a structural unit derived from norbornanesultone-yloxycarbonylmethyl (meth)acrylate are more preferred.

In the case where the polymer (A) has the structural unit (IV), the lower limit of the proportion of the structural unit (IV) with respect to the total structural units constituting the polymer (A) is preferably 1 mol %, more preferably 10 mol %, still more preferably 20 mol %, and particularly preferably 25 mol %. On the other hand, the upper limit of the proportion of the structural unit (IV) with respect to the total structural units constituting the polymer (A) is preferably 70 mol %, more preferably 65 mol %, still more preferably 60 mol %, and particularly preferably 55 mol %. When the proportion of of the structural unit (IV) with respect to the total structural units constituting the polymer (A) falls within the above range, the adhesiveness of the resist film formed from the chemically amplified resist material to the substrate can be further improved.

In the case where the polymer component (1) includes the polymer (B), and the polymer (B) has the structural unit (IV), the lower limit of the proportion of the structural unit (IV) with respect to the total structural units constituting the polymer (B) is preferably 1 mol %, more preferably 10 mol %, still more preferably 30 mol %, and particularly preferably 40 mol %. On the other hand, the upper limit of the proportion of the structural unit (IV) with respect to the total structural units constituting the polymer (B) is preferably 70 mol %, more preferably 65 mol %, still more preferably 60 mol %, and particularly preferably 55 mol %. When the proportion of the structural unit (IV) with respect to the total structural units constituting the polymer (B) falls within the above range, the adhesiveness of the resist film formed from the chemically amplified resist material to the substrate can be further improved.

Other Structural Unit

The polymer (A) and the polymer (B) may have other structural unit than the structural units (I) to (IV). The other structural unit is exemplified by: a structural unit that includes a structural unit that includes a polar group, a structural unit that includes a nonlabile hydrocarbon group, and the like. examples of the polar group include an alcoholic hydroxyl group, a carboxy group, a cyano group, a nitro group, a sulfonamide group, and the like. Examples of the structural unit that includes a nonlabile hydrocarbon group include a linear alkyl group, and the like. The upper limit of the proportion of the other structural unit with respect to the total structural units constituting the polymer (A) is preferably 20 mol %, and more preferably 10 mol %. The upper limit of the proportion of the other structural unit with respect to the total structural units constituting the polymer (B) is preferably 20 mol %, and more preferably 10 mol %.

The lower limit of the total content of the polymer (A) and the polymer (B) in the total solid content of the chemically amplified resist material is preferably 50% by mass, more preferably 60% by mass, and still more preferably 70% by mass. On the other hand, the upper limit of the total content of the polymer (A) and the polymer (B) in the total solid content of the chemically amplified resist material is preferably 99% by mass, more preferably 90% by mass, and still more preferably 80% by mass.

The polystyrene equivalent weight average molecular weight (Mw) as determined by gel permeation chromatography (GPC) of the polymer (A) is not particularly limited, and the lower limit thereof is preferably 1,000, more preferably 2,000, still more preferably 3,000, and particularly preferably 5,000. On the other hand, the upper limit of the Mw of the polymer (A) is preferably 50,000, more preferably 30,000, still more preferably 20,000, and particularly preferably 15,000. When the Mw of the polymer (A) falls within the above range, the application property and development defects-inhibiting property of the chemically amplified resist material may be improved. When the Mw of the polymer (A) is less than the lower limit, the resist film exhibiting sufficient heat resistance may not be obtained. To the contrary, when the Mw of the polymer (A) is greater than the upper limit, the developability of the resist film may be deteriorated.

The lower limit of the ratio (Mw/Mn) of the Mw to the polystyrene equivalent number average molecular weight (Mn) as determined by GPC of the polymer (A) is typically 1, and preferably 1.3. On the other hand, the upper limit of the ratio (Mw/Mn) is typically 5, preferably 3, and still more preferably 2.

The polystyrene equivalent weight average molecular weight (Mw) as determined by gel permeation chromatography (GPC) of the polymer (B) is not particularly limited, and the lower limit thereof is preferably 1,000, more preferably 2,000, still more preferably 2,500, and particularly preferably 3,000. On the other hand, the upper limit of the Mw of the polymer (B) is preferably 50,000, more preferably 30,000, still more preferably 20,000, and particularly preferably 15,000. When the Mw of the polymer (B) falls within the above range, the application property and development defects-inhibiting property of the chemically amplified resist material may be improved. When the Mw of the polymer (B) is less than the lower limit, the resist film exhibiting sufficient heat resistance may not be obtained. To the contrary, when the Mw of the polymer (B) is greater than the upper limit, the developability of the resist film may be deteriorated.

The lower limit of the ratio (Mw/Mn) of the Mw to the polystyrene equivalent number average molecular weight (Mn) as determined by GPC of the polymer (B) is preferably 1. On the other hand, the upper limit of the ratio (Mw/Mn) is preferably 5, more preferably 3, and still more preferably 2.

Herein, the Mw and the Mn of the polymer are determined using gel permeation chromatography (GPC) under the following conditions.

GPC columns: G2000 HXL×2, G3000 HXL×1 and G4000 HXL×1 (each available from Tosoh Corporation)
column temperature: 40° C.
elution solvent: tetrahydrofuran
flow rate: 1.0 mL/min
sample concentration: 1.0% by mass
amount of injected sample: 100 μL
detector: differential refractometer
standard substance: mono-dispersed polystyrene The polymer (A) and the polymer (B) may include a low-molecular weight component having a molecular weight of no greater than 1,000. The upper limit of the content of the low-molecular weight component in the polymer (A) is preferably 1.0% by mass, more preferably 0.5% by mass, and still more preferably 0.3% by mass. The lower limit of the content of the low-molecular weight component in the polymer (A) is 0.01% by mass, for example. The upper limit of the content of the low-molecular weight component in the polymer (B) is preferably 1.0% by mass, more preferably 0.5% by mass, and still more preferably 0.3% by mass. The lower limit of the content of the low-molecular weight component in the polymer (B) is 0.01% by mass, for example. When the content of the low-molecular weight component in the polymer (A) or the polymer (B) falls within the above range, the lithography performances of the chemically amplified resist material can be more improved.

Herein, the content of the low molecular weight component in the polymer is determined by high performance liquid chromatography (HPLC) under the following conditions.

column: "Inertsil ODS-25 μm column" (4.6 mmφ×250 mm) available from GL Sciences, Inc.
eluent: acrylonitrile/0.1% by mass aqueous phosphoric acid solution
flow rate: 1.0 mL/min
sample concentration: 1.0% by mass
amount of injected sample: 100 μL
detector: differential refractometer The lower limit of the percentage content of fluorine atom in the polymer (A) and the polymer (B) is preferably 1% by mass, more preferably 2% by mass, still more preferably 4% by mass, and particularly preferably 7% by mass. On the other hand, the upper limit of the percentage content of fluorine atom in the polymer (A) and the polymer (B) is preferably 60% by mass, more preferably 40% by mass, and still more preferably 30% by mass. In this regard, the percentage content of fluorine atom (% by mass) of the polymer can be calculated based on the polymer structure determined by $^{13}$C-NMR spectroscopy.

The polymer component (1) preferably contains at least two polymers each having a different percentage content of fluorine atom. The polymer component (1) is exemplified by: a polymer component that contains the polymer (A) and the polymer (B) in which the polymer (B) has a greater percentage content of fluorine atom than that of the polymer (A); a polymer component that contains the polymer (A) and the polymer (B) in which the polymer (A) has a greater percentage content of fluorine atom than that of the polymer (B); a polymer component that contains at least two polymers (A) each having a different percentage content of fluorine atom; a polymer component that contains at least two polymers (B) each having a different percentage content of fluorine atom; and the like. When the polymer component (1) thus contains the at least two polymers each having a different percentage content of fluorine atom, a polymer having a higher percentage content of fluorine atom is allowed to be localized in the surface region of the resist film, and can function as a water repellent polymer additive. As a result, elution of the generative component (2) and the like from the resist film can be inhibited, and the dynamic contact angle of the surface of the formed resist film can be more desirable, thereby enabling superior water draining properties to be achieved. Thus, an exposure by high speed scanning is enabled when liquid immersion lithography is carried out as described later.

Synthesis Method of Polymer (A) and Polymer (B)

The polymer (A) and the polymer (B) may be produced by, for example, polymerizing monomer(s) each corresponding to the predetermined structural unit in an appropriate polymerization reaction solvent using a polymerization initiator such as a radical polymerization initiator. Regarding specific synthesis methods, for example, a procedure that involves adding a solution containing a monomer and a radical polymerization initiator dropwise to a solution containing a polymerization reaction solvent or a monomer to permit a polymerization reaction; a procedure that involves separately adding a solution containing a monomer and a solution containing a radical polymerization initiator dropwise to a solution containing a polymerization reaction solvent or a monomer to permit a polymerization reaction; a procedure that involves separately adding a plurality of kinds of solutions containing each monomer, and a solution containing a radical polymerization initiator dropwise to a solution containing a polymerization reaction solvent or a monomer to permit a polymerization reaction; and the like may be referred to.

Examples of the radical polymerization initiator include: azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate; peroxide radical initiators such as benzoyl peroxide, t-butyl hydroperoxide and cumene hydroperoxide; and the like. Of these, the radical polymerization initiator is preferably AIBN or dimethyl 2,2'-azobisisobutyrate, and more preferably AIBN. These radical initiators may be used either alone of one type, or in combination of two or more types thereof.

Examples of the solvent which may be used in the polymerization include solvents similar to those which may be contained in the chemically amplified resist material and will be described later.

The lower limit of the reaction temperature in the polymerization is preferably 40° C., and more preferably 50° C. On the other hand, the upper limit of the reaction temperature is preferably 150° C., and more preferably 120° C. The lower limit of the reaction time period in the polymerization is preferably 1 hour. On the other hand, the upper limit of the reaction time period is preferably 48 hrs, and more preferably 24 hrs.

The polymer (A) and the polymer (B) are preferably recovered according to a reprecipitation technique. More specifically, after the completion of the reaction, the intended copolymer is recovered in the form of a powder through charging the reaction mixture into a reprecipitation solvent. Alcohols, alkanes and the like may be used as the reprecipitation solvent, either alone of one type or in combination of two or more types thereof. In addition to the reprecipitation technique, a liquid separating operation, a column operation, an ultrafiltration operation or the like enables the polymer to be recovered through eliminating the low-molecular weight component such as monomers and oligomers.

(C) Polymer

The polymer (C) is the calixarene having the structural unit (I). The chemically amplified resist material containing the polymer (C) having the polymer component (1) enables the nanoedge roughness performance to be further improved. The structural unit (I) included in the polymer (C) is exemplified by a structural unit represented by the following formula (2-3) (hereinafter, may be also referred to as "structural unit (I-3)"), and the like. The polymer (C) as a structure in which the structural unit (I) is linked via a chain hydrocarbon group.

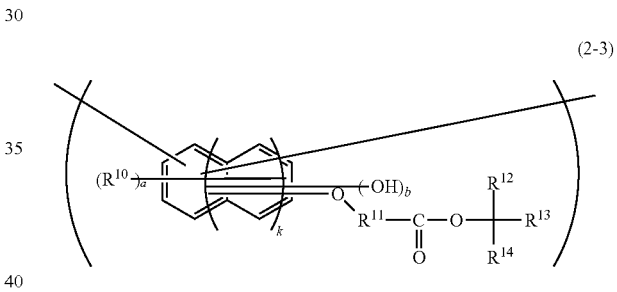

(2-3)

In the above formula (2-3), $R^{10}$ represents a monovalent hydrocarbon group having 1 to 20 carbon atoms or a monovalent oxyhydrocarbon group having 1 to 20 carbon atoms; $R^{11}$ represents a single bond or a divalent hydrocarbon group having 1 to 10 carbon atoms; $R^{12}$ represents a monovalent hydrocarbon group having 1 to 20 carbon atoms; $R^{13}$ and $R^{14}$ each independently represent a monovalent hydrocarbon group having 1 to 20 carbon atoms, or $R^{13}$ and $R^{14}$ taken together represent an alicyclic structure having 3 to 20 ring atoms together with the carbon atom to which $R^{13}$ and $R^{14}$ Bond; a is an integer of 0 to 6; b is an integer of 0 to 6, wherein a+b is no greater than 5; and k is 0 or 1, wherein in a case a where a is no less than 2, a plurality of $R^{10}$s may be identical or different.

The monovalent hydrocarbon group having 1 to 20 carbon atoms which may be represented by $R^{10}$ is exemplified by groups similar to those exemplified above in connection with $R^{42}$, $R^{46}$, $R^{47}$ and $R^{48}$, and the like. The monovalent oxyhydrocarbon group having 1 to 20 carbon atoms which may be represented by $R^{10}$ is exemplified by groups including an oxygen atom between two adjacent carbon atoms or at the end on the atomic bonding side of the aforementioned monovalent hydrocarbon group, and the like.

$R^{10}$ represents preferably an oxyhydrocarbon group, more preferably an alkoxy group, and still more preferably a methoxy group.

The divalent hydrocarbon group having 1 to 10 carbon atoms represented by $R^{11}$ is exemplified by groups having 1 to 10 carbon atoms group among those obtained by eliminating one hydrogen atom from the monovalent hydrocarbon group exemplified above in connection with $R^{42}$, $R^{46}$, $R^{47}$ and $R^{48}$, and the like.

$R^{11}$ represents preferably a single bond or an alkanediyl group, and more preferably a methanediyl group.

The monovalent hydrocarbon group having 1 to 20 carbon atoms which may be represented by $R^{12}$, $R^{13}$ and $R^{14}$ is exemplified by groups similar to those exemplified above in connection with $R^{42}$, $R^{46}$, $R^{47}$ and $R^{48}$, and the like.

The alicyclic structure having 3 to 20 ring atoms which may be taken together represented by groups of $R^{13}$ and $R^{14}$ together with the carbon atom to which $R^{13}$ and $R^{14}$ bond is exemplified by structures similar to those exemplified above in connection with $R^{43}$ and $R^{44}$, and the like.

In the above formula (2-3), a is preferably an integer of 0 to 2, and more preferably 1; and b is preferably an integer of 0 to 2, and more preferably 1.

The polymer (C) may have other structural unit in addition to the structural unit (I-3). The other structural unit is exemplified by a structural unit that includes a phenolic hydroxyl group, and the like.

The lower limit of the molecular weight of the polymer (C) is preferably 500, and more preferably 1,000. The upper limit of the molecular weight of the polymer (C) is preferably 3,000, and more preferably 2,500. When the molecular weight of the polymer (C) falls within the above range, the sensitivity and nanoedge roughness performance of the chemically amplified resist material can be further improved.

The polymer (C) may be synthesized by, for example, the following method. First, a compound having a phenolic hydroxyl group represented by the following formula (a) is reacted with an aldehyde represented by the following formula (b) in the presence of an acid such as trifluoroacetic acid in a solvent such as chloroform. Next, a compound thus obtained is reacted with a compound that provides an acid-labile group such as 2-bromoacetyloxy-2-methyladamantane in the presence of a base such as potassium carbonate, in a solvent such as N-methylpyrrolidone, thereby enabling the polymer (C) to be synthesized.

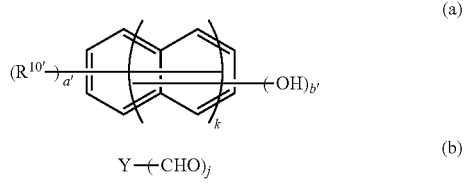

(a)

(b)

In the above formula (a), $R^{10'}$ represents a hydrocarbon group having 1 to 20 carbon atoms; a' is an integer of 0 to 7; b' is an integer of 1 to 7, wherein a'+b' is no greater than 8; and k is 0 or 1, wherein in a case where a' is no less than 2, a plurality of $R^{10'}$s may be identical or different.

In the above formula (b), Y represents a substituted or unsubstituted hydrocarbon group having 1 to 30 carbon atoms and having a valency of j, or a hydrogen atom; and j is 1 or 2.

It is preferred that j is 2. Y represents preferably an unsubstituted divalent hydrocarbon group, more preferably an alkanediyl group, and still more preferably a propanediyl group.

(2) Component that is Capable of Generating Radiation-Sensitive Sensitizer and Acid Upon Exposure The generative component (2) generates a radiation-sensitive sensitizer and an acid upon an exposure (irradiation with a radioactive ray). Among three components of (a) a radiation-sensitive acid-and-sensitizer generating agent, (b) a radiation-sensitive sensitizer generating agent, and (c) a radiation-sensitive acid generating agent, the component (2) contains the components (a) and (b), the components (b) and (c), or all of the components (a) to (c).

(a) Radiation-Sensitive Acid-And-Sensitizer Generating Agent

The radiation-sensitive acid-and-sensitizer generating agent (a) is capable of generating, upon the irradiation with the first radioactive ray, an acid and a radiation-sensitive sensitizer that absorbs the second radioactive ray, but substantially does not generate the acid and the radiation-sensitive sensitizer upon the irradiation with the second radioactive ray without the irradiation with the first radioactive ray.

The radiation-sensitive acid-and-sensitizer generating agent (a) is exemplified by an onium salt compound, a diazomethane compound, a sulfonimide compound, and the like. The onium salt compound is exemplified by a sulfonium salt compound, a tetrahydrothiophenium salt compound, an iodonium salt compound, and the like. In light of the high reduction potential, the radiation-sensitive acid-and-sensitizer generating agent (a) is preferably the sulfonium salt compound or the iodonium salt compound, and more preferably the iodonium salt compound.

The sulfonium salt compound as referred to is constituted with a sulfonium cation and an acid anion. As the sulfonium salt compound, compounds represented by the following formulae (I) to (III) are preferred.

(I)

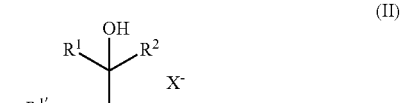

(II)

(III)

In the above formulae (I) to (III), $R^1$, $R^2$, $R^{1'}$, $R^{2'}$, $R^{1''}$, $R^{2''}$, $R^3$ and $R^4$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group, preferably an alkyl group having 1 to 30 carbon atoms, preferably 1 to 5 carbon atoms; a phenoxy group substituted with an alkoxy group having 1 to 5 carbon atoms, a hydroxy group, an amino group, an amide group, or an alkyl group having 1 to 5 carbon atoms; a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxy group; a naphthoxy group substituted with an alkoxy group having 1 to 5 carbon atoms, an alkyl group having 1 to 5 carbon atoms, an amino group, an amide group, or a hydroxy group; an anthracenoxy group substituted with an alkoxy group having 1 to 5 carbon atoms, an alkyl group having 1 to 5 carbon atoms, an amino group, an amide group, or a hydroxy group; a saturated or unsaturated linear, branched or cyclic hydrocarbon group, preferably an alkyl group, having 1 to 30 carbon atoms, preferably 1 to 5 carbon atoms, substituted with an alkoxy group having 1 to 5 carbon atoms, a phenoxy group, a naphthoxy group, an anthracenoxy group, an amino group, an amide group, or a hydroxy group; or a carbonyl group to which an alkyl group having 1 to 12 carbon atoms bonds. In the above formulae (I) to (III), the hydrogen atom of the hydroxy group may be substituted with: a phenyl group; a halogen atom; a saturated or unsaturated linear, branched or cyclic hydrocarbon group, preferably an alkyl group, having 1 to 30 carbon atoms, preferably 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxy group. In a case where the hydrogen atom of the hydroxy group is substituted, the sulfonium salt compound shall include a ketal compound group or an acetal compound group. In the formula (I), any at least two of the groups represented by $R^1$, $R^2$, $R^3$ and $R^4$ may taken together represent a cyclic structure via a single bond or a double bond, or via a bond that includes —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. In the formulae (II), any at least two of the groups represented by $R^1$, $R^2$, $R^{1\prime}$, $R^{2\prime}$ and $R^4$ may taken together represent a cyclic structure via a single bond or a double bond, or via a bond that includes —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. In the formula (III), any at least two of the groups represented by $R^1$, $R^2$, $R^{1\prime}$, $R^{2\prime}$, $R^{1\prime\prime}$ and $R^{2\prime\prime}$ may taken together represent a cyclic structure via a single bond or a double bond, or via a bond that includes —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. $R^e$ represents: a phenyl group; a phenoxy group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxy group, or an alkyl group having 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxy group. $R^1$, $R^2$, $R^{1\prime}$, $R^{2\prime}$, $R^{1\prime\prime}$, $R^{2\prime\prime}$, $R^3$ and $R^4$ each independently represent preferably: a phenyl group; a phenoxy group; a phenoxy group substituted with an alkyl group having 1 to 5 carbon atoms; or a phenyl group substituted with an alkoxy group having 1 to 5 carbon atoms or a hydroxy group. In the formulae (I) to (III), $X^-$ represents an anion derived from an acid, preferably a strong acid, and more preferably a superacid.

In the above formulae (I) to (III), examples of the group represented by —C(—OH)$R^1R^2$, —C(—OH)$R^{1\prime}R^{2\prime}$, —C(—OH)$R^{1\prime\prime}R^{2\prime\prime}$ or the like include groups represented by the following formulae. It is to be noted that * in the formulae denotes a binding site to the sulfur ion in the above formulae (I) to (III). In the group represented by —C(—OH)$R^1R^2$, —C(—OH)$R^{1\prime}R^{2\prime}$, or —C(—OH)$R^{1\prime\prime}R^{2\prime\prime}$, the hydroxy group and the carbon atom to which the hydroxy group bonds are to give a carbonyl group upon the patternwise exposure. Thus, in the compounds represented by the above formulae (I) to (III), the group represented by —C(—OH)$R^1R^2$, —C(—OH)$R^{1\prime}R^{2\prime}$, or —C(—OH)$R^{1\prime\prime}R^{2\prime\prime}$ is dissociated after the patternwise exposure to generate the radiation-sensitive sensitizer.

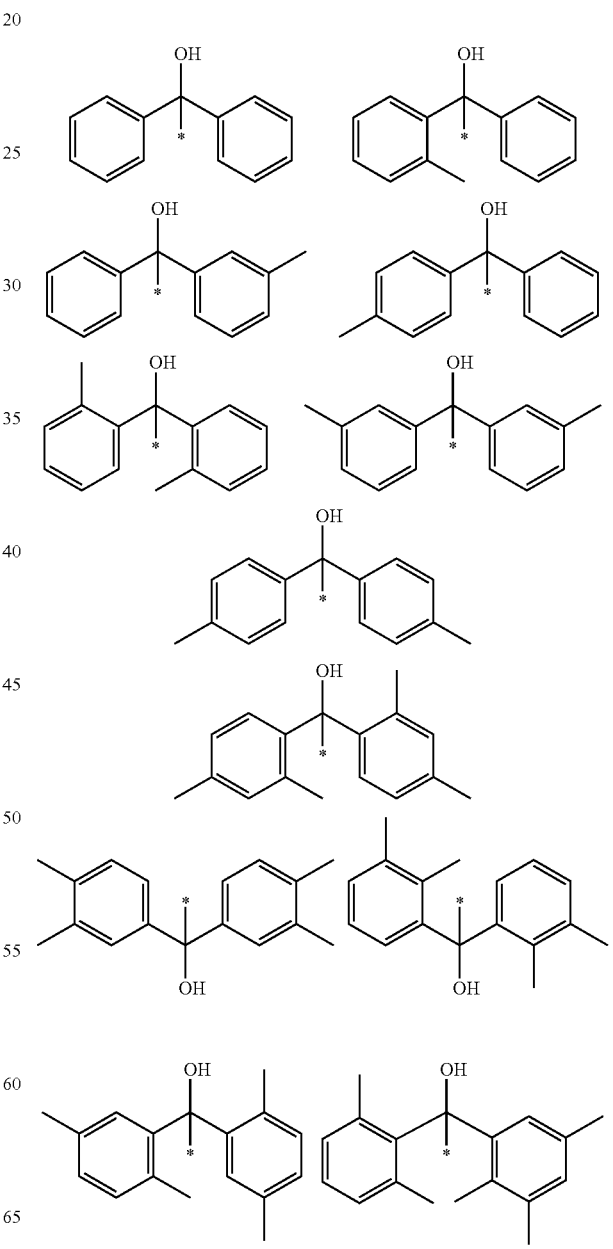

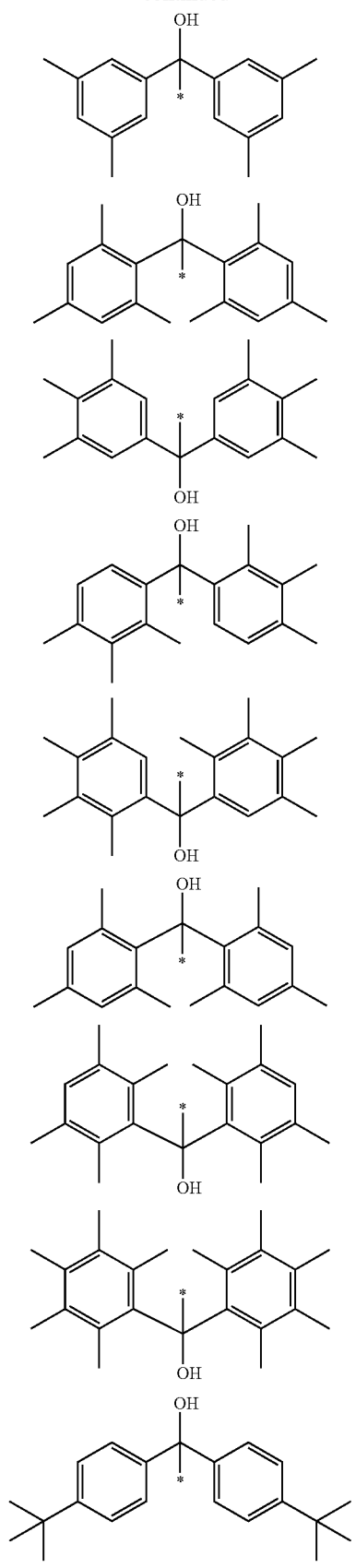
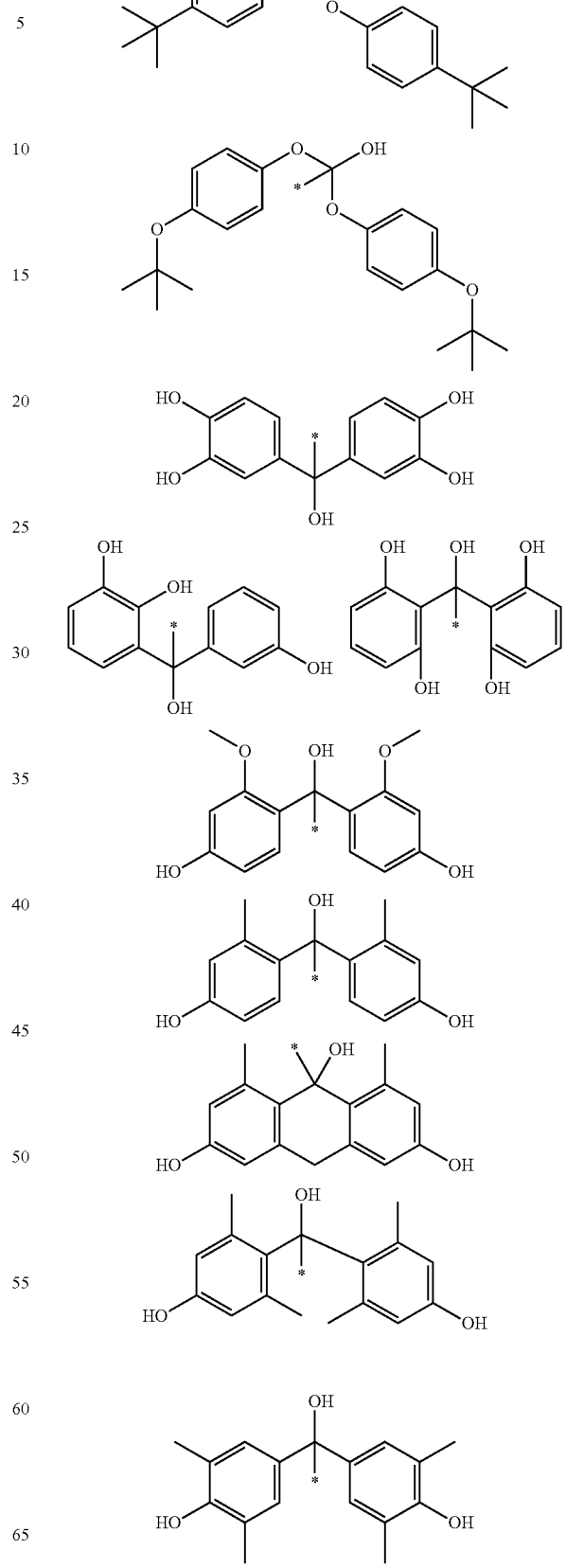

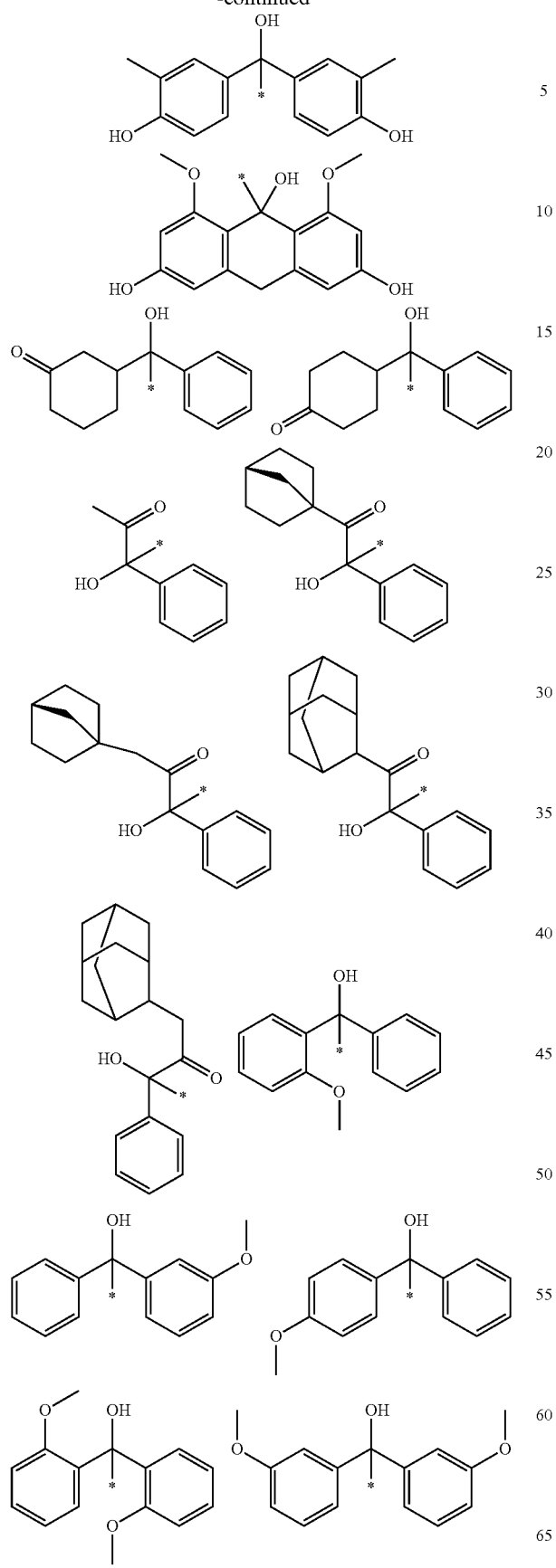
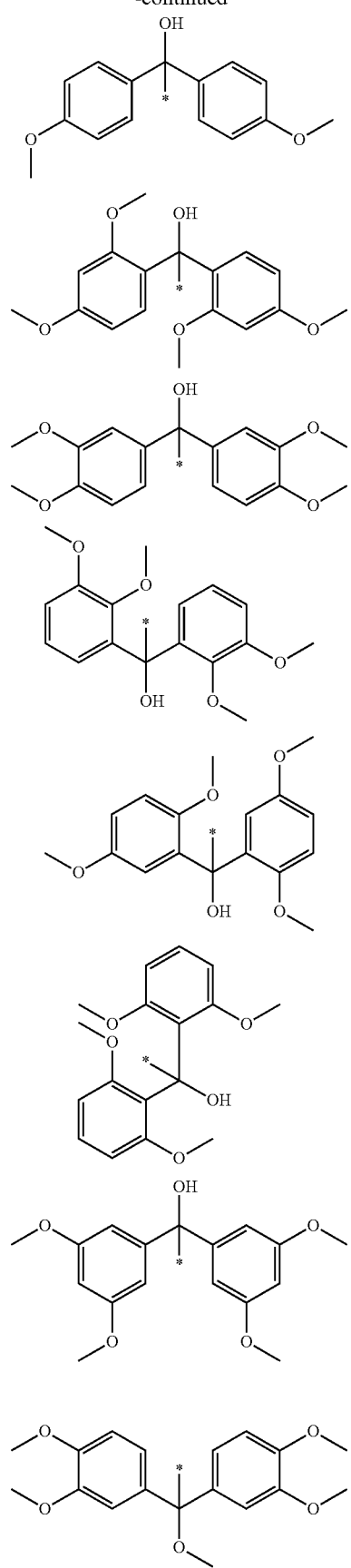

-continued
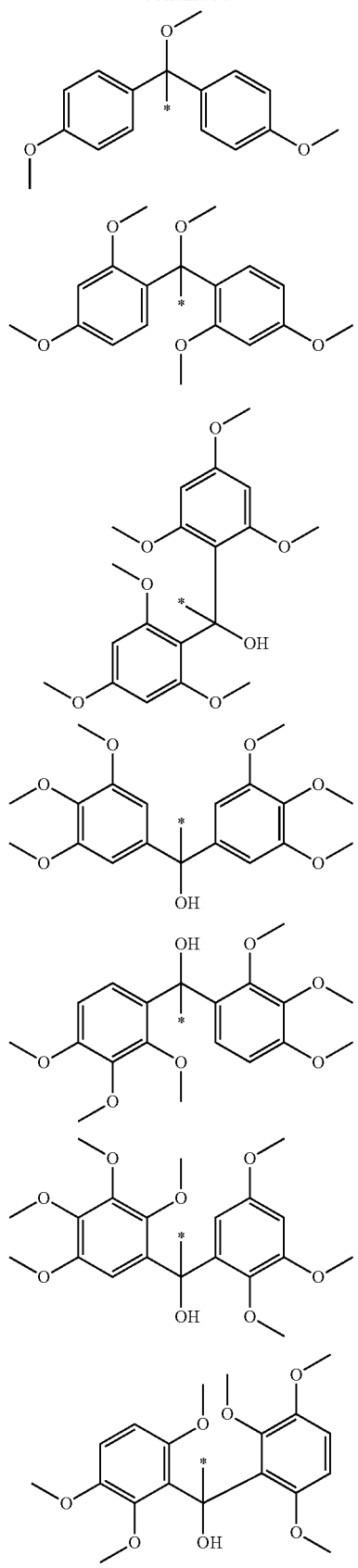
-continued
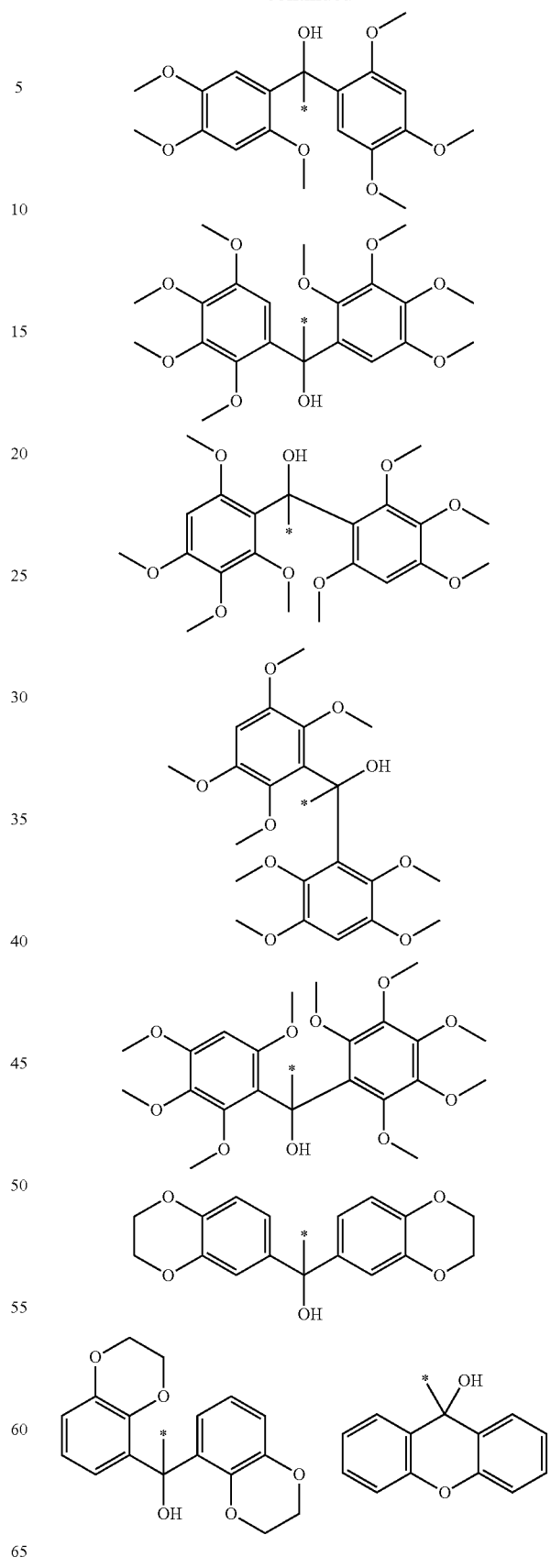

-continued
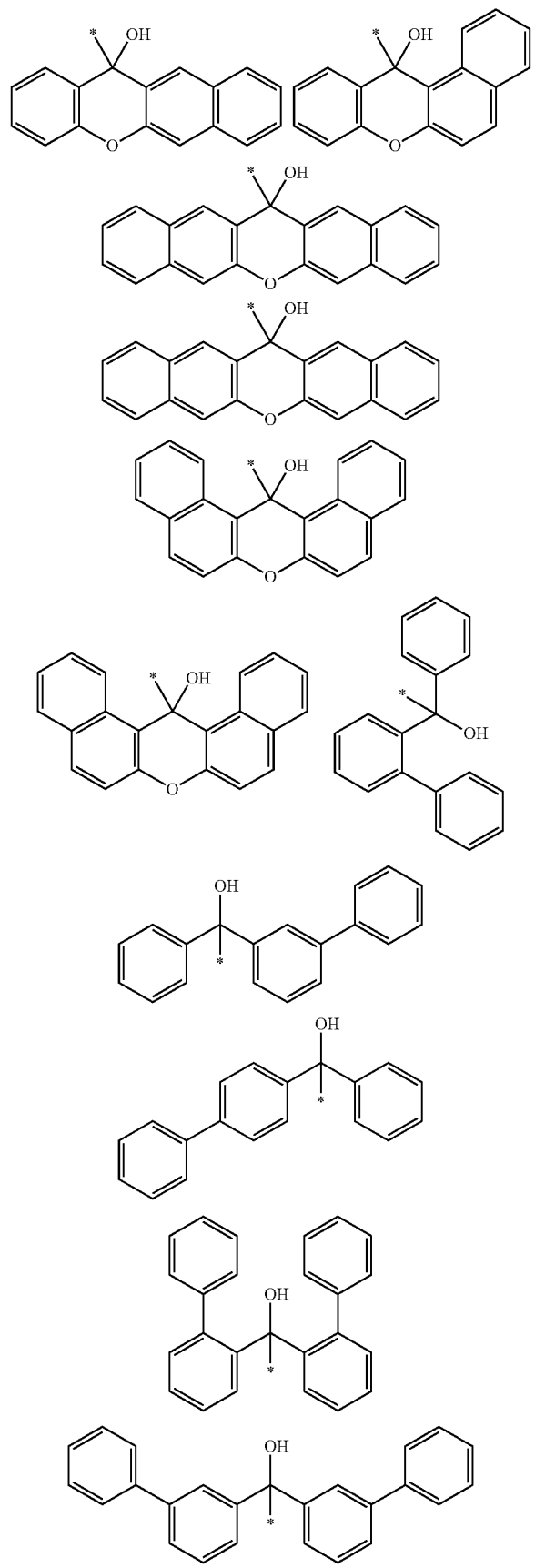
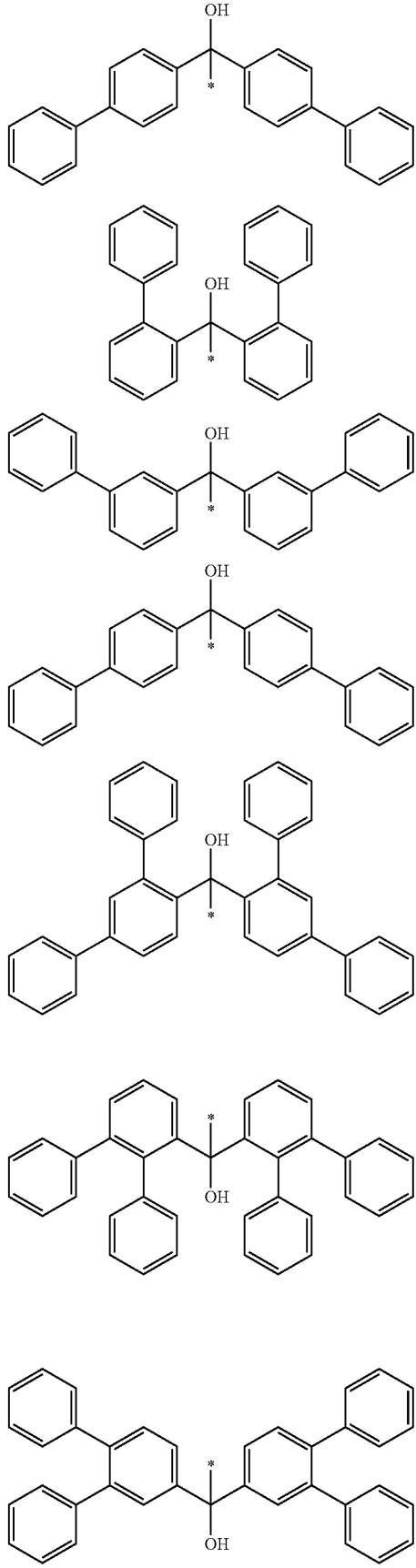

-continued
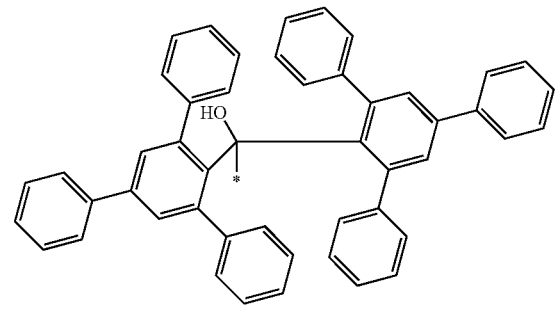
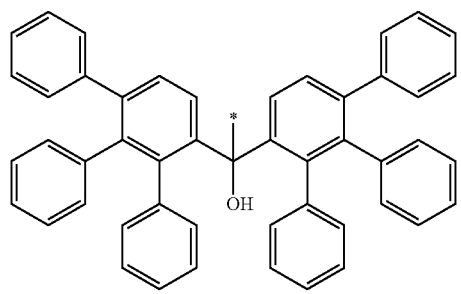
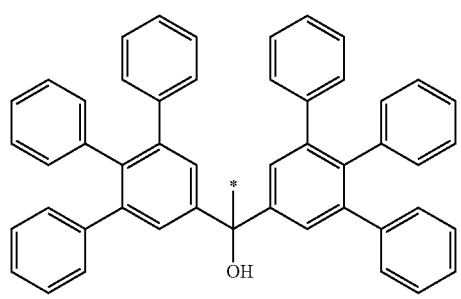
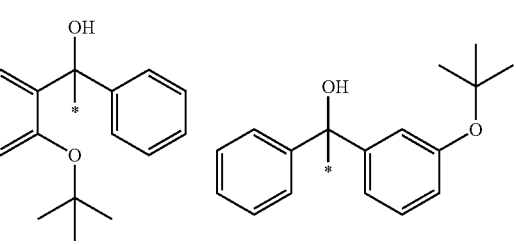
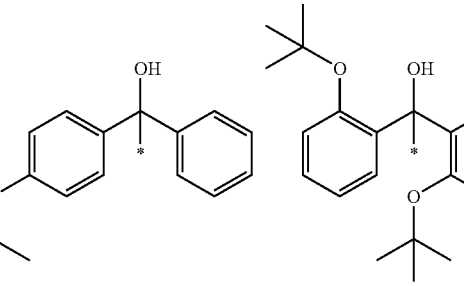
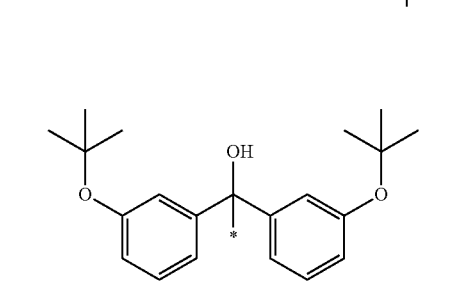
-continued
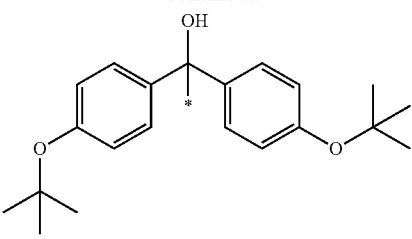
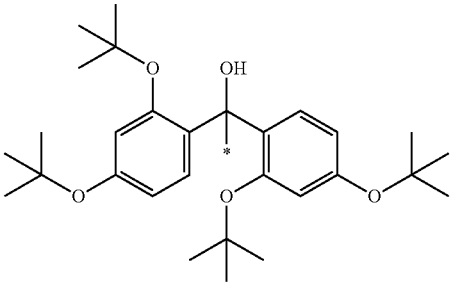
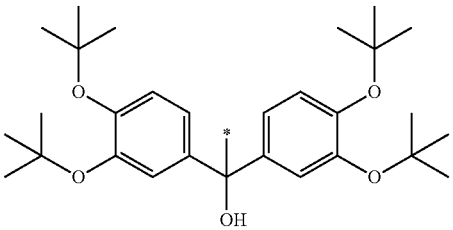
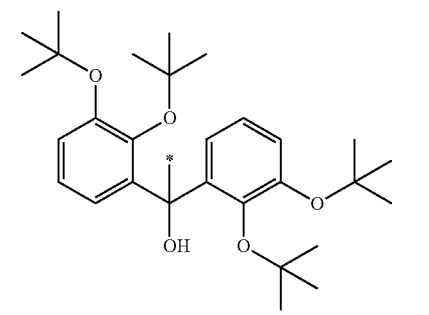
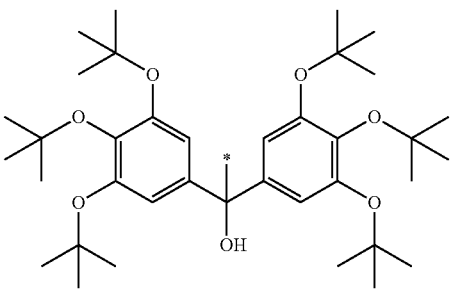

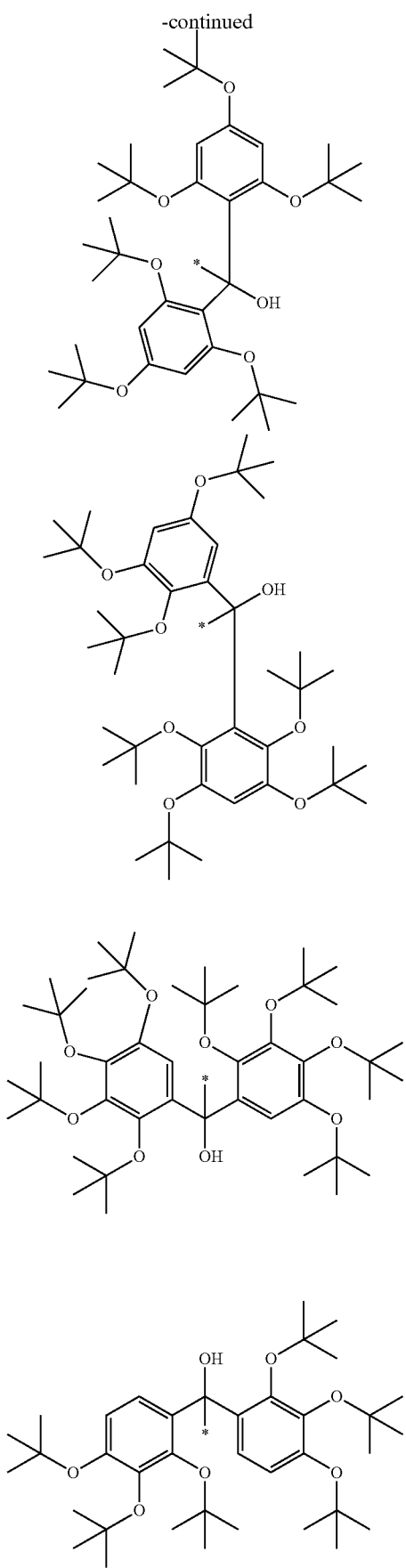
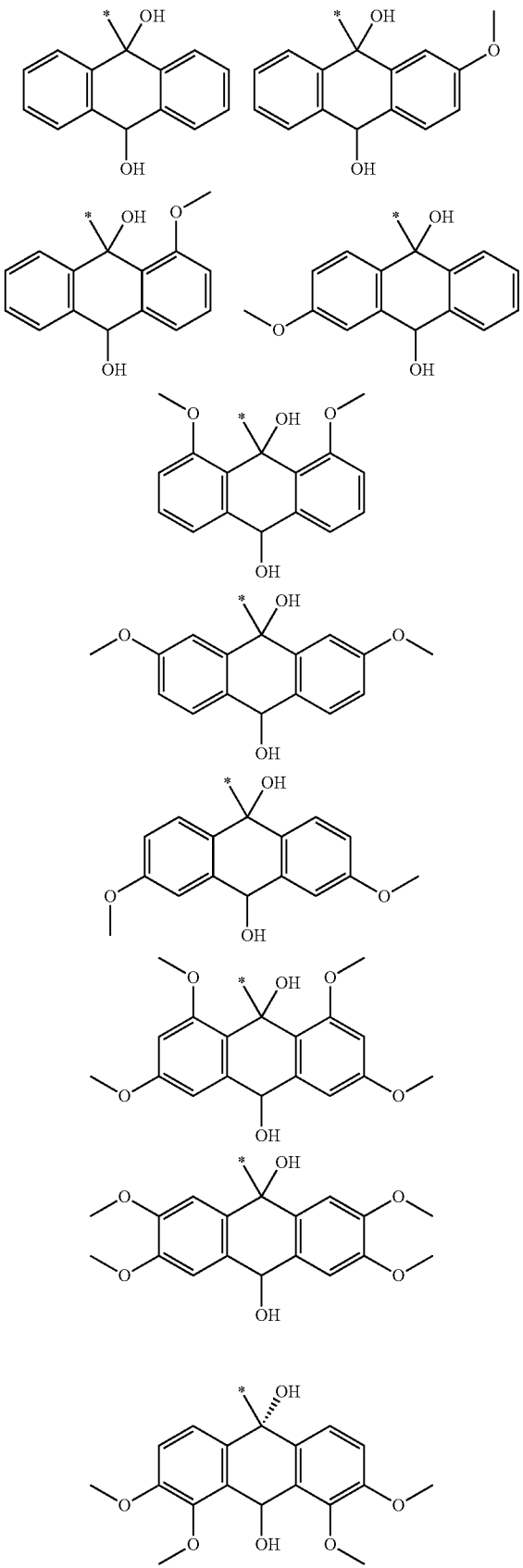

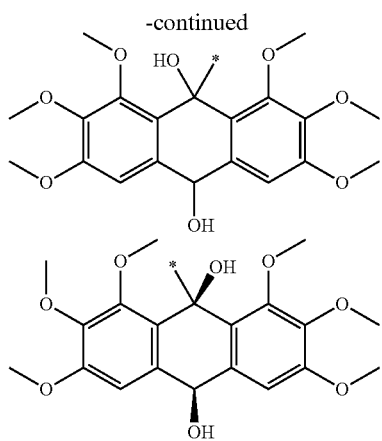

The iodonium salt compound is constituted with an iodonium cation and an acid anion. As the iodonium salt compound, compounds represented by the following formulae (IV) to (V) are preferred.

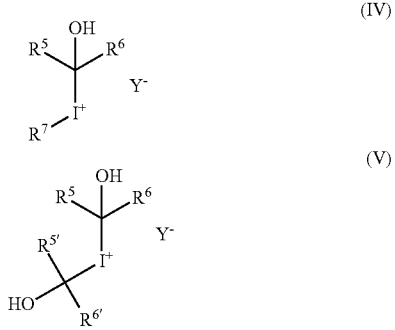

In the above formulae (IV) to (V), $R^5$, $R^6$, $R^{5'}$, $R^{6'}$, and $R^7$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxy group, an amino group, an amide group, or an alkyl group having 1 to 5 carbon atoms; a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxy group; a naphthoxy group substituted with an alkoxy group having 1 to 5 carbon atoms, an alkyl group having 1 to 5 carbon atoms, an amino group, an amide group, or a hydroxy group; an anthracenoxy group substituted with an alkoxy group having 1 to 5 carbon atoms, an alkyl group having 1 to 5 carbon atoms, an amino group, an amide group, or a hydroxy group; a saturated or unsaturated linear, branched or cyclic hydrocarbon group, preferably an alkyl group, having 1 to 30 carbon atoms, preferably 1 to 5 carbon atoms, substituted with an alkoxy group having 1 to 5 carbon atoms, a phenoxy group, a naphthoxy group, an anthracenoxy group, an amino group, an amide group, or a hydroxy group; or a carbonyl group to which an alkyl group having 1 to 12 carbon atoms bonds. In the above formulae (IV) to (V), the hydrogen atom of the hydroxy group may be substituted with: a phenyl group; a halogen atom; a saturated or unsaturated linear, branched or cyclic hydrocarbon group, preferably an alkyl group, having 1 to 30 carbon atoms, preferably 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxy group. In a case where the hydrogen atom of the hydroxy group is substituted, the iodonium salt compound shall include a ketal compound group or an acetal compound group. In the formula (IV), any at least two of the groups represented by $R^5$, $R^6$ and $R^7$ may taken together represent a cyclic structure via a single bond or a double bond, or via a bond that includes —CH$_2$—, —O—, —S—, —SO$_2$NH—, —C(=O)—, —C(=O)O—, —NHCO—, —NHC(=O)NH—, —CHR$^f$—, —CR$^f{}_2$—, —NH— or —NR$^f$—. In the formula (V), any at least two of the groups represented by $R^5$, $R^6$, $R^{5'}$ and $R^{6'}$ may taken together represent a cyclic structure via a single bond or a double bond, or via a bond that includes —CH$_2$—, —O—, —S—, —SO$_2$NH—, —C(=O)—, —C(=O)O—, —NHCO—, —NHC(=O)NH—, —CHR$^f$—, —CR$^f{}_2$—, —NH— or —NR$^f$—. R$^f$ represents: a phenyl group; a phenoxy group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxy group, or an alkyl group having 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxy group. $R^5$, $R^6$, $R^{5'}$, $R^{6'}$, and $R^7$ each independently represent preferably: a phenyl group; a phenoxy group; a phenoxy group substituted with an alkoxy group having 1 to 5 carbon atoms, a hydroxy group, or an alkyl group having 1 to 5 carbon atoms; or a phenyl group substituted with an alkoxy group having 1 to 5 carbon atoms or a hydroxy group. In the formulae (IV) to (V), Y$^-$ represents an anion derived from an acid, preferably a strong acid, and more preferably a superacid.

In the above formulae (IV) to (V), examples of the group represented by —C(—OH)R$^5$R$^6$ or —C(—OH)R$^{5'}$R$^{6'}$ include groups similar to those exemplified as the group represented by —C(—OH)R$^1$R$^2$, —C(—OH)R$^1$R$^{2'}$, —C(—OH)R$^{1''}$R$^{2''}$ or the like in connection with the above formulae (I) to (III).

The acid anion in the sulfonium salt compound and the iodonium salt compound is exemplified by a sulfonic acid anion, a carboxylic acid anion, a bis(alkylsulfonyl)amide anion, a tris(alkylsulfonyl)methide anion, and the like, and acid anions represented by the following general formulae (XX), (XXI) and (XXII) are preferred, and an acid anion represented by the following general formula (XX) is more preferred.

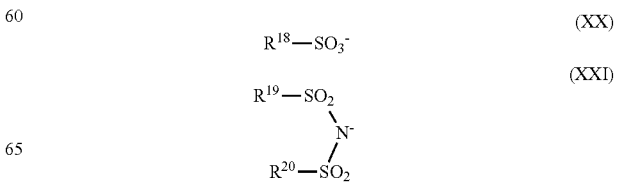

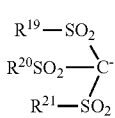
(XXII)

In the above general formulae (XX), (XXI) and (XXII), $R^{18}$ to $R^{21}$ each independently represent an organic group. The organic group is exemplified by an alkyl group, an aryl group, a group obtained by linking a plurality of alkyl groups and/or aryl groups, and the like. The organic group is preferably an alkyl group substituted with a fluorine atom or a fluoroalkyl group in 1-position, or a phenyl group substituted with a fluorine atom or a fluoroalkyl group. When the organic group includes the fluorine atom or the fluoroalkyl group, the acidity of the acid generated upon the exposure tends to increase, leading to an improvement of the sensitivity. However, it is preferred that the organic group does not include the fluorine atom as the substituent at an end thereof.

The acid anion preferably includes at least one anion group selected from the group consisting of a sulfonic acid anion, a carboxylic acid anion, a sulfonylimide anion, a bis(alkylsulfonyl)imide anion, and a tris(alkylsulfonyl)methide anion. The acid anion is exemplified by an anion represented by the general formula "$R^{22}$—$SO_3^-$", wherein $R^{22}$ represents a linear, branched or cyclic alkyl group, a halogenated alkyl group, an aryl group, or an alkenyl group, wherein the linear, branched or cyclic alkyl group, the halogenated alkyl group, the aryl group and the alkenyl group may have a substituent. The number of carbon atoms of the linear or branched alkyl group which may be represented by $R^{22}$ is preferably no less than 1 and no greater than 10. In a case where $R^{22}$ represents the linear, branched or cyclic alkyl group which may have a substituent, for example, the acid anion is exemplified by alkylsulfonates such as methanesulfonate, n-propanesulfonate, n-butanesulfonate and n-octanesulfonate, 1-adamantanesulfonate, 2-norbornanesulfonate, d-camphor-10-sulfonate, and the like. The halogenated alkyl group which may be represented by $R^{22}$ is a group obtained by substituting a part or all of hydrogen atoms of the alkyl group with a halogen atom, and the number of carbon atoms of the alkyl group is preferably no less than 1 and no greater than 10. Among the alkyl groups, linear or branched alkyl groups are more preferred, and a methyl group, an ethyl group, a propyl group, an isopropyl group, a n-butyl group, a tert-butyl group, a tert-pentyl group, and an isopentyl group are still more preferred. Moreover, examples of the halogen atom substituting the hydrogen atom include a fluorine atom, a chlorine atom, an iodine atom, a bromine atom, and the like. In regard to the halogenated alkyl group, it is preferred that no less than 50% and no greater than 100% of the total number of hydrogen atoms included in the alkyl group (alkyl group in its unhalogenated state) are substituted by the halogen atom, and it is more preferred that all hydrogen atoms are substituted by the halogen atom. In this regard, the halogenated alkyl group is preferably a fluorinated alkyl group. The number of carbon atoms of the fluorinated alkyl group is preferably no less than 1 and no greater than 10, more preferably no less than 1 and no greater than 8, and most preferably no less than 1 and no greater than 4. In addition, the degree of fluorination of the fluorinated alkyl group is preferably no less than 10% and no greater than 100%, and more preferably no less than 50% and no greater than 100%, and in particular, all of the hydrogen atoms are preferably substituted by the fluorine atom in light of an increase of the strength of the acid. Examples of the preferred fluorinated alkyl group include a trifluoromethyl group, a heptafluoro-n-propyl group, a nonafluoro-n-butyl group, and the like.

$R^{22}$ may have a substituent. The substituent includes a divalent linking group that has an oxygen atom. The linking group is exemplified by non-hydrocarbon, oxygen atom-containing linking groups such as an oxygen atom (ether linkage: —O—), an ester linkage (—C(=O)—O—), an amide linkage (—C(=O)—NH—), a carbonyl group (—C(=O)—), a sulfonyl group (—SO$_2$—), and a carbonate linkage (—O—C(=O)—O—).

Examples of the acid anion include, but not limited to, anions represented by the following formulae.

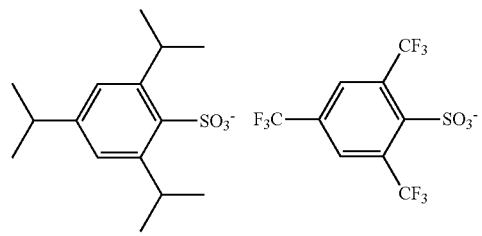

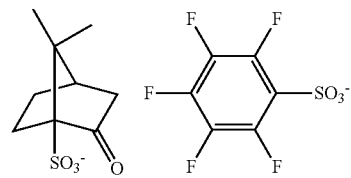

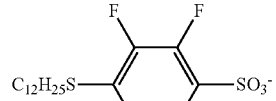

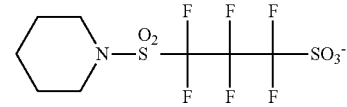

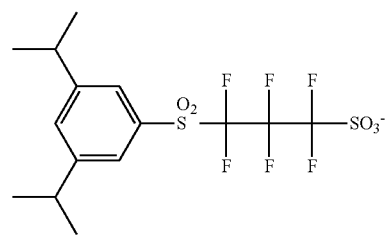

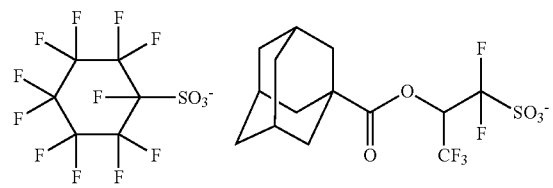

-continued

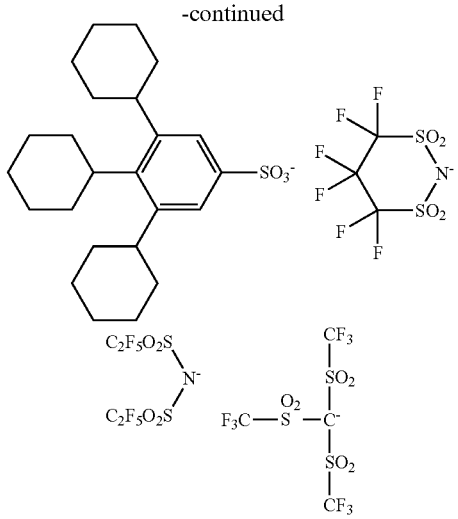

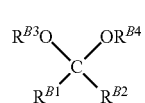

The radiation-sensitive acid-and-sensitizer generating agent (a) may be a part of the polymer constituting the polymer component (1). In this case, the radiation-sensitive acid-and-sensitizer generating agent (a) is present in the form of a group obtained by eliminating one hydrogen atom from the aforementioned compound and bound to the polymer.

In the case where the radiation-sensitive acid-and-sensitizer generating agent (a) is the component different from the polymer component (1), the lower limit of the content of the radiation-sensitive acid-and-sensitizer generating agent (a) with respect to 100 parts by mass of the polymer component (1) is preferably 0.005 parts by mass, and more preferably 0.1 parts by mass. On the other hand, the upper limit of the content of the radiation-sensitive acid-and-sensitizer generating agent (a) is preferably 50 parts by mass, and more preferably 30 parts by mass.

In the case where the radiation-sensitive acid-and-sensitizer generating agent (a) is a part of the polymer constituting the polymer component (1), the proportion of the radiation-sensitive acid-and-sensitizer generating agent (a) contained with respect to 1 mol of the polymer component (1) is preferably 0.001 mol, more preferably 0.002 mol, and still more preferably 0.01 mol. On the other hand, the upper limit of the proportion of the radiation-sensitive acid-and-sensitizer generating agent (a) is preferably 0.5 mol, and more preferably 0.3 mol.

When the content or the proportion of the radiation-sensitive acid-and-sensitizer generating agent (a) contained is less than the lower limit, the sensitivity may be deteriorated. To the contrary, when the content or the proportion of the radiation-sensitive acid-and-sensitizer generating agent (a) contained is greater than the upper limit, it may be difficult to form the resist film, and/or the rectangularity of the cross-sectional shape of the resist pattern may be deteriorated.

(b) Radiation-Sensitive Sensitizer Generating Agent

The radiation-sensitive sensitizer generating agent (b) is a component that is capable of generating, upon the irradiation with the first radioactive ray, the radiation-sensitive sensitizer that absorbs the second radioactive ray, but the radiation-sensitive sensitizer generating agent substantially does not generate the radiation-sensitive sensitizer upon the irradiation with the second radioactive ray without the irradiation with the first radioactive ray, and the radiation-sensitive sensitizer generating agent (b) is different from the radiation-sensitive acid-and-sensitizer generating agent (a).

(B) Compound

The radiation-sensitive sensitizer generating agent (b) includes the compound (B) represented by the following formula (B):

$$R^{B3}O\diagdown_{\underset{R^{B1}}{C}\diagup}^{\diagup OR^{B4}}\diagdown R^{B2} \tag{B}$$

In the above formula (B), $R^{B1}$ and $R^{B2}$ each independently represent a hydrogen atom, a halogen atom, an amino group or a monovalent organic group that bonds to the carbon atom to which $R^{B3}O$ and $R^{B4}O$ bond via a carbon atom, or $R^{B1}$ and $R^{B2}$ taken together represent a cyclic structure having 3 to 30 ring atoms together with the carbon atom to which $R^{B1}$ and $R^{B2}$ bond; and $R^{B3}$ and $R^{B4}$ each independently represent a monovalent organic group having 1 to 20 carbon atoms, or $R^{B3}$ and $R^{B4}$ taken together represent a cyclic structure having 4 to 30 ring atoms together with O—C—O to which $R^{B3}$ and $R^{B4}$ bond, wherein at least one of $R^{B3}$ and $R^{B4}$ includes a halogen atom, a nitro group, a cyano group, a formyl group, a carbonyl group, a carboxy group, a sulfo group, a sulfonyl group or a combination thereof, or the cyclic structure having 4 to 30 ring atoms is a spiro cyclic structure, a fused cyclic structure or a bridged cyclic structure.

According to the chemically amplified resist material, the chemical structure of the radiation-sensitive sensitizer generating agent (b) is altered through a direct or indirect reaction upon the irradiation with the first radioactive ray to generate a radiation-sensitive sensitizer that assists in the generation of the acid upon the irradiation with the second radioactive ray. Since the radiation-sensitive sensitizer absorbs the second radioactive ray more readily as compared with the radiation-sensitive sensitizer generating agent (b), the absorption capacity with respect to the second radioactive ray differs significantly upon the patternwise exposure with the first radioactive ray between the light-exposed regions where the radiation-sensitive sensitizer is generated and the patternwise unexposed regions where the radiation-sensitive sensitizer is not generated, whereby a contrast of the absorption capacity can be attained more easily.

By virtue of the radiation-sensitive sensitizer generating agent (b) including the compound (B), the chemically amplified resist material enables both sensitivity and lithography performances to be attained at a high level in a case where the radioactive ray having a wavelength of no greater than 250 nm such as EUV, an electron beam, a KrF excimer laser beam and an ArF excimer laser beam is used as patterning exposure light. Although the reason for achieving the aforementioned effect by the chemically amplified resist material owing to having the above-described constitution is not clear, the reason may be be inferred as follows, for example. When $R^{B3}$ and $R^{B4}$ in the above formula (B) represent the specified electron-withdrawing group such as a halogen atom, a nitro group, a cyano group, a formyl group, a carbonyl group, a carboxy group, a sulfo group, a sulfonyl group or a combination thereof, or $R^{B3}$ and $R^{B4}$ may taken together represent a spiro cyclic structure, a fused cyclic structure or a bridged cyclic structure, adequately high activation energy required for cleavage of the acetal structure of the compound (B) is enabled. Therefore, according to the chemically amplified resist material, the acid generated from the radiation-sensitive acid-and-sensitizer generating agent (a) and/or the radiation-sensitive acid generating agent (c) in the patternwise exposed region transfer(s) to the patternwise unexposed region, whereby generation of the radiation-sensitive sensitizer in the patternwise unexposed region can be inhibited even if a small amount of the acid is present in the patternwise unexposed region. Moreover, the specified electron-withdrawing groups such as a halogen atom which may be involved in $R^{B3}$ and $R^{B4}$ in the above formula (B) are, unlike ester groups and the like, those which are less likely to be hydrolyzed by the acid. Thus, even in the case where $R^{B3}$ and $R^{B4}$ involves the above-specified electron-withdrawing group, competition of the cleavage of the acetal structure with the hydrolysis of the specified electron-withdrawing group can be inhibited. Consequently, the chemically amplified resist material is believed to be superior in the sensitivity and lithography performances.

Examples of the halogen atom which may be represented by $R^{B1}$ and $R^{B2}$ include a fluorine atom, a chlorine atom, a bromine atom, an iodine atom, and the like.

The monovalent organic group which may be represented by $R^{B1}$ and $R^{B2}$ is exemplified by groups similar to those exemplified above in connection with $R^{F6}$, $R^{F12}$, $R^{F13}$, $R^{F14}$ and $R^{F15}$, and the like.

Exemplary cyclic structures having 3 to 30 ring atoms which may be taken together represented by $R^{B1}$ and $R^{B2}$ together with the carbon atom to which $R^{B1}$ and $R^{B2}$ bond include an alicyclic structure having 3 to 20 ring atoms, an aliphatic heterocyclic structure having 3 to 20 ring atoms, an aromatic cyclic structure having 6 to 20 ring atoms, an aromatic heterocyclic structure having 5 to 20 ring atoms, and the like. These cyclic structures may be a spiro cyclic structure, a fused cyclic structure or a bridged cyclic structure.

The alicyclic structure having 3 to 20 ring atoms is exemplified by structures similar to those exemplified above in connection with $R^{A3}$ and $R^{A4}$, and the like.

Examples of the aliphatic heterocyclic structure having 3 to 20 ring atoms include:

lactone structures such as a hexanolactone structure and a norbornanelactone structure;

sultone structures such as a hexanosultone structure and a norbornanesultone structure;

oxygen atom-containing heterocyclic structures such as an oxacycloheptane structure and an oxanorbornane structure;

nitrogen atom-containing heterocyclic structures such as an azacyclohexane structure and a diazabicyclooctane structure;

sulfur atom-containing heterocyclic structures such as a thiacyclohexane structure and a thianorbornane structure; and the like.

Examples of the aromatic cyclic structure having 6 to 20 ring atoms include a benzene structure, a naphthalene structure, a phenanthrene structure, an anthracene structure and the like.

Examples of the aromatic heterocyclic structure having 5 to 20 ring atoms include: oxygen atom-containing heterocyclic structures such as a furan structure, a pyran structure and a benzopyran structure; nitrogen atom-containing heterocyclic structures such as a pyridine structure, a pyrimidine structure and an indole structure; and the like.

It is preferred that $R^{B1}$ and $R^{B2}$ each represent: a hydrogen atom, a halogen atom, an amino group, a phenyl group, a naphthyl group, an anthracenyl group, an alkoxy group having 1 to 5 carbon atoms, an alkylthio group having 1 to 5 carbon atoms, a phenoxy group, a naphthoxy group, an anthracenoxy group, an amide group, an unsaturated hydrocarbon group having 1 to 30 carbon atoms, or a carbonyl group to which an alkyl group having 1 to 12 carbon atoms bonds; or a group obtained by substituting at least a part of hydrogen atoms included in the phenyl group, the naphthyl group, the anthracenyl group, the alkoxy group, the alkylthio group, the phenoxy group, the naphthoxy group, the anthracenoxy group or the unsaturated hydrocarbon group, or that $R^{B1}$ and $R^{B2}$ taken together represent a cyclic structure together with the carbon atom to which $R^{B1}$ and $R^{B2}$ are linked via a single bond, a double bond, or a bond that includes any one of —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH— and —$NR^g$—, wherein $R^g$ represents: a phenyl group; a phenoxy group; a halogen atom; a saturated or unsaturated linear, branched or cyclic hydrocarbon group having 1 to 30 carbon atoms; an alkoxy group having 1 to 5 carbon atoms, a hydroxy group or a phenoxy group substituted with an alkyl group having 1 to 5 carbon atoms; or a saturated or unsaturated linear, branched or cyclic hydrocarbon group having 1 to 30 carbon atoms, or a phenyl group substituted with an alkoxy group having 1 to 5 carbon atoms or a hydroxy group. Examples of the substituent include groups similar to those exemplified above in connection with $R^{F5}$ and $R^{F8}$, and the like.

$R^{B1}$ and $R^{B2}$ each represent more preferably a phenyl group substituted with an alkoxy group having 1 to 5 carbon atoms or an alkyl group having 1 to 5 carbon atoms, still more preferably a phenyl group substituted with an alkoxy group having 1 to 3 carbon atoms, and particularly preferably a phenyl group substituted with a methoxy group. In addition, it is preferred that $R^{B1}$ and $R^{B2}$ are the same.

The monovalent organic group which may be represented by $R^{B3}$ and $R^{B4}$ is exemplified by groups similar to those exemplified above in connection with $R^{F6}$, $R^{F12}$, $R^{F13}$, $R^{F14}$ and $R^{F15}$, and the like.

Examples of the cyclic structure having 4 to 30 ring atoms which may be taken together represented by $R^{B3}$ and $R^{B4}$ together with O—C—O to which $R^{B3}$ and $R^{B4}$ bond include: monocyclic structures such as a 1,3-dioxolane structure, a 1,3-dioxane structure and a 1,3-dioxepane structure; polycyclic structures such as a spiro cyclic structure, a fused cyclic structure and a bridged cyclic structure constructed by the monocyclic structure and other cyclic structure, and the like.

The number of the ring atoms of the monocyclic structure is preferably 5 and 6, and more preferably 5. The cyclic structure is preferably a 1,3-dioxolane structure and a 1,3-dioxane structure, and more preferably a 1,3-dioxolane structure.

It is preferred that the compound (B) is constructed by $R^{B1}$—C—$R^{B2}$ in the above formula (B), and has a partial structure represented by the following formulae (XXVII) to (XXX).

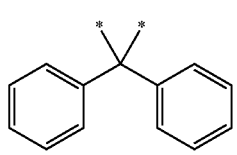

(XXVII)

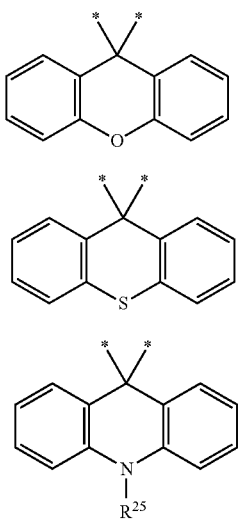

(XXVIII)

(XXIX)

(XXX)

In the above formulae (XXVII) to (XXX), * denotes a site of binding to $OR^{B3}$ or $OR^{B4}$ of the above formula (B). In the above formulae (XXVII) to (XXX), hydrogen atom(s) of the aromatic ring may be substituted by an alkoxy group having 1 to 5 carbon atoms or an alkyl group having 1 to 5 carbon atoms, and the aromatic ring may bind to other aromatic ring to form a naphthalene ring or an anthracene ring. $R^{25}$ represents an alkyl group having 1 to 5 carbon atoms.

The compound (B) thus having the partial structure represented by the above formulae (XXVII) to (XXX) enables the shift of the absorption wavelength of the radioactive ray between the radiation-sensitive sensitizer generating agent (b) and the radiation-sensitive sensitizer generated from the radiation-sensitive sensitizer generating agent (b) to be increased, and as a result, the compound (B) can cause a sensitization reaction selectively in patternwise exposed regions.

The partial structure is preferably a partial structure represented by the above formula (XXVII), and more preferably a partial structure represented by the following formula.

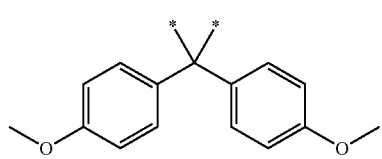

The compound (B) is exemplified by a compound represented by the above formula (B), wherein at least one of $R^{B3}$ and $R^{B4}$ includes a halogen atom, a nitro group, a cyano group, a formyl group, a carbonyl group, a carboxy group, a sulfo group, a sulfonyl group or a combination thereof (hereinafter, may be also referred to as "(B1) compound" or "compound (B1)"), and the like. It is considered that when an organic group that includes the electron-withdrawing group such as a halogen atom bonds to at least one of the oxygen atom constituting the acetal structure in the compound (B1), the activation energy required for cleavage can be adequately increased.

In the case where $R^{B3}$ and $R^{B4}$ in the compound (B1) taken together represent a cyclic structure, the cyclic structure is preferably a monocyclic structure.

The group included in $R^{B3}$ and $R^{B4}$ is preferably a nitro group and a sulfonyl group. In addition, is preferred that $R^{B3}$ and $R^{B4}$ are the same.

Examples of the compound (B1) include compounds represented by the following formulae, and the like.

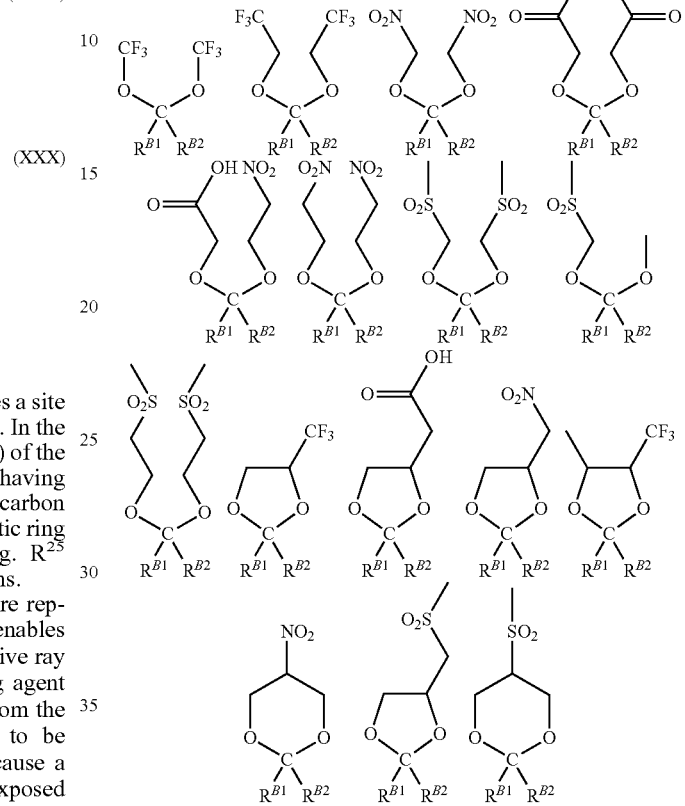

In the above formulae, $R^{B1}$ and $R^{B2}$ are as defined in the above formula (B).

Examples of preferred compound (B1) include compounds represented by the following formulae.

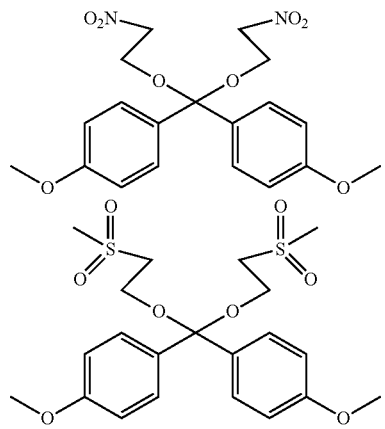

The compound (B) is also exemplified by a compound represented by the following formula (B-I) or formula (B-II) (hereinafter, may be also referred to as "(B2) compound" or "compound (B2)"), and the like. The compound (B2) corresponds to a compound represented by the above formula (B), wherein $R^{B3}$ and $R^{B4}$ taken together represent a cyclic structure having 4 to 30 ring atoms together with O—C—O to which $R^{B3}$ and $R^{B4}$ bond, wherein the cyclic structure having 4 to 30 ring atoms is a spiro cyclic structure, a fused cyclic structure or a bridged cyclic structure. It is considered that when O—C—O in the acetal structure constructs the spiro cyclic structure, fused cyclic structure or bridged cyclic structure together with $R^{B3}$ and $R^{B4}$ in the compound (B2), the activation energy required for cleavage can be adequately increased.

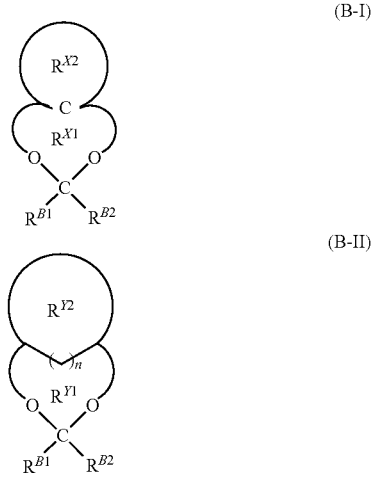

In the above formula (B-I) and formula (B-II), $R^{B1}$ and $R^{B2}$ are as defined in the above formula (B).

In the above formula (B-I), $R^{X1}$ represents a group having a monocyclic structure having 4 to 20 ring atoms; and $R^{X2}$ represents a group having a cyclic structure having 3 to 20 ring atoms.

In the above formula (B-II), $R^{Y1}$ represents a group having a monocyclic structure having 5 to 20 ring atoms; $R^{Y2}$ represents a group having a cyclic structure having 3 to 20 ring atoms; and n is an integer of 0 to 3.

$R^{X1}$, $R^{X2}$, $R^{Y1}$ and $R^{Y2}$ may have one or a plurality of substituent(s). The substituent may be either an electron-withdrawing group or an electron-donating group, and examples of the substituent include a hydrocarbon group having 1 to 10 carbon atoms, an oxyhydrocarbon group having 1 to 10 carbon atoms, a hydroxy group, an amino group, a carboxy group, a nitro group, a cyano group, an amino group, and the like.

The monocyclic structure having 4 to 20 ring atoms included in $R^{X1}$ is exemplified by a monocyclic aliphatic heterocyclic structure having 4 to 20 ring atoms, and the like. The monocyclic aliphatic heterocyclic structure having 4 to 20 ring atoms is exemplified by those having a monocyclic structure among the aliphatic heterocyclic structures exemplified above in connection with $R^{B1}$ and $R^{B2}$, and the like. The number of the ring atoms of the monocyclic structure is preferably 5 and 6, and more preferably 5. The monocyclic structure is preferably a 1,3-dioxolane structure and a 1,3-dioxane structure, and more preferably a 1,3-dioxolane structure.

The cyclic structure having 3 to 20 ring atoms included in $R^{X2}$ may be either monocyclic or polycyclic. The cyclic structure having 3 to 20 ring atoms included in $R^{X2}$ is exemplified by an alicyclic structure having 3 to 20 ring atoms, an aliphatic heterocyclic structure having 3 to 20 ring atoms, and the like. Examples of the alicyclic structure having 3 to 20 ring atoms include structures similar to those exemplified above in connection with $R^{A3}$ and $R^{A4}$, and the like. Examples of the aliphatic heterocyclic structure having 3 to 20 ring atoms include structures similar to those exemplified above in connection with $R^{B1}$ and $R^{B2}$, and the like. The number of the ring atoms of the cyclic structure included in $R^{X2}$ is preferably 5 and 6. The cyclic structure included in $R^{X2}$ is preferably an alicyclic structure, more preferably a cyclopentane structure and a cyclohexane structure, and still more preferably a cyclopentane structure.

The monocyclic structure having 5 to 20 ring atoms included in $R^{Y1}$ is exemplified by a monocyclic aliphatic heterocyclic structure having 5 to 20 ring atoms, and the like. The monocyclic aliphatic heterocyclic structure having 5 to 20 ring atoms is exemplified by those having a monocyclic structure among the aliphatic heterocyclic structures exemplified above in connection with $R^{B1}$ and $R^{B2}$, and the like. The number of the ring atoms of the monocyclic structure included in $R^{Y1}$ is preferably 5 and 6, and more preferably 5. The monocyclic structure included in $R^{Y1}$ is preferably a 1,3-dioxolane structure and a 1,3-dioxane structure, and more preferably a 1,3-dioxolane structure.

The cyclic structure having 3 to 20 ring atoms included in $R^{Y2}$ may be either monocyclic or polycyclic. The cyclic structure having 3 to 20 ring atoms included in $R^{Y2}$ is exemplified by an alicyclic structure having 3 to 20 ring atoms, an aliphatic heterocyclic structure having 3 to 20 ring atoms, an aromatic cyclic structure having 6 to 20 ring atoms, an aromatic heterocyclic structure having 5 to 20 ring atoms, and the like. Examples of the alicyclic structure having 3 to 20 ring atoms include structures similar to those exemplified above in connection with $R^{A3}$ and $R^{A4}$, and the like. Examples of the aliphatic heterocyclic structure having 3 to 20 ring atoms, the aromatic cyclic structure having 6 to 20 ring atoms and the aromatic heterocyclic structure having 5 to 20 ring atoms include structures similar to those exemplified above in connection with $R^{B1}$ and $R^{B2}$, and the like. The number of the ring atoms of the cyclic structure included in $R^{Y2}$ is preferably 5 and 6. The cyclic structure included in $R^{Y2}$ is preferably an alicyclic structure, and more preferably a cyclohexane structure and a norbornane structure.

In the above formula, n is preferably an integer of 0 to 2, 0 and more preferably 1.

Among candidate compounds (B2), examples of the compound represented by the above formula (B-I) include compounds represented by the following formulae, and the like.

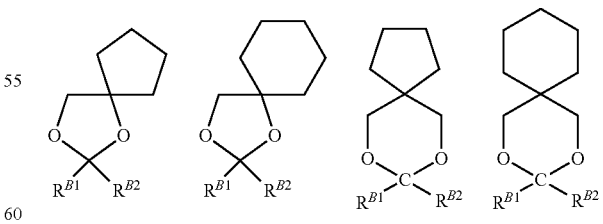

In the above formulae, $R^{B1}$ and $R^{B2}$ are as defined in the above formula (B).

Among candidate compounds (B2), examples of the compound represented by the above formula (B-II) include compounds represented by the following formulae, and the like.

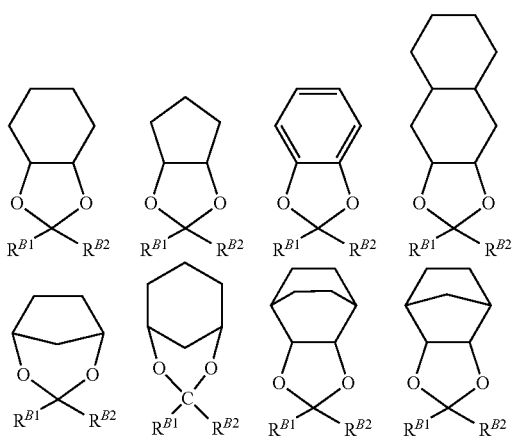

In the above formulae, $R^{B1}$ and $R^{B2}$ are as defined in the above formula (B).

The compound (B-2) is preferably represented by any one of the following formulae.

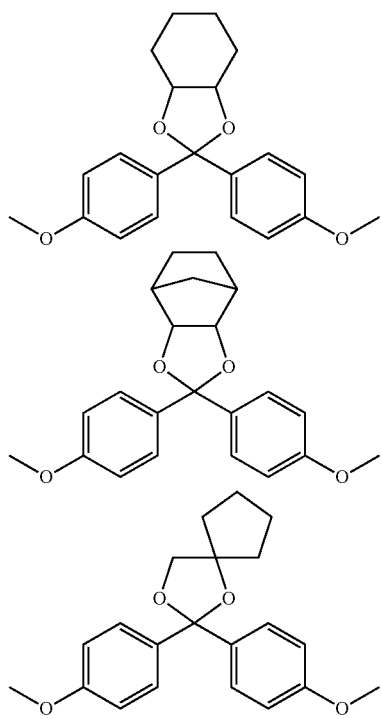

The radiation-sensitive sensitizer generating agent (b) may further include a well-known radiation-sensitive sensitizer generating agent in addition to the compound (B). In this case, the lower limit of the proportion of the compound (B) in the radiation-sensitive sensitizer generating agent (b) is preferably 60 mol %, and more preferably 70 mol %. When the proportion of the compound (B) is less than the lower limit, the sensitivity of the chemically amplified resist material may not be sufficiently improved. Also, the proportion of the compound (B) may be 100 mol %.

Alternatively, the radiation-sensitive sensitizer generating agent (b) may be a part of the polymer constituting the polymer component (1). In this case, the radiation-sensitive sensitizer generating agent (b) is present in the form of a group obtained by eliminating one hydrogen atom from the compound (B) or the like.

In the case where the radiation-sensitive sensitizer generating agent (b) is the component different from the polymer component (1), the lower limit of the content of the radiation-sensitive sensitizer generating agent (b) with respect to 100 parts by mass of the polymer component (1) is preferably 0.1 parts by mass, more preferably 1 part by mass, and still more preferably 4 parts by mass. On the other hand, the upper limit of the content of the radiation-sensitive sensitizer generating agent (b) is preferably 50 parts by mass, more preferably 30 parts by mass, and still more preferably 15 parts by mass.

In the case where the radiation-sensitive sensitizer generating agent (b) is a part of the polymer constituting the polymer component (1), the proportion of the radiation-sensitive acid-and-sensitizer generating agent (a) contained with respect to 1 mol of the polymer component (1) is preferably 0.001 mol, more preferably 0.002 mol, and still more preferably 0.01 mol. On the other hand, the upper limit of the proportion of the radiation-sensitive sensitizer generating agent (b) is preferably 0.95 mol, and more preferably 0.3 mol.

When the content or the proportion of the radiation-sensitive sensitizer generating agent (b) is less than the lower limit, the sensitivity may be deteriorated. To the contrary, when the content or the proportion of the radiation-sensitive sensitizer generating agent (b) is greater than the upper limit, it may be difficult to form the resist film, and/or the rectangularity of the cross-sectional shape of the resist pattern may be deteriorated.

Radiation-Sensitive Sensitizer

The radiation-sensitive sensitizer can be generated from the radiation-sensitive acid-and-sensitizer generating agent (a) and the radiation-sensitive sensitizer generating agent (b) upon the irradiation with the first radioactive ray, and is capable of degrading the radiation-sensitive acid generating agent (c) (for example, photoacid generating agent: PAG) through absorbing the second radioactive ray.

Examples of the radiation-sensitive sensitizer include chalcone, 1,2-diketone, benzoin, benzophenone, fluorene, naphthoquinone, anthraquinone, xanthene, thioxanthene, xanthone, thioxanthone, cyanine, merocyanine, naphthalocyanine, subphthalocyanine, pyrylium, thiopyrylium, tetraphylline, annulene, spiropyran, spirooxazine, thiospiropyran, oxole, azine, thiazine, oxazine, indoline, azulene, azulenium, squarylium, porphyrin, porphyrazine, triarylmethane, phthalocyanine, acridone, coumarin, ketocoumarin, quinolinone, benzoxazole, acridine, thiazine, benzothiazole, phenothiazine, benzotriazole, perylene, naphthalene, anthracene, phenanthrene, pyrene, naphthacene, pentacene, coronene and derivatives of these, and the like.

Also, the radiation-sensitive sensitizer preferably contains a carbonyl compound. The carbonyl compound preferably contains ketone, aldehyde, carboxylic acid, ester, amide, enone, carboxylic acid chloride or carboxylic anhydride, as a carbonyl group. The carbonyl compound may be exemplified by a benzophenone derivative, a xanthone derivative, a thioxanthone derivative, a coumarin derivative, and an acridone derivative. Alternatively, the carbonyl compound may be a naphthalene derivative or an anthracene derivative, or may also be an acridone derivative.

Furthermore, it is preferred that at least one hydrogen atom in the aromatic ring included in the radiation-sensitive sensitizer is substituted with an electron-donating group.

Substitution of hydrogen atom with an electron-donating group tends to improve electron transfer efficiency by the sensitization reaction in the floodwise exposure step described later, and thus improve sensitivity of the chemically amplified resist material. In addition, an increase in the difference can be made between the absorption wavelength of the radioactive ray that can be absorbed by the radiation-sensitive sensitizer, and the absorption wavelength of the radioactive ray that can be absorbed by the radiation-sensitive acid-and-sensitizer generating agent (a) and the radiation-sensitive sensitizer (b), whereby the radiation-sensitive sensitizer can be excited more selectively in the floodwise exposure step. As a result, contrast of the latent image of the acid in the chemically amplified resist material can be improved. Examples of the electron-donating group include a hydroxyl group, a methoxy group, an alkoxy group, an amino group, an alkylamino group, and an alkyl group.

Examples of the radiation-sensitive sensitizer include acetophenone, 2,2-dimethoxy-2-phenylacetophenone, diethoxyacetophenone, 1-hydroxycyclohexyl phenyl ketone, 1,2-hydroxy-2-methyl-1-phenylpropan-1-one, α-hydroxycyclohexyl phenyl ketone, 2-hydroxy-2-methyl-1-phenylpropanone, 2-hydroxy-2-methyl-1-(4-isopropylphenyl)propanone, 2-hydroxy-2-methyl-1-(4-dodecylphenyl) propanone, 2-hydroxy-2-methyl-1-[(2-hydroxyethoxy)phenyl]propanone, benzophenone, 2-methylbenzophenone, 3-methylbenzophenone, 4-methylbenzophenone, 4-methoxybenzophenone, 2-chlorobenzophenone, 4-chlorobenzophenone, 4-bromobenzophenone, 2-carboxybenzophenone, 2-ethoxycarbonylbenzophenone, 4-benzoyl-4'-methyldiphenyl sulfide, benzophenonetetracarboxylic acid or the tetramethyl ester thereof, 4,4'-bis(dimethylamino) benzophenone, 4,4'-bis(dicyclohexylamino)benzophenone, 4,4'-bis(diethylamino)benzophenone, 4,4'-bis(dihydroxyethylamino)benzophenone, 4-methoxy-4'-dimethylaminobenzophenone, 4,4'-dimethoxybenzophenone, 4-dimethylaminobenzophenone, 4-dimethylaminoacetophenone, benzil, anthraquinone, 2-t-butylanthraquinone, 2-methylanthraquinone, phenanthraquinone, fluorenone, 2-benzyl-2-dimethylamino-1-(4-morpholinophenyl)-1-butanone, 2-(dimethylamino)-2-[(4-methylphenyl)methyl]-1-[4-(4-morpholinyl)phenyl]-1-butanone, 2-methyl-1-[4-(methylthio)phenyl]-2-morpholino-1-propanone, 2-hydroxy-2-methyl-[4-(1-methylvinyl)phenyl]propanol oligomer, benzoin, benzoin methyl ether, benzoin ethyl ether, benzoin propyl ether, benzoin isopropyl ether, benzoin isobutyl ether, benzoin phenyl ether, benzil dimethyl ketal, acridone, chloroacridone, N-methylacridone, N-butylacridone, N-butyl-chloroacridone, 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, 2-isopropylthioxanthone, 4-isopropylthioxanthone, 2,4-diethylthioxanthone, 2,4-dichlorothioxanthone, 1-chloro-4-propoxythioxanthone, benzoyl di-(2,6-dimethylphenyl)phosphonate, 1-[4-(phenylthio)phenyl]-1,2-octanedione-2-(O-benzoyloxime), 1-[9-ethyl-6-(2-methylbenzoyl)-9H-carbazol-3-yl]ethanone-1-(O-acetyloxime), 1-[9-ethyl-6-(2-methylbenzoyl)-9H-carbazol-3-yl]-3-cyclopentylpropanone-1-(O-acetyloxime), 1-[4-(phenylthio)phenyl]-3-cyclopentylpropane-1,2-dione-2-(O-benzoyloxime), 2,2-dimethoxy-1,2-diphenylethan-1-one, 1-[4-(2-hydroxyethoxy)-phenyl]-2-hydroxy-2-methyl-1-propan-1-one, 2-hydroxy-1-{4-[4-(2-hydroxy-2-methylpropionyl)-benzyl]phenyl}-2-methyl-propan-1-one, phenylglyoxylic acid methyl ester, 2-methyl-1-(4-methylthiophenyl)-2-morpholinopropan-1-one, 2-benzyl-2-dimethylamino-1-(4-morpholinophenyl)-butanone-1, 1-[4-(phenylthio)phenyl]-1,2-octanedione 2-(O-benzoyloxime)], 1-[9-ethyl-6-(2-methylbenzoyl)-9H-carbazol-3-yl]ethanone 1-(O-acetyloxime), and the like.

(c) Radiation-Sensitive Acid Generating Agent

The radiation-sensitive acid generating agent (c) is a component that is capable of generating the acid upon the irradiation with the first radioactive ray, but substantially does not generate the acid upon the irradiation with the second radioactive ray without the irradiation with the first radioactive ray, and is different from the radiation-sensitive acid-and-sensitizer generating agent (a).

The radiation-sensitive acid generating agent (c) is exemplified by an onium salt compound, a N-sulfonyloxyimide compound, a sulfonimide compound, a halogen-containing compound, a diazoketone compound, and the like.

Examples of the onium salt compound include a sulfonium salt, a tetrahydrothiophenium salt, an iodonium salt, a phosphonium salt, a diazonium salt, a pyridinium salt, and the like.

Specific examples of the radiation-sensitive acid generating agent (c) include compounds disclosed in paragraphs [0080] to [0113] of Japanese Unexamined Patent Application, Publication No. 2009-134088, and the like.

The radiation-sensitive acid generating agent (c) is preferably an acid generating agent represented by the following formula (c). The radiation-sensitive acid generating agent (c) having the following structure is considered to appropriately diminish the diffusion length of the acid, which had been generated in the patternwise exposure step described later, in the resist film by way of the interaction with the structural unit (I) or structural unit (IV) in the polymer (A). As a result, performances of the chemically amplified resist material, such as depth of focus, etc., can be improved.

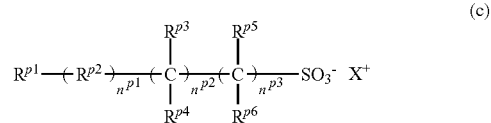

(c)

In the above formula (c), $R^{p1}$ represents a monovalent group that includes a cyclic structure having 6 or more ring atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; $n^{p1}$ is an integer of 0 to 10; $n^{p2}$ is an integer of 0 to 10; $n^{p3}$ is an integer of 1 to 10, wherein in a case where $n^{p1}$ is no less than 2, a plurality of $R^{p2}$s may be identical or different, wherein in a case where $n^{p2}$ is no less than 2, a plurality of $R^{p3}$s may be identical or different, and a plurality of $R^{p4}$s may be identical or different, and wherein in a case where $n^{p3}$ is no less than 2, a plurality of $R^{p5}$s may be identical or different, and a plurality of $R^{p6}$s may be identical or different; and $X^+$ represents a monovalent radiation-sensitive onium cation.

The monovalent group that includes a cyclic structure having 6 or more ring atoms, which is represented by $R^{p1}$ is exemplified by a monovalent group that includes an alicyclic structure having 6 or more ring atoms, a monovalent group that includes an aliphatic heterocyclic structure having 6 or more ring atoms, a monovalent group that includes an aromatic cyclic structure having 6 or more ring atoms, a monovalent group that includes an aromatic heterocyclic structure having 6 or more ring atoms, and the like.

Examples of the alicyclic structure having 6 or more ring atoms include:

monocyclic cycloalkane structures such as a cyclohexane structure, a cycloheptane structure, a cyclooctane structure, a cyclononane structure, a cyclodecane structure and a cyclododecane structure;

monocyclic cycloalkene structures such as a cyclohexene structure, a cycloheptene structure, a cyclooctene structure and a cyclodecene structure;

polycyclic cycloalkane structures such as a norbornane structure, an adamantane structure, a tricyclodecane structure and a tetracyclododecane structure;

polycyclic cycloalkene structures such as a norbornene structure and a tricyclodecene structure; and the like.

Examples of the aliphatic heterocyclic structure having 6 or more ring atoms include:

lactone structures such as a hexanolactone structure and a norbornanelactone structure;

sultone structures such as a hexanosultone structure and a norbornanesultone structure;

oxygen atom-containing heterocyclic structures such as an oxacycloheptane structure and an oxanorbornane structure;

nitrogen atom-containing heterocyclic structures such as an azacyclohexane structure and a diazabicyclooctane structure;

sulfur atom-containing heterocyclic structures such as a thiacyclohexane structure and a thianorbornane structure; and the like.

Examples of the aromatic cyclic structure having 6 or more ring atoms include: a benzene structure, a naphthalene structure, a phenanthrene structure, an anthracene structure and the like.

Examples of the aromatic heterocyclic structure having 6 or more ring atoms include: oxygen atom-containing heterocyclic structures such as a pyran structure and a benzopyran structure; nitrogen atom-containing heterocyclic structures such as a pyridine structure, a pyrimidine structure and an indole structure; and the like.

The lower limit of the number of ring atoms of the cyclic structure in $R^{p1}$ is preferably 7, more preferably 8, still more preferably 9, and particularly preferably 10. On the other hand, the upper limit of the number of ring atoms of the cyclic structure in $R^{p1}$ is preferably 15, more preferably 14, still more preferably 13, and particularly preferably 12. When the number of ring atoms falls within the above range, the abovementioned diffusion length of the acid can be decreased further moderately, and consequently various types of performances of the chemically amplified resist material can be further improved.

A part or all of hydrogen atoms included in the cyclic structure in $R^{p1}$ may be substituted with a substituent. Examples of the substituent include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, a hydroxy group is preferred.

Of these, $R^{p1}$ represents preferably a monovalent group that includes an alicyclic structure having 6 or more ring atoms or a monovalent group that includes an aliphatic heterocyclic structure having 6 or more ring atoms, more preferably a monovalent group that includes an alicyclic structure having 9 or more ring atoms or a monovalent group that includes an aliphatic heterocyclic structure having 9 or more ring atoms, still more preferably an adamantyl group, a hydroxyadamantyl group, a norbornanelacton-yl group, a norbornanesultone-yl group or a 5-oxo-4-oxatricyclo [4.3.1.1$^{3,8}$]undecan-yl group, and particularly preferably an adamantyl group.

Examples of the divalent linking group represented by $R^{p2}$ include a carbonyl group, an ether group, a carbonyloxy group, a sulfide group, a thiocarbonyl group, a sulfonyl group, a divalent hydrocarbon group, and the like. The divalent linking group represented by $R^{p2}$ is preferably a carbonyloxy group, a sulfonyl group, an alkanediyl group or a cycloalkanediyl group, more preferably a carbonyloxy group or a cycloalkanediyl group, still more preferably a carbonyloxy group or a norbornanediyl group, and particularly preferably a carbonyloxy group.

The monovalent hydrocarbon group having 1 to 20 carbon atoms which may be represented by $R^{p3}$ or $R^{p4}$ is exemplified by an alkyl group having 1 to 20 carbon atoms, and the like. The monovalent fluorinated hydrocarbon group having 1 to 20 carbon atoms which may be represented by $R^{p3}$ or $R^{p4}$ is exemplified by a fluorinated alkyl group having 1 to 20 carbon atoms, and the like. $R^{p3}$ and $R^{p4}$ each independently represent preferably a hydrogen atom, the fluorine atom or the fluorinated alkyl group, more preferably the fluorine atom or the perfluoroalkyl group, and still more preferably the fluorine atom or the trifluoromethyl group.

The monovalent fluorinated hydrocarbon group having 1 to 20 carbon atoms which may be represented by $R^{p5}$ or $R^{p6}$ is exemplified by a fluorinated alkyl group having 1 to 20 carbon atoms, and the like. $R^{p5}$ and $R^{p6}$ each independently represent preferably a fluorine atom or a fluorinated alkyl group, more preferably a fluorine atom or a perfluoroalkyl group, still more preferably a fluorine atom or a trifluoromethyl group, and particularly preferably a fluorine atom.

In the above formula (c), $n^{p1}$ is preferably an integer of 0 to 5, more preferably an integer of 0 to 3, still more preferably an integer of 0 to 2, 0 and particularly preferably 1.

In the above formula (c), $n^{p2}$ is preferably an integer of 0 to 5, more preferably an integer of 0 to 2, still more preferably 0 and 1, and particularly preferably 0.

In the above formula (c), $n^{p3}$ is preferably an integer of 1 to 5, more preferably an integer of 1 to 4, still more preferably an integer of 1 to 3, 1 and particularly preferably 2.

The monovalent radiation-sensitive onium cation represented by $X^+$ is degraded by the irradiation with the exposure light. In the light-exposed regions, a sulfonic acid is generated from the sulfonate anion, and a proton generated through the degradation of the photo-labile onium cation. The monovalent radiation-sensitive onium cation represented by X⁺ is exemplified by a cation represented by the following formula (c-a) (hereinafter, may be also referred to as "cation (c-a)"), a cation represented by the following formula (c-b) (hereinafter, may be also referred to as "cation (c-b)"), a cation represented by the following formula (c-c) (hereinafter, may be also referred to as "cation (c-c)"), and the like.

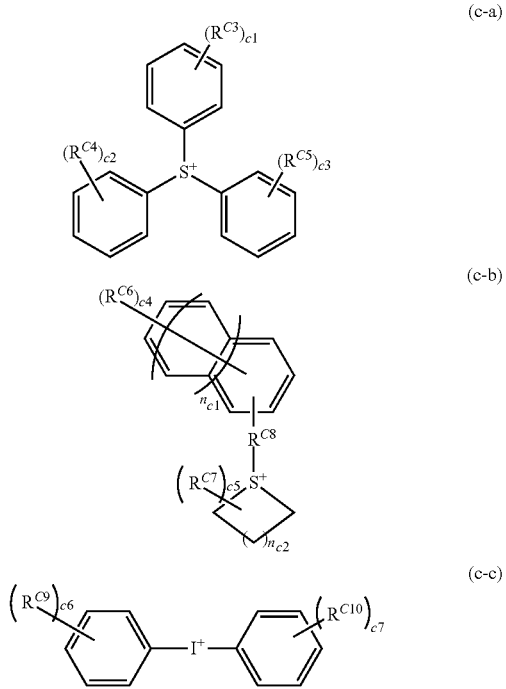

In the above formula (c-a), $R^{C3}$, $R^{C4}$ and $R^{C5}$ each independently represent a substituted or unsubstituted linear or branched alkyl group having 1 to 12 carbon atoms, a substituted or unsubstituted aromatic hydrocarbon group having 6 to 12 carbon atoms, —OSO$_2$—$R^{CC1}$ or —SO$_2$—$R^{CC2}$, or at least two of $R^{C3}$, $R^{C4}$ and $R^{C5}$ taken together represent a ring structure; $R^{CC1}$ and $R^{CC2}$ each independently represent a substituted or unsubstituted linear or branched alkyl group having 1 to 12 carbon atoms, a substituted or unsubstituted alicyclic hydrocarbon group having 5 to 25 carbon atoms, or a substituted or unsubstituted aromatic hydrocarbon group having 6 to 12 carbon atoms; and c1, c2 and c3 are each independently an integer of 0 to 5, wherein in a case where $R^{C3}$ to $R^{C5}$ and $R^{CC1}$ and $R^{CC2}$ are each present in a plurality of number, a plurality of $R^{C3}$s may be identical or different, a plurality of $R^{C4}$s may be identical or different, a plurality of $R^{C5}$s may be identical or different, a plurality of $R^{CC1}$s may be identical or different, and a plurality of $R^{CC2}$s may be identical or different.

In the above formula (c-b), $R^{C6}$ represents a substituted or unsubstituted linear or branched alkyl group having 1 to 8 carbon atoms or a substituted or unsubstituted aromatic hydrocarbon group having 6 to 8 carbon atoms; c4 is an integer of 0 to 7, wherein in a case where $R^{C6}$ is present in a plurality of number, a plurality of $R^{C6}$s may be identical or different, or the plurality of $R^{C6}$s may taken together represent a ring structure; $R^{C7}$ represent a substituted or unsubstituted linear or branched alkyl group having 1 to 7 carbon atoms or a substituted or unsubstituted aromatic hydrocarbon group having 6 or 7 carbon atoms; c5 is an integer of 0 to 6, wherein in a case where $R^{C7}$ is present in a plurality of number, a plurality of $R^{C7}$s may be identical or different, or the plurality of $R^{C7}$ may taken together represent a ring structure; $n_{c2}$ is an integer of 0 to 3; $R^{C8}$ represents a single bond or a divalent organic group having 1 to 20 carbon atoms; and $n_{c1}$ is an integer of 0 to 2.

In the above formula (c-c), $R^{C9}$ and $R^{C10}$ each independently represent a substituted or unsubstituted linear or branched alkyl group having 1 to 12 carbon atoms, a substituted or unsubstituted aromatic hydrocarbon group having 6 to 12 carbon atoms, —OSO$_2$—$R^{CC3}$ or —SO$_2$—$R^{CC4}$, or $R^{C9}$ and $R^{C10}$ taken together represent a ring structure; $R^{CC3}$ and $R^{CC4}$ each independently represent a substituted or unsubstituted linear or branched alkyl group having 1 to 12 carbon atoms, a substituted or unsubstituted alicyclic hydrocarbon group having 5 to 25 carbon atoms, or a substituted or unsubstituted aromatic hydrocarbon group having 6 to 12 carbon atoms; and c6 and c7 are each independently an integer of 0 to 5, wherein in a case where $R^{C9}$, $R^{C10}$, $R^{CC3}$ and $R^{CC4}$ are each present in a plurality of number, a plurality of $R^{C9}$s may be identical or different, a plurality of $R^{C10}$s may be identical or different, a plurality of $R^{CC3}$s may be identical or different, and a plurality of $R^{CC4}$s may be identical or different.

Examples of the unsubstituted linear alkyl group include which may be represented by $R^{C3}$, $R^{C4}$, $R^{C5}$, $R^{C6}$, $R^{C7}$, $R^{C9}$ or $R^{C10}$ include a methyl group, an ethyl group, a n-propyl group, a n-butyl group, and the like.

Examples of the unsubstituted branched alkyl group which may be represented by $R^{C3}$, $R^{C4}$, $R^{C5}$, $R^{C6}$, $R^{C7}$, $R^{C9}$ or $R^{C10}$ include an i-propyl group, an i-butyl group, a sec-butyl group, a t-butyl group, and the like.

Examples of the unsubstituted aromatic hydrocarbon group which may be represented by $R^{C3}$, $R^{C4}$, $R^{C5}$, $R^{C9}$ or $R^{C10}$ include:

aryl groups such as a phenyl group, a tolyl group, a xylyl group, a mesityl group and a naphthyl group;

aralkyl groups such as a benzyl group and a phenethyl group; and the like.

Examples of the unsubstituted aromatic hydrocarbon group which may be represented by $R^{C6}$ or $R^{C7}$ include a phenyl group, a tolyl group, a benzyl group, and the like.

The divalent organic group represented by $R^{C8}$ is exemplified by groups similar to those exemplified for the divalent organic group having 1 to 20 carbon atoms which may be represented by $R^{F5}$ and $R^{F8}$ in the above formula (f-2), and the like.

Examples of the substituent which may substitute for a hydrogen atom included in the alkyl group or the aromatic hydrocarbon group include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, halogen atoms are preferred, and a fluorine atom is more preferred.

$R^{C3}$, $R^{C4}$, $R^{C5}$, $R^{C6}$, $R^{C7}$, $R^{C9}$ and $R^{C10}$ each independently represent preferably the unsubstituted linear or branched alkyl group, the fluorinated alkyl group, the unsubstituted monovalent aromatic hydrocarbon group, —OSO$_2$—$R^{BB5}$, and —SO$_2$—$R^{BB5}$, more preferably the fluorinated alkyl group or the unsubstituted monovalent aromatic hydrocarbon group, and still more preferably the fluorinated alkyl group, wherein $R^{BB5}$ represents an unsubstituted monovalent alicyclic hydrocarbon group or an unsubstituted monovalent aromatic hydrocarbon group.

In the formula (c-a), c1, c2 and c3 are preferably an integer of 0 to 2, more preferably 0 or 1, and still more preferably 0. In the formula (c-b), c4 is preferably an integer of 0 to 2, more preferably 0 or 1, and still more preferably 1; c5 is preferably an integer of 0 to 2, more preferably 0 or 1, and still more preferably 0; $n_{c2}$ is preferably 2 or 3, and more preferably 2; and $n_{c1}$ is preferably 0 or 1, and more preferably 0. In the formula (c-c), c6 and c7 are preferably an integer of 0 to 2, more preferably 0 or 1, and still more preferably 0.

Of these, as $X^+$, the cation (c-a) and the cation (c-b) are preferred, and a diphenyliodonium cation, a triphenylsulfonium cation, a 1-[2-(4-cyclohexylphenylcarbonyl)propan-2-yl]tetrahydrothiophenium cation, and a 4-cyclohexylsulfonylphenyldiphenylsulfonium cation are more preferred.

Examples of the acid generating agent represented by the above formula (c) include compounds represented by the following formulae (c1) to (c17) (hereinafter, may be also referred to as "compounds (c1) to (c17)"), and the like.

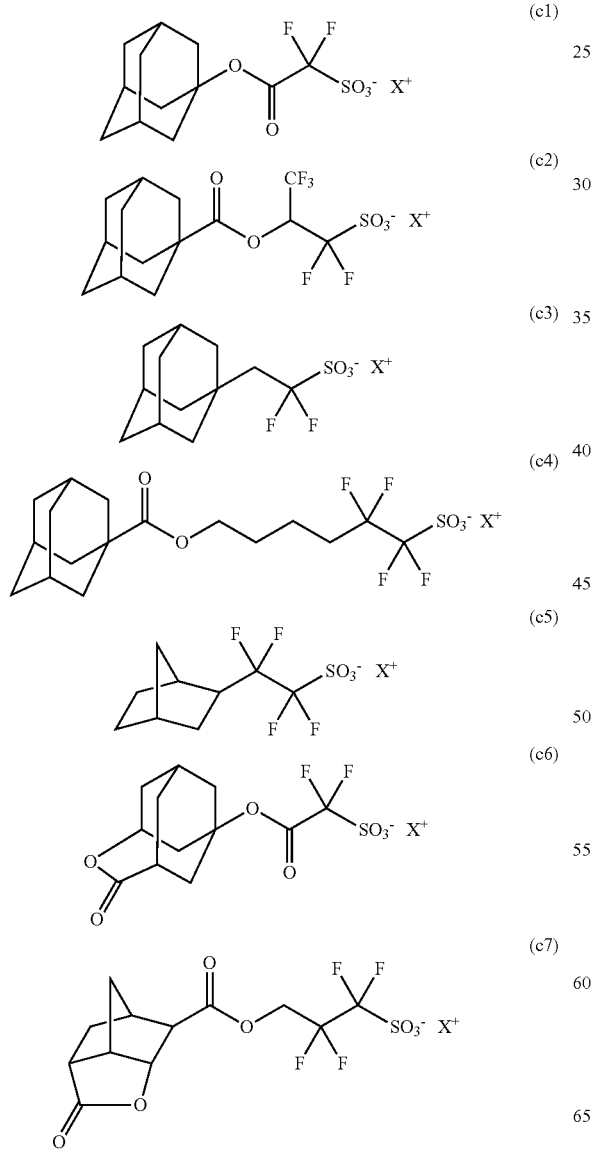

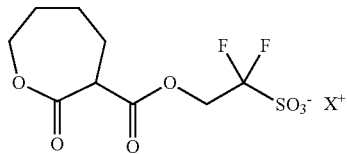

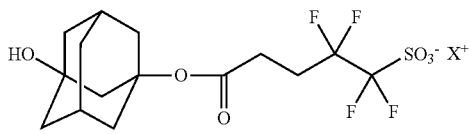

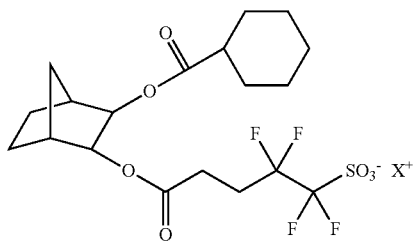

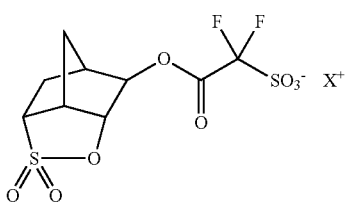

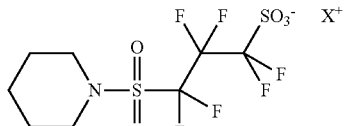

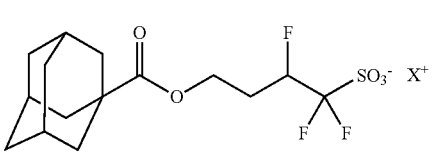

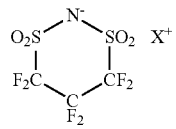

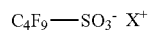

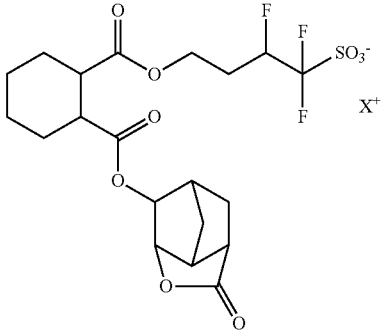

-continued

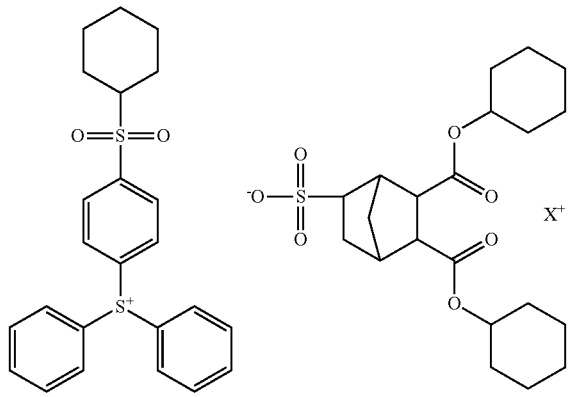

(c17)

In the above formulae (c1) to (c17), $X^+$ represents a monovalent radiation-sensitive onium cation.

As the radiation-sensitive acid generating agent (c), an onium salt compound is preferred, a sulfonium salt compound and an iodonium salt more preferred, and the compounds (c5), (c14), (c15), (c16) and (c17) are still more preferred.

Alternatively, the radiation-sensitive acid generating agent (c) may be a part of the polymer constituting the polymer component (1). In this case, the radiation-sensitive acid generating agent (c) is present in the form of a group obtained by eliminating one hydrogen atom from the aforementioned compound and bound to the polymer.

In the case where the radiation-sensitive acid generating agent (c) is the component different from the polymer component (1), the lower limit of the content of the radiation-sensitive acid generating agent (c) with respect to 100 parts by mass of the polymer component (1) is preferably 0.1 parts by mass, more preferably 1 part by mass, still more preferably 5 parts by mass, and particularly preferably 15 parts by mass. On the other hand, the upper limit of the content of the radiation-sensitive acid generating agent (c) is preferably 50 parts by mass, and more preferably 30 parts by mass.

In the case where the radiation-sensitive acid generating agent (c) is a part of the polymer constituting the polymer component (1), the proportion of the radiation-sensitive acid generating agent (c) contained with respect to 1 mol of the polymer component (1) is preferably 0.001 mol, more preferably 0.002 mol, and still more preferably 0.01 mol. On the other hand, the upper limit of the proportion of the radiation-sensitive acid generating agent (c) is preferably 0.5 mol, and more preferably 0.3 mol.

When the content or the proportion of the radiation-sensitive acid generating agent (c) contained is less than the lower limit, the sensitivity may be deteriorated. To the contrary, when the content or the proportion of the radiation-sensitive acid generating agent (c) contained is greater than the upper limit, it may be difficult to form the resist film, and/or the rectangularity of the cross-sectional shape of the resist pattern may be deteriorated.

In the case where the generative component (2) is different from the polymer component (1), the lower limit of the content of the generative component (2) with respect to the solid content of the chemically amplified resist material is preferably 5% by mass, more preferably 10% by mass, and still more preferably 15% by mass. On the other hand, the upper limit of the content of the generative component (2) is preferably 40% by mass, and more preferably 30% by mass. When the content of the generative component (2) falls within the above range, the sensitivity and lithography performances of the chemically amplified resist material can be more improved. The "solid content" as referred to herein means the entire component of the chemically amplified resist material except for a solvent. Further, the term "content of the generative component (2)" as referred to herein means the total content of the component that is different from the polymer component (1), of the generative component (2).

Acid Diffusion Control Agent

The acid diffusion control agent that is an optional component of the chemically amplified resist material is a compound that traps an acid and a cation, and serves as a quencher. When the chemically amplified resist material contains the acid diffusion control agent, a surplus acid generated in the resist film can be neutralized, whereby a chemical contrast of the latent image of the acid between the patternwise exposed regions and the patternwise unexposed regions can be increased.

The acid diffusion control agent may be classified into a radioactive ray-reactive compound and a radioactive ray-unreactive compound.

The radioactive ray-unreactive compound is preferably a basic compound. The basic compound is exemplified by hydroxide compounds, carboxylate compounds, amine compounds, imine compounds, amide compounds, and the like, and more specifically, primary to tertiary aliphatic amines, aromatic amines, heterocyclic amines, nitrogen-containing compounds that include a carboxy group, nitrogen-containing compounds that include a sulfonyl group, nitrogen-containing compounds that include a hydroxy group, nitrogen-containing compounds that include a hydroxyphenyl group, alcoholic nitrogen-containing compounds, nitrogen-containing compounds that include a carbamate group, amide compounds, imide compounds, and the like. Of these, the nitrogen-containing compounds that include a carbamate group are preferred.

Moreover, the basic compound may also be a Troger's base; a hindered amine such as diazabicycloundecene (DBU), diazabicyclononene (DBM) and the like; and an ionic quencher such as tetrabutylammonium hydroxide (TBAH), tetrabutylammonium lactate and the like.

Examples of the primary aliphatic amine include: ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, tetraethylenepentamine, and the like.

Examples of the secondary aliphatic amine include: dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyl tetraethylene pentamine, and the like.

Examples of the tertiary aliphatic amine include: trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N', N'-tetramethylmethylenediamine, N,N,N',N'-tetramethylethylenediamine, N,N,N',N'-tetramethyltetraethylenepentamine, and the like.

Examples of the aromatic amine and the heterocyclic amine include: an aniline derivative such as aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, N,N-dimethyltoluidine; diphenyl(p-tolyl)amine; methyldiphenylamine; triphenylamine; phenylenediamine; naphthylamine; diaminonaphthalene; a pyrrole derivative such as pyrrole, 2H-pyrrole, 1-methylpyrrole, 2,4-dimethylpyrrole, 2,5-dimethylpyrrole, N-methylpyrrole; an oxazole derivative such as oxazole and isoxazole; a thiazole derivative such as thiazole and isothiazole; an imidazole derivative such as imidazole, 4-methylimidazole, 4-methyl-2-phenylimidazole; pyrazole derivative; a furazane derivative; a pyrroline derivative such as pyrroline, 2-methyl-1-pyrroline; a pyrrolidine derivative such as pyrrolidine, N-methylpyrrolidine, pyrrolidinone, N-methylpyrrolidone; an imidazoline derivative; an imidazolidine derivative; a pyridine derivative such as pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, dimethylaminopyridine; a pyridazine derivative; a pyrimidine derivative; a pyrazine derivative; a pyrazoline derivative; a pyrazolidine derivative; a piperidine derivative; a piperazine derivative; a morpholine derivative; an indole derivative; an isoindole derivative; a 1H-indazole derivative; an indoline derivative; a quinolone derivative such as quinoline, 3-quinolinecarbonitrile; an isoquinoline derivative; a cinnoline derivative; a quinazoline derivative; a quinoxaline derivative; a phthalazine derivative; a purine derivative; a pteridine derivative; a carbazole derivative; a phenanthridine derivative; an acridine derivative; a phenazine derivative; a 1,10-phenanthroline derivative; an adenine derivative; an adenosine derivative; a guanine derivative; a guanosine derivative; an uracil derivative; an uridine derivative; and the like.

Examples of the nitrogen-containing compound containing a carboxy group include: aminobenzoic acid; indolecarboxylic acid; an amino acid derivative such as nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, methoxyalanine, and the like.

Examples of the nitrogen-containing compound containing a sulfonyl group include: 3-pyridinesulfonic acid, pyridinium p-toluenesulfonate, and the like.

Examples of the nitrogen-containing compound containing a hydroxy group, of the nitrogen-containing compound containing a hydroxyphenyl group, and of the alcoholic nitrogen-containing compound include: 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidineethanol, 1-aziridineethanol, N-(2-hydroxyethyl)phthalimide, N-(2-hydroxyethyl)isonicotineamide, and the like.

Examples of the nitrogen-containing compound containing a carbamate group include: N-(tert-butoxycarbonyl)-L-alanine, N-(tert-butoxycarbonyl)-L-alanine methyl ester, (S)-(−)-2-(tert-butoxycarbonylamino)-3-cyclohexyl-1-propanol, (R)-(+)-2-(tert-butoxycarbonylamino)-3-methyl-1-butanol, (R)-(+)-2-(tert-butoxycarbonylamino)-3-phenylpropanol, (S)-(−)-2-(tert-butoxycarbonylamino)-3-phenylpropanol, (R)-(+)-2-(tert-butoxycarbonylamino)-3-phenyl-1-propanol, (S)-(−)-2-(tert-butoxycarbonylamino)-3-phenyl-1-propanol, (R)-(+)-2-(tert-butoxycarbonylamino)-1-propanol, (S)-(−)-2-(tert-butoxycarbonylamino)-1-propanol, N-(tert-butoxycarbonyl)-L-asparatic acid 4-benzyl ester, N-(tert-butoxycarbonyl)-O-benzyl-L-threonine, (R)-(+)-1-(tert-butoxycarbonyl)-2-tert-butyl-3-methyl-4-imidazolidinone, (S)-(−)-1-(tert-butoxycarbonyl)-2-tert-butyl-3-methyl-4-imidazolidinone, N-(tert-butoxycarbonyl)-3-cyclohexyl-L-alanine methyl ester, N-(tert-butoxycarbonyl)-L-cysteine methyl ester, N-(tert-butoxycarbonyl)ethanolamine, N-(tert-butoxycarbonyl)ethylenediamine, N-(tert-butoxycarbonyl)-D-glucoseamine, Nα-(tert-butoxycarbonyl)-L-glutamine, 1-(tert-butoxycarbonyl)imidazole, N-(tert-butoxycarbonyl)-L-isoleucine, N-(tert-butoxycarbonyl)-L-isoleucine methyl ester, N-(tert-butoxycarbonyl)-L-leucinol, Na-(tert-butoxycarbonyl)-L-lysine, N-(tert-butoxycarbonyl)-L-methionine, N-(tert-butoxycarbonyl)-3-(2-naphthyl)-L-alanine, N-(tert-butoxycarbonyl)-L-phenylalanine, N-(tert-butoxycarbonyl)-L-phenylalanine methyl ester, N-(tert-butoxycarbonyl)-D-prolinal, N-(tert-butoxycarbonyl)-L-proline, N-(tert-butoxycarbonyl)-L-proline-N'-methoxy-N'-methylamide, N-(tert-butoxycarbonyl)-1H-pyrazole-1-carboxyamidine, (S)-(−)-1-(tert-butoxycarbonyl)-2-pyrrolidinemethanol, (R)-(+)-1-(tert-butoxycarbonyl)-2-pyrrolidinemethanol, 1-(tert-butoxycarbonyl)3-[4-(1-pyrrolyl)phenyl]-L-alanine, N-(tert-butoxycarbonyl)-L-serine, N-(tert-butoxycarbonyl)-L-serine methyl ester, N-(tert-butoxycarbonyl)-L-threonine, N-(tert-butoxycarbonyl)-p-toluenesulfonamide, N-(tert-butoxycarbonyl)-S-trityl-L-cysteine, Na-(tert-butoxycarbonyl)-L-tryptophan, N-(tert-butoxycarbonyl)-L-tyrosine, N-(tert-butoxycarbonyl)-L-tyrosine methyl ester, N-(tert-butoxycarbonyl)-L-valine, N-(tert-butoxycarbonyl)-L-valine methyl ester, N-(tert-butoxycarbonyl)-L-valinol, tert-butyl N-(3-hydroxypropyl)carbamate, tert-butyl N-(6-aminohexyl)carbamate, tert-butylcarbamate, tert-butyl carbazate, tert-butyl-N-(benzyloxy) carbamate, tert-butyl-4-benzyl-1-piperazinecarboxylate, tert-butyl (1S,4S)-(−)-2,5-diazabicyclo[2.2.1]heptane-2-carboxylate, tert-butyl-N-(2,3-dihydroxypropyl)carbamate, tert-butyl (S)-(−)-4-formyl-2,2-dimethyl-3-oxazolidinecarboxylate, tert-butyl[R—(R*, S*)]—N-[2-hydroxy-2-(3-hydroxyphenyl)-1-methylethyl]carbamate, tert-butyl-4-oxo-1-piperidinecarboxylate, tert-butyl 1-pyrrolecarboxylate, tert-butyl 1-pyrrolidinecarboxylate, tert-butyl (tetrahydro-2-oxo-3-furanyl)carbamate, and the like.

Examples of the amide compound include: formamide, N-methylformamide, N,N-dimethylformamide, acetamide, N-methylacetamide, N,N-dimethylacetamide, propionamide, benzamide, 1-cyclohexylpyrrolidone, and the like.

Examples of the imide compound include: phthalimide, succinimide, maleimide, and the like.

Furthermore, the radioactive ray-reactive compound is classified into a compound that is degraded by a radioactive ray to lose acid diffusion controllability (radioactive ray-degradable compound) and a compound that is generated by a radioactive ray to acquire acid diffusion controllability (radioactive ray-generable compound).

When the radioactive ray-degradable compound is degraded only in the patternwise exposed regions in the patternwise exposure step described later, the effect of trapping the acid and the cation is deteriorated in the patternwise exposed regions, whereas the effect of trapping the acid and the cation is maintained in the patternwise unexposed regions. Accordingly, a chemical contrast of the latent image of the acid between the light-exposed regions and the light-unexposed regions can be improved.

The radioactive ray-degradable compound is preferably a sulfonic acid salt or carboxylic acid salt containing a radioactive ray-degradable cation. As the sulfonic acid in the sulfonic acid salt, a weaker acid is preferred, and a sulfonic acid that includes a hydrocarbon group having 1 to 20 carbon atoms, and not having a fluorine atom is more preferred. Examples of the sulfonic acid include sulfonic acids such as alkylsulfonic acids, benzenesulfonic acid and 10-camphorsulfonic acid. As the carboxylic acid in the carboxylic acid salt, a weaker acid is preferred, and a carboxylic acid having 1 to 20 carbon atoms is more preferred. Examples of the carboxylic acid include carboxylic acids such as formic acid, acetic acid, propionic acid, tartaric acid, succinic acid, cyclohexylcarboxylic acid, benzoic acid and salicylic acid. The radioactive ray-degradable cation in the carboxylic acid salt containing the radioactive ray-degradable cation is preferably an onium cation, and examples of the onium cation include iodonium cations, sulfonium cations, and the like.

When the radioactive ray-generable compound is generated only in the patternwise exposed regions in the patternwise exposure step, the effect of trapping the acid and the cation is exerted in the patternwise exposed regions, but not in the patternwise unexposed regions.

Alternatively, the radioactive ray-generable compound may be a radioactive ray-generable compound that is not generated in the patternwise exposure step but is generated in the floodwise exposure step described later. In this case, the radiation-sensitive sensitizer can be generated efficiently in the regions light-exposed in the patternwise exposure step, and additionally an unnecessary acid and cation in the regions unexposed to light in floodwise exposure step can be trapped.

The radioactive ray-generable compound is preferably a compound that is capable of generating a base upon an exposure (radiation-sensitive base generating agent), and more preferably a nitrogen-containing organic compound that is capable of generating an amino group.

Examples of the radiation-sensitive base generating agent include compounds disclosed in Japanese Unexamined Patent Application, Publication Nos. H4-151156, H4-162040, H5-197148, H5-5995, H6-194834, H8-146608 and H10-83079, and European patent No. 622682.

In addition, the radiation-sensitive base generating agent is exemplified by a compound that includes a carbamate group (urethane bond), a compound that includes an acyloxyimino group, an ionic compound (anion-cation complex), a compound that includes a carbamoyloxyimino group, and the like, and a compound that includes a carbamate group (urethane bond), a compound that includes an acyloxyimino group, and an ionic compound (anion-cation complex) are preferred.

Further, as the radiation-sensitive base generating agent, a compound having a ring structure in a molecule thereof is preferred. Examples of the ring structure include a benzene ring structure, a naphthalene ring structure, an anthracene ring structure, a xanthone ring structure, a thiaxanthon ring structure, an anthraquinone ring structure, a fluorene ring structure, and the like.

Examples of the radiation-sensitive base generating agent include: 2-nitrobenzylcarbamate, 2,5-dinitrobenzyl cyclohexylcarbamate, N-cyclohexyl-4-methylphenylsulfonamide, 1,1-dimethyl-2-phenylethyl-N-isopropylcarbamate, and the like.

Also, the acid diffusion control agent may be a compound that is generated through a thermal reaction to acquire acid diffusion controllability (thermally-generable compound). In this case, it is desired that the acid diffusion control agent is generated in a baking step performed after the floodwise exposure step described later. In light of the acid diffusion control agent thus acquiring the acid diffusion controllability in the baking step, the heating temperature in the baking step is preferably higher than the heating temperatures in other steps.

In the case where the chemically amplified resist material contains the acid diffusion control agent, the lower limit of the content of the acid diffusion control agent with respect to 100 parts by mass of the polymer component (1) is preferably 0.1 parts by mass, more preferably 1 part by mass, and more preferably 4 parts by mass. On the other hand, the upper limit of the content of the acid diffusion control agent is preferably 20 parts by mass, and more preferably 10 parts by mass. When the content of the acid diffusion control agent is less than the lower limit, the acid diffusion control agent may not be capable of trapping the acid and the cation satisfactorily. To the contrary, when the content of the acid diffusion control agent is greater than the upper limit, the sensitivity may be unduly decreased.

Radical Trapping Agent

The radical trapping agent traps a free radical. When the chemically amplified resist material contains the radical trapping agent, the generation of the radiation-sensitive sensitizer through a reaction mediated by the radical in the patternwise unexposed regions can be reduced, leading to a greater improvement of a contrast in terms of acid concentration between the patternwise exposed regions and the light-unexposed regions after the floodwise exposure step described later. The radical trapping agent is exemplified by compounds such as phenol compounds, quinone compounds and amine compounds, and naturally occurring antioxidants such as rubber, and the like.

Crosslinking Agent

The crosslinking agent is a compound having at least two functional groups, and decreases the solubility of the patternwise exposed regions in a developer solution by, in the baking step after the floodwise exposure step described later, causing a crosslinking reaction of the polymer component (1) to occur through an acid-catalyzed reaction, and thereby increasing the molecular weight of the polymer component (1). Examples of the functional group include a (meth)acryloyl group, a hydroxymethyl group, an alkoxymethyl group, an epoxy group, a vinyl ether group, and the like.

Other Additive

Other additive is exemplified by a surfactant, an antioxidant, a dissolution inhibitor, a plasticizer, a stabilizer, a colorant, a halation inhibitor, a dye, and the like. Well-known additives may be used as the other additive.

Solvent

The solvent is exemplified by an alcohol solvent, an ether solvent, a ketone solvent, an amide solvent, an ester solvent, a hydrocarbon solvent, and the like.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol and benzyl alcohol, and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether; and the like.

Examples of the ether solvent include:

dialkyl ether solvents such as diethyl ether, dipropyl ether and dibutyl ether;

cyclic ether solvents such as tetrahydrofuran and tetrahydropyran;

aromatic ring-containing ether solvents such as diphenyl ether and anisole; and the like.

Examples of the ketone solvent include:

chain ketone solvents such as acetone, methylethylketone, methyl-n-propylketone, methyl-n-butylketone, diethyl ketone, methyl-iso-butylketone, 2-heptanone, ethyl-n-butylketone, methyl-n-hexylketone, di-iso-butylketone and trimethylnonanone;

cyclic ketone solvents such as cyclopentanone, cyclohexanone, cycloheptanone, cyclooctanone and methylcyclohexanone;

2,4-pentanedione, acetonyl acetone, acetophenone, and the like.

Examples of the amide solvent include:

cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

ester acetate solvents such as methyl acetate, ethyl acetate, n-propyl acetate, iso-propyl acetate, n-butyl acetate, iso-butyl acetate, sec-butyl acetate, n-pentyl acetate, i-pentyl acetate, sec-pentyl acetate, 3-methylbutyl acetate, 3-methoxybutyl acetate, methylpentyl acetate, 2-ethylbutyl acetate, 2-ethylhexyl acetate, benzyl acetate, cyclohexyl acetate, methylcyclohexyl acetate and n-nonyl acetate;

polyhydric alcohol partial ether acetate solvents such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate and dipropylene glycol monoethyl ether acetate;

lactone solvents such as γ-butyrolactone and valerolactone;

carbonate solvents such as diethyl carbonate, ethylene carbonate and propylene carbonate;

glycol diacetate, methoxytriglycol acetate, ethyl propionate, n-butyl propionate, iso-amyl propionate, diethyl oxalate, di-n-butyl oxalate, methyl acetoacetate, ethyl acetoacetate, methyl lactate, ethyl lactate, n-butyl lactate, n-amyl lactate, diethyl malonate, dimethyl phthalate and diethyl phthalate; and the like.

Examples of the hydrocarbon solvent include:

aliphatic hydrocarbon solvents such as n-pentane, iso-pentane, n-hexane, iso-hexane, n-heptane, iso-heptane, 2,2,4-trimethylpentane, n-octane, iso-octane, cyclohexane and methylcyclohexane;

aromatic hydrocarbon solvents such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene and n-amylnaphthalene; and the like.

Of these, an ester solvent and a ketone solvent are preferred, a polyhydric alcohol partial ether acetate solvent, a lactone solvent, a cyclic ketone solvent, ethyl lactate and a polyhydric alcohol partial ether acetate solvent are more preferred, and propylene glycol monomethyl ether acetate, γ-butyrolactone, cyclohexanone, ethyl lactate and propylene glycol monomethyl ether acetate are still more preferred, as the solvent. The chemically amplified resist material may contain one type alone, or as a mixture of two or more types of the solvent.

Preparation Method of Chemically Amplified Resist Material

The chemically amplified resist material may be prepared by, for example, mixing the polymer component (1), the component (2), and as needed other optional component, at a predetermined ratio. The chemically amplified resist material is preferably filtered through a filter having a pore size of about 0.2 µm, for example, after the mixing. The lower limit of the solid content concentration of the chemically amplified resist material is typically 0.1% by mass, preferably 0.5% by mass, and more preferably 1% by mass. On the other hand, the upper limit of the solid content concentration is typically 50% by mass, preferably 20% by mass, and more preferably 5% by mass.

Resist Pattern-Forming Method

The resist pattern-forming method includes: an applying step of applying the chemically amplified resist material on at least one face of a substrate; a patternwise exposure step of irradiating a resist film obtained after the applying with the first radioactive ray; a floodwise exposure step of irradiating with the second radioactive ray, the resist film patternwise exposed; a baking step of heating the resist film floodwise exposed; and a development step of bringing the resist film baked into contact with a developer solution.

In addition, the resist pattern-forming method may further include, before the applying step, a step of forming an organic underlayer film directly or indirectly on a face of the substrate on which the chemically amplified resist material is to be applied, and may further include, after the organic underlayer film-forming step and before the applying step, a step of forming a silicon-containing film directly or indirectly on a face of the organic underlayer film on which the chemically amplified resist material is to be applied.

Further, the resist pattern-forming method may further include, after the patternwise exposure step and before the floodwise exposure step, a step of baking the resist film (hereinafter, may be also referred to as "prior-to-floodwise-exposure baking step").

Moreover, typically after the development step, a step of forming a substrate pattern is carried out by using as a mask, the resist pattern formed by the resist pattern-forming method.

Organic Underlayer Film-Forming Step

In the organic underlayer film-forming step, an organic underlayer film is formed on a substrate. The term "organic underlayer film" as referred to herein means a film that contains an organic substance as a principal component.

The substrate is exemplified by conventionally well-known substrates such as silicon wafers, wafers coated with silicon dioxide or aluminum, glass substrates and ITO substrates.

The organic substance is exemplified by a phenol resin, an acenaphthylene resin, and the like. The "acenaphthylene resin" as referred to herein means a resin having a structural unit derived from a compound that includes an acenaphthylene skeleton.

The organic underlayer film is exemplified by a film for improving adhesiveness of the resist film to the substrate, a film for ameliorating the shape of the resist pattern, an antireflective film for reducing the reflection of the radioactive ray on the substrate, and the like. The antireflective film can inhibit generation of a standing wave due to the reflection of the radioactive ray on the substrate, etc. in the patternwise exposure step. Well-known antireflective films may be used as the aforementioned antireflective film.

In addition, it is desired that the organic underlayer film does not absorb the second radioactive ray used in the floodwise exposure step. In a case where the organic underlayer film absorbs the second radioactive ray used in the floodwise exposure step, a radioactive ray sensitization reaction may be caused in the resist film resulting from the energy transfer or electron transfer from the organic underlayer film, whereby the acid may be generated in the patternwise unexposed regions. Thus, it is preferred that a buffer layer which does not propagate a radioactive ray sensitization reaction is provided between the resist film and the organic underlayer film, and thereby the sensitization from the underlayer film which has absorbed the radioactive ray is prevented. The buffer layer is exemplified by a transparent film which does not absorb the second radioactive ray.

Silicon-Containing Film-Forming Step

In the silicon-containing film-forming step, a silicon-containing film is further formed between the organic underlayer film and the resist film. The silicon-containing film is exemplified by a Spin on glass (SOG) used in multilayer resist processes, and the like. Well-known compositions for SOG film formation can be used as the composition for SOG film formation. Moreover, in regard to conditions for the SOG film formation, etc., well-known conditions can be suitably applied.

Applying Step

In the applying step, the chemically amplified resist material is applied on at least one face of the substrate to form a resist film. In a case where the organic underlayer film-forming step and the silicon-containing film-forming step are not performed, the resist film is formed directly on the surface of the substrate, whereas in a case where the organic underlayer film-forming step and the silicon-containing film-forming step are performed, the resist film is formed on the surface of the silicon-containing film.

The application procedure of the chemically amplified resist material is exemplified by spin coating, cast coating, roll coating, and the like.

Moreover, after the chemically amplified resist material is applied onto the substrate, prebaking (PB) may be performed as needed to evaporate a solvent in the coating film. The lower limit of the PB temperature is typically 60° C., and preferably 80° C. On the other hand, the upper limit of the PB temperature is typically 140° C., and preferably 120° C. Further, the lower limit of the PB time period is typically 5 sec, and preferably 10 sec. On the other hand, the upper limit of the PB time period is typically 600 sec, and preferably 300 sec.

The lower limit of the average thickness of the resist film formed is preferably 10 nm. On the other hand, the upper limit of the average thickness of the resist film formed is preferably 1,000 nm, and more preferably 500 nm.

In addition, a protective film may be further formed on the resist film. The formation of the protective film can inhibit the deactivation of the radiation-sensitive sensitizer and the acid which are generated in the patternwise exposure step, as well as reaction intermediates thereof, leading to an improvement of process stability.

Further, in a case where the chemically amplified resist material does not contain a water-repellent polymer additive such as a polymer having a high percentage content of fluorine atom, and where liquid immersion lithography is carried in the patternwise exposure step described later, a protective film for liquid immersion which is insoluble in a liquid immersion liquid may be provided on the resist film in order to inhibit direct contact of the liquid immersion liquid with the resist film. The protective film for liquid immersion is exemplified by a solvent-removable protective film which can be removed by a solvent (see Japanese Unexamined Patent Application, Publication No. 2006-227632, for example), a developer solution-removable protective film which is removed concomitantly with a development in the development step (see WO 2005-069076 and WO 2006-035790, for example), and the like. In light of throughput, the developer solution-removable protective film for liquid immersion is preferred.

Patternwise Exposure Step

In the patternwise exposure step, at least a part of the resist film obtained after the applying is irradiated with the first radioactive ray. Specifically, a light-shielding mask having a predetermined pattern is placed on the resist film obtained in the applying step. Thereafter, the resist film is irradiated through the mask, with the first radioactive ray using a lithography device having a projection lens, an electrooptic mirror, or a reflecting mirror (radioactive ray emitting module). Thus, the radiation-sensitive sensitizer and the acid are generated from the components (a) to (c) in the patternwise exposed regions.

The first radioactive ray used in this step for the irradiation has a wavelength of no greater than 250 nm. Such a radioactive ray is exemplified by γ-rays, X-rays, α-rays, heavy particle beams, proton beams, β-rays, ion beams, electron beams, EUV (extreme-ultraviolet) rays, an ArF excimer laser beam (wavelength: 193 nm), a KrF excimer laser beam (wavelength: 248 nm), and the like. Of these, an electron beams, EUV, an ArF excimer laser and a KrF excimer laser are preferred, and an electron beams and EUV are more preferred.

The patternwise exposure step and/or the floodwise exposure step described later may be carried out either by liquid immersion lithography, or by dry lithography. In a case where the patternwise exposure step and/or the floodwise exposure step is/are performed through liquid immersion lithography, the liquid immersion liquid which may be used is exemplified by water, a fluorine-containing inert liquid, and the like. It is preferred that the liquid immersion liquid is transparent to an exposure wavelength, and has a temperature coefficient of the refractive index as small as possible so that distortion of an optical image projected onto the film is minimized. In particular, in a case where the ArF excimer laser beam (wavelength: 193 nm) is used as an exposure light source, it is preferred to use water in light of availability and ease of handling thereof in addition to the aforementioned considerations. In a case where water is used, a slight amount of an additive which reduces the surface tension of water and imparts enhanced surfactant power may be added. It is preferred that the additive has a negligible influence on an optical coating of an inferior face of a lens, without dissolving the resist film on the wafer. The water is preferably distilled water.

On the other hand, in a case where the patternwise exposure step and/or the floodwise exposure step is/are performed through dry lithography, the step(s) may be performed in an ambient air atmosphere, a vacuum atmosphere or an inert atmosphere, and a vacuum atmosphere, a nitrogen-containing inert atmosphere, and an argon-containing inert atmosphere are preferred. In addition, the upper limit of the concentration of a basic compound inevitably contaminated in the atmosphere is preferably 20 ppb, more preferably 5 ppb, and still more preferably 1 ppb.

Alternatively, an absorbing film that absorbs at least a part of the radioactive ray of a wavelength which the radiation-sensitive acid generating agent contained in the component (a) or (c) can directly absorb may be provided on the resist film obtained after the patternwise exposure step. When such an absorbing film is provided, direct generation of the acid from the radiation-sensitive acid generating agent in the patternwise unexposed regions, which is caused resulting from the irradiation with the second radioactive ray in the floodwise exposure step can be further inhibited.

Further, in a case where the radiation-sensitive sensitizer generating agent (b) includes an alcoholic hydroxyl group in which the hydrogen atom is not substituted, it is preferred that after the patternwise exposure step until the floodwise exposure step, the resist film is stored under any one of a vacuum atmosphere, a nitrogen-containing inert atmosphere and an argon-containing inert atmosphere. By storing the resist film under the atmosphere described above, an exposure of the resist film to oxygen and the termination of a radical reaction by the oxygen can be inhibited, and additionally quenching of the acid by a slight amount of a basic compound can be inhibited. As a result of these, the process tends to be more stabilized. The upper limit of the storage time period is preferably 30 min, and more preferably 10 min. When the storage time period is no greater than the upper limit, further inhibition of the decrease in sensitivity tends to be enabled.

On the other hand, in a case where the radiation-sensitive sensitizer generating agent (b) includes an alcoholic hydroxyl group in which the hydrogen atom is substituted, it is preferred that after the patternwise exposure step until the floodwise exposure step, the resist film is stored in an ambient air cleaned by using an amine-eliminating filter. By storing the resist film under the atmosphere described above, quenching of the acid by a slight amount of a basic compound can be inhibited, and consequently the process tends to be more stabilized. The upper limit of the storage time period is preferably 30 min, and more preferably 10 min. When the storage time period is no greater than the upper limit, further inhibition of the decrease in sensitivity tends to be enabled.

Prior-to-Floodwise-Exposure Baking Step

In the prior-to-floodwise-exposure baking step, the resist film after the patternwise exposure step and before the floodwise exposure step is heated. Thus, the generation of the radiation-sensitive sensitizer by the hydrolysis reaction of the radiation-sensitive sensitizer generating agent (b) etc. in the resist film can be facilitated.

The lower limit of the heating temperature is preferably 30° C., more preferably 50° C., and still more preferably 60° C. On the other hand, the upper limit of the heating temperature is preferably 150° C., more preferably 120° C., and still more preferably 100° C. The lower limit of the heating time period is preferably 5 sec, and more preferably 10 sec. On the other hand, the upper limit of the heating time period is preferably 3 min, and more preferably 60 sec. In addition, the heating is preferably performed under a humidity-controlled environment. When the heating is performed under such an environment, an influence of the moisture in the ambient air on a hydrolysis reaction can be reduced in a case where the hydrolysis reaction is used as a deprotection reaction which produces the radiation-sensitive sensitizer from the radiation-sensitive sensitizer generating agent (b) etc.

Floodwise Exposure Step

In the floodwise exposure step, the entire face (entire face including the patternwise exposed regions and the patternwise unexposed regions) of the resist film after the patternwise exposure step is irradiated with the second radioactive ray. The second radioactive ray may be applied onto the entire face of the wafer at once, or combined or superimposed multiple local applications of the second radioactive ray may be executed.

In this step, since only the radiation-sensitive sensitizer which is generated by the first radioactive ray in patternwise exposed regions of the resist film absorbs the second radioactive ray, selective absorption of the second radioactive ray occurs in the patternwise exposed regions. Thus, the acid can be continuously generated only in the patternwise exposed regions, leading to a significant improvement of the sensitivity. On the other hand, the acid is not substantially generated in the patternwise unexposed regions, and consequently the sensitivity can be improved while the chemical contrast in the resist film is maintained.

Common light sources may be used as a light source of the second radioactive ray used in this step. Examples of the second radioactive ray include: ultraviolet rays emitted from a mercury lamp, a xenon lamp, or the like and filtered through a band pass filter or a cut-off filter so as to have a desired wavelength; ultraviolet rays emitted from an LED light source, a laser diode, a laser light source or the like and having a narrow-bandwidth; and the like.

The second radioactive ray has a wavelength of greater than 250 nm. The lower limit of the wavelength of the second radioactive ray is preferably 280 nm, and more preferably 300 nm. On the other hand, the upper limit of the wavelength is preferably 450 nm, and more preferably 400 nm. When the wavelength is less than the lower limit, the amount of the acid and the radiation-sensitive sensitizer which may be generated by the second radioactive ray in the patternwise unexposed regions may be increased. To the contrary, when the wavelength is greater than the upper limit, an efficiency of the sensitization reaction caused by the second radioactive ray may be decreased.

Baking Step

In the baking step, the resist film obtained after the floodwise exposure step is heated (post exposure baking; PEB). Thus, the dissociation of the acid-labile group included in the polymer (A) or the like is accelerated by the acid generated from the radiation-sensitive acid generating agent (c) or the like in the patternwise exposed regions. In addition, in a case where the chemically amplified resist material contains the crosslinking agent and the like, a crosslinking reaction and the like may occur in the patternwise exposed regions. As a result of these, a difference in the solubility in the developer solution is produced between the light-exposed regions and the light-unexposed regions. Further, although a side wall face of the resist may be wavy due to an influence of a standing wave of the radioactive ray within the resist film, the PEB enables the diffusion of a reactant to be facilitated in the resist film, and consequently the formation of the wave-like surface can be reduced.

The atmosphere of the PEB is exemplified by an ambient air atmosphere, a nitrogen-containing inert atmosphere, an argon-containing inert atmosphere, and the like. The lower limit of the PEB temperature is typically 50° C., and preferably 80° C. On the other hand, the upper limit of the PEB temperature is typically 180° C., and preferably 130° C. Also, the lower limit of the PEB time period is typically no less than 5 sec, and preferably 10 sec. On the other hand, the upper limit of the PEB time period is typically no less than 600 sec, and preferably 300 sec.

Development Step

In the development step, the resist film obtained after the baking step is brought into contact with a developer solution. Thus, the patternwise exposed regions or the light-unexposed regions are eliminated with the developer solution, whereby a predetermined resist pattern is formed. In a case of a development with an alkali, the patternwise exposed regions are eliminated in the development step to form a positive resist pattern. On the other hand, in a case of a development with an organic solvent, the regions unexposed to the patterning light are developed in the development step to form a negative resist pattern. The negative resist pattern obtained after the development is generally rinsed with a rinse agent such as water and an alcohol, followed by drying.

In the case of the development with an alkali, examples of the developer solution which may be used in the development include alkaline aqueous solutions prepared by dissolving at least one of alkaline compounds such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene, 1,5-diazabicyclo-[4.3.0]-5-nonene, etc., and the like. Of these, an aqueous TMAH solution is preferred, a 2% by mass to 3% by mass aqueous TMAH solution is more preferred, and a 2.38% by mass aqueous TMAH solution is still more preferred.

In the case of the development with an organic solvent, examples of the developer solution which may be used in the development include organic solvents such as hydrocarbon solvents, ether solvents, ester solvents, ketone solvents and alcohol solvents, or solvents containing an organic solvent. The organic solvent which may be used is one type alone, or a mixture of two or more types of the solvent exemplified in connection with the solvent of the aforementioned chemically amplified resist material, and the like. Of these, ester solvents and ketone solvents are preferred. As the ester solvent, acetic acid ester solvents are preferred, and n-butyl acetate is more preferred. As the ketone solvent, chain ketones are preferred, and 2-heptanone is more preferred. The lower limit of the content of the organic solvent in the developer solution is preferably 80% by mass, more preferably 90% by mass, still more preferably 95% by mass and particularly preferably 99% by mass. Components other than the organic solvent in the developer solution are exemplified by water, silicone oil, and the like.

Substrate Pattern-Forming Step

In the substrate pattern-forming step, the substrate is etched, for example, by using, as a mask, the resist pattern formed in the development step such that the substrate has a pattern. The etching may be dry etching under an atmosphere such as plasma excitation, or wet etching in which the substrate is immersed in a chemical liquid. After subjecting the substrate to the pattern formation, the resist pattern is normally eliminated.

EXAMPLES

Hereinafter, the present invention is explained in detail by way of Examples, but the present invention is not in any way limited to these Examples. Measuring methods of physical property values in the present Examples are described below.

Weight Average Molecular Weight (Mw) and Number Average Molecular Weight (Mn)

Mw and Mn of the polymer were measured by gel permeation chromatography (GPC). The measurements were carried out using GPC columns (G2000 HXL×2, G3000 HXL×1 and G4000 HXL×1 (each available from Tosoh Corporation) under analysis conditions of: flow rate: 1.0 mL/min; elution solvent: tetrahydrofuran; sample concentration: 1.0% by mass; amount of injected sample: 100 µL; and column temperature: 40° C., with mono-dispersed polystyrene as a standard substance, using a differential refractometer as a detector.

$^{13}$C-NMR Analysis $^{13}$C-NMR analysis for determination of the proportion of the structural unit in the polymer was conducted by using a nuclear magnetic resonance apparatus ("JNM-ECX400" from JEOL, Ltd.), and DMSO-$d_6$ as a solvent for measurement, with tetramethylsilane (TMS) as an internal standard.

Synthesis of Polymer Component (1)

Monomers used for the synthesis of the polymer component (1) are shown below.

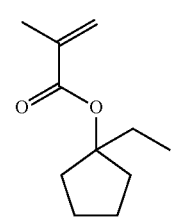

(M-1)

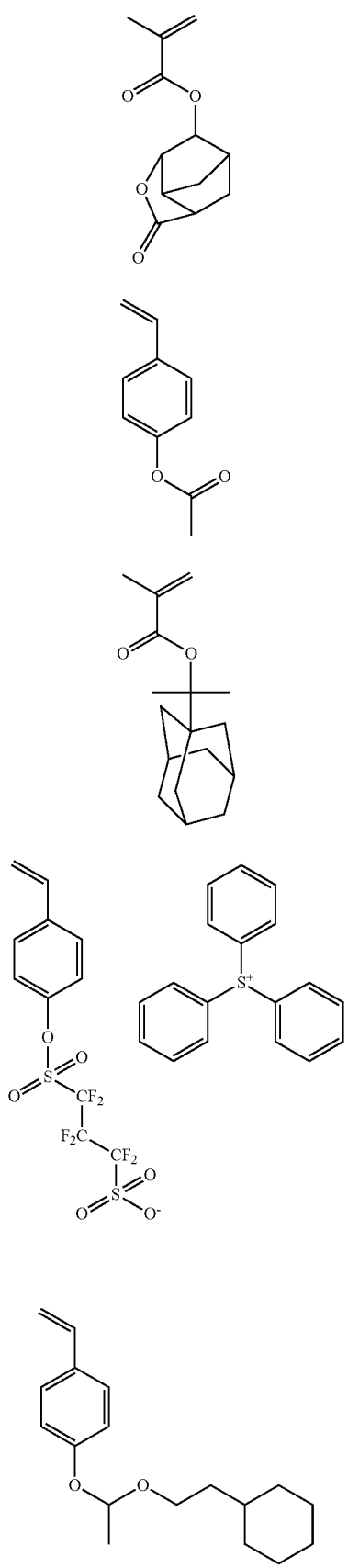

(M-2)

(M-3)

(M-4)

(M-5)

(M-6)

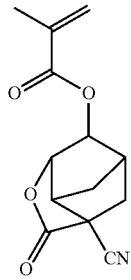

(M-7)

Synthesis Example 1

Synthesis of Polymer (S-1)

55 g (50 mol %) of the compound (M-2), 45 g (50 mol %) of the compound (M-1) and 3 g (3 mol % with respect to the total amount of the monomer) of azobisisobutyronitrile (AIBN) were dissolved in 300 g of methyl ethyl ketone, followed by polymerizing for 6 hrs under a nitrogen atmosphere while maintaining a reaction temperature at 78° C. Following the polymerization, a reaction solution was added to 2,000 g of methanol dropwise to permit solidification of the polymer. Thereafter, the polymer was washed twice with 300 g of methanol and white powder thus obtained was filtered, followed by drying at 50° C. overnight under a reduced pressure, thereby obtaining a polymer (S-1) served as the polymer component (1). The polymer (S-1) had the Mw of 7,000 and the Mw/Mn of 2.10. In addition, the result of $^{13}$C-NMR analysis indicated that the proportions of the structural units derived from the compound (M-1) and the compound (M-2) were 52 mol % and 48 mol %, respectively.

Synthesis Example 2

Synthesis of Polymer (S-2)

55 g (58 mol %) of the compound (M-3), 45 g (42 mol %) of the compound (M-1), 3 g of AIBN (4 mol % with respect to the total amount of the monomer) and 1 g of t-dodecyl mercaptan (1 mol % with respect to the total amount of the monomer) were dissolved in 150 g of propylene glycol monomethyl ether, followed by polymerizing for 16 hrs under a nitrogen atmosphere while maintaining a reaction temperature at 70° C. Following the polymerization, a reaction solution was added to 1,000 g of n-hexane dropwise to permit solidification and purification of a polymer. Subsequently, 150 g of propylene glycol monomethyl ether was added again to the polymer, then 150 g of methanol, 37 g of trimethylamine and 7 g of water were further added thereto, and a hydrolysis reaction was allowed to proceed for 8 hrs with refluxing at the boiling point to permit deacetylation of the structural unit derived from (M-3). After the reaction, the solvent and triethylamine were distilled off under reduced pressure, the resulting polymer was dissolved in 150 g of acetone, and then the solution thus obtained was added to 2,000 g of water dropwise to permit solidification of the polymer. The white powder thus formed was filtered off, followed by drying at 50° C. overnight under a reduced pressure to obtain a polymer (S-2), which served as the polymer component (1). The polymer (S-2) had the Mw of 6,000 and the Mw/Mn of 1.90. In addition, the result of $^{13}$C-NMR analysis indicated that the proportions of the structural unit derived from p-hydroxystyrene obtained by deacetylation of a structural unit derived from the compound (M-3), and the structural unit derived from the compound (M-1) were 50 mol % and 50 mol %, respectively.

Synthesis Examples 3 and 4

Syntheses of Polymers (S-3) and (S-4)

Polymers (S-3) and (S-4) which served as the polymer component (1) were synthesized by a similar operation to that for Synthesis Example 2 except that monomers of the types and in proportions specified in Table 1 were used. Table 1 shows the Mw, the Mw/Mn and the proportion of each structural unit determined by the $^{13}$C-NMR analysis of the obtained each polymer.

TABLE 1

| | (1) Polymer component | Monomer type | Proportion of structural unit (% by mole) | Mw | Mw/Mn |
|---|---|---|---|---|---|
| Synthesis Example 1 | S-1 | M-1 | 52 | 7,000 | 2.10 |
| | | M-2 | 48 | | |
| Synthesis Example 2 | S-2 | M-1 | 50 | 6,000 | 1.90 |
| | | M-3 | 50 | | |
| Synthesis Example 3 | S-3 | M-3 | 50 | 8,500 | 1.50 |
| | | M-4 | 43 | | |
| | | M-5 | 7 | | |
| Synthesis Example 4 | S-4 | M-3 | 40 | 9,600 | 1.72 |
| | | M-5 | 12 | | |
| | | M-6 | 35 | | |
| | | M-7 | 13 | | |

* In Table, the proportion of the structural unit of M-3 indicates the proportion in terms of the p-hydroxystyrene structural unit obtained by deacetylation of the structural unit unit derived from M-3.

Synthesis Example 5

Synthesis of Compound (S-5)

10 g of glutaraldehyde (50% by mass aqueous solution), 24.8 g of 3-methoxyphenol and 37.5 g of trifluoroacetic acid were dissolved in 50 mL of chloroform, and the mixture was refluxed for 48 hrs. This solution was added to methanol, and the resulting precipitates were dried in vacuo to obtain 11.3 g of a single molecular compound (M-8) protected by a methoxy group as represented by the following formula. Next, 8.0 g of the compound (M-8), 8.2 g of potassium carbonate and 0.064 g of tetrabutylammonium bromide were dissolved in 95 mL of N-methylpyrrolidone (NMP), and the mixture was stirred at 60° C. for 3 hrs. A mixed solution of 4.3 g of 2-bromoacetyloxy-2-methyladamantane and 5 mL of NMP was added to this reaction mixture, and thus obtained reaction mixture was further stirred at 60° C. for 48 hrs. This reaction mixture was poured into chloroform, and washed with 0.1 M aqueous oxalic acid solution, followed by drying over magnesium sulfate. Filtration through Celite gave a filtrate, which was then concentrated in vacuo. Thus concentrated solution was added to methanol, thereby allowing the solid to be precipitated. The solid was dried under reduced pressure to obtain 5.9 g of a compound (S-5) in which 18% hydroxyl groups of the compound (M-8) were protected by a 2-acetyloxy-2-methyladamantane group. The compound (S-5) corresponds to the polymer component (1).

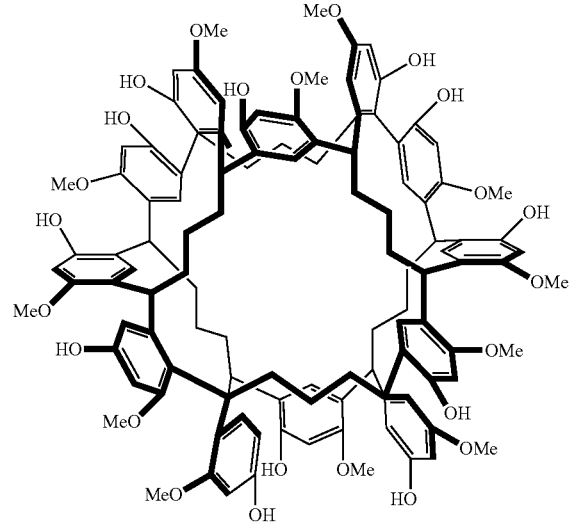

(M-8)

(2) Generative Component

Synthesis of Radiation-Sensitive Sensitizer Generating Agent (b)

Synthesis Example 6

Synthesis of Compound (B-1)

In 100 ml of toluene, 2.4 g of 4,4'-dimethoxy benzophenone, and 11.6 g of cis-1,2-cyclohexanediol were dissolved, and 0.1 g of p-toluenesulfonic acid was added thereto. The reaction was allowed for 48 hrs while the reaction mixture was refluxed at 130° C. and water produced as a by-product was eliminated by way of the Dean-Stark procedure. Subsequently, after the reaction mixture was concentrated in vacuo to remove toluene, column chromatography carried out using alumina gel gave a compound (B-1) represented by the following formula with a yield of 50%.

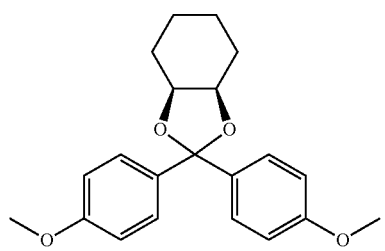

(B-1)

Synthesis Examples 7 to 11

Syntheses of Compounds (B-2) to (B-7)

Compounds (B-2) to (B-7) were synthesized by a similar operation to that for Synthesis Example 6 except that cis-1,2-cyclohexanediol was changed to alcohol compounds shown in Table 2.

TABLE 2

| | Alcohol compound | Synthesized compound | |
|---|---|---|---|
| | | Structure | Compound name |
| Synthesis Example 7 | HO, HO (racemic body) norbornane diol | | B2 |
| Synthesis Example 8 | HO-CH₂, HO- cyclopentane | | B-3 |
| Synthesis Example 9 | 2-nitroethanol | | B-4 |
| Synthesis Example 10 | 2-hydroxyethylmethylsulfone | | B-5 |
| Synthesis Example 11 | ethylene glycol | | B-6 |
| Synthesis Example 12 | dimethyl L-(+)-tartarate | | B-7 |

Synthesis Example 13

Synthesis of Compound b-8

A reaction solution was prepared by dissolving 2.4 g of 4,4'-dimethoxy benzophenone and 20 g of orthotrimethyl formate in 100 ml of nitromethane, and adding thereto 0.1 g of p-toluenesulfonic acid. The reaction was allowed at 100° C. for 12 hrs. Subsequently, after the reaction mixture was concentrated in vacuo to remove nitromethane, column chromatography carried out using alumina gel gave a compound (B-8) represented by the following formula with a yield of 72%.

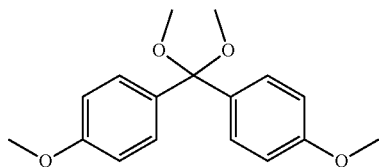

(B-8)

Absorbance Measurement of Radiation-Sensitive Sensitizer Generating Agent (b)

With respect to each of the radiation-sensitive sensitizer generating agent (b), and 4,4'-dimethoxy benzophenone as a sensitizing agent derived from the radiation-sensitive sensitizer generating agent (b), a 0.0001% by mass cyclohexane solution thereof was prepared. The absorbance of thus solution prepared was measured using cyclohexane as a reference solvent and a spectrophotometer ("V-670" available from JASCO Corporation).

At each wavelength falling within the range of no less than 250 nm and no greater than 600 nm, the absorbance was determined by subtracting the absorbance of the reference solvent from the absorbance of the solution to be measured. The measurement results of the absorbance were evaluated to be: "transparent" in a case where the measurement value of the absorbance was less than 0.01 over the entire wavelength range of no less than 250 nm and no greater than 450 nm; and "absorbing" in a case where the measurement value of the absorbance was no less than 0.01 at at least one wavelength within the entire wavelength range of no less than 250 nm and no greater than 450 nm. The results of the evaluations are shown in Table 3. It is to be noted that the transmittance of cyclohexane which was a solvent used for the measurement of the absorption spectrometry was ascertained to be no less than 95% at each wavelength falling within the range of no less than 250 nm and no greater than 600 nm.

TABLE 3

| Compound | Absorbance (250-450 nm) |
|---|---|
| B-1 | transparent |
| B-2 | transparent |
| B-3 | transparent |
| B-4 | transparent |
| B-5 | transparent |
| B-6 | transparent |
| B-7 | transparent |
| B-8 | transparent |
| 4,4'-dimethoxybenzophenone | absorbing |

(c) Radiation-Sensitive Acid Generating Agent

As the radiation-sensitive acid generating agent (c), a compound represented by the following formula (C-1) was used.

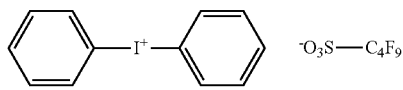

(C-1)

Preparation of Chemically Amplified Resist Material

Each component other than the polymer component (1) and the generative component (2), used for the preparation of the chemically amplified resist materials is shown below.

Acid Diffusion Control Agent

E-1: triphenylsulfonium salicylate (a compound represented by the following formula (E-1))

E-2: 2,4,5-triphenylimidazole (a compound represented by the following formula (E-2))

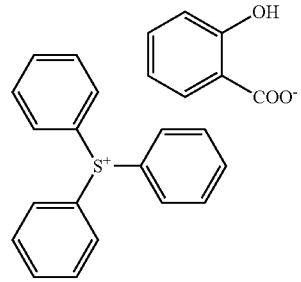

(E-1)

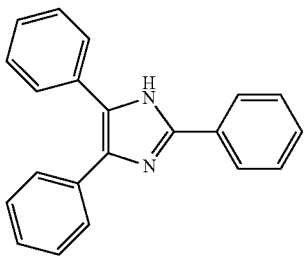

(E-2)

Solvent
G-1: propylene glycol monomethyl ether acetate
G-2: ethyl lactate
G-3: cyclohexanone

Example 1

Preparation of Chemically Amplified Resist Material (R-1)

100 parts by mass of (S-1) as the polymer component (1); 5 parts by mass of (B-1) as the radiation-sensitive sensitizer generating agent (b); 20 parts by mass of (C-1) as the radiation-sensitive acid generating agent (c); 2.5 parts by mass of (E-1) as the acid diffusion control agent; and 4,300 parts by mass of (G-1) and 1,900 parts by mass of (G-2) as the solvent were mixed. The mixture solution thus obtained was filtered through a membrane filter having a pore size of 0.20 μm to prepare a chemically amplified resist material (R-1).

Examples 2 to 5 and Comparative Examples 1 to 8

Preparation of Chemically Amplified Resist Materials (R-2) to (R-13)

Each chemically amplified resist material was prepared in a similar manner to Example 1 except that the type and the content of each component used were as shown in Table 4. Note that "–" in Table 4 indicates that the corresponding component was not added.

Operation (b): With Floodwise Exposure

After the irradiation with the electron beam, the entire face of the resist film was subjected to the floodwise exposure for 30 min using a black light lamp (Toshiba Corporation, wavelength: 320 nm). Subsequently, in the CLEAN TRACK ACT-8, PEB was carried out under conditions of 110° C. and 60 sec. Thereafter, development, washing and drying was carried out in a similar manner to that in the operation (a), whereby a positive resist pattern was formed.

TABLE 4

| | Chemically amplified resist material | (1) Polymer component | | (2) Generative component | | | | Acid diffusion control agent | | Solvent | |
|---|---|---|---|---|---|---|---|---|---|---|---|
| | | | | (b)component | | (c)component | | | | | |
| | | type | content (parts by mass) | type | content (parts by mass) | type | content (parts by mass) | type | content (parts by mass) | type | content (parts by mass) |
| Example 1 | R-1 | S-1 | 100 | B-1 | 5 | C-1 | 20 | E-1 | 5.0 | G-1/G-2 | 4,300/1,900 |
| Comparative Example 1 | R-2 | S-1 | 100 | — | — | C-1 | 20 | E-1 | 5.0 | G-1/G-2 | 4,300/1,900 |
| Example 2 | R-3 | S-2 | 100 | B-2 | 10 | C-1 | 20 | E-1 | 5.0 | G-1/G-2 | 4,300/1,900 |
| Comparative Example 2 | R-4 | S-2 | 100 | — | — | C-1 | 20 | E-1 | 5.0 | G-1/G-2 | 4,300/1,900 |
| Example 3 | R-5 | S-3 | 100 | B-3 | 10 | C-1 | 20 | E-1 | 7.5 | G-1 | 5,800 |
| Comparative Example 3 | R-6 | S-3 | 100 | — | — | C-1 | 20 | E-1 | 7.5 | G-1 | 5,800 |
| Example 4 | R-7 | S-4 | 100 | B-4 | 5 | C-1 | 20 | E-2 | 7.5 | G-1/G-3 | 5,000/1,000 |
| Comparative Example 4 | R-8 | S-4 | 100 | B-6 | 5 | C-1 | 20 | E-2 | 7.5 | G-1/G-3 | 5,000/1,000 |
| Comparative Example 5 | R-9 | S-4 | 100 | — | — | C-1 | 20 | E-2 | 7.5 | G-1 | 5,000/1,000 |
| Example 5 | R-10 | S-5 | 100 | B-5 | 10 | C-1 | 20 | E-2 | 5.0 | G-1 | 5,800 |
| Comparative Example 6 | R-11 | S-5 | 100 | B-7 | 10 | C-1 | 20 | E-2 | 5.0 | G-1 | 5,800 |
| Comparative Example 7 | R-12 | S-5 | 100 | B-8 | 10 | C-1 | 20 | E-2 | 5.0 | G-1 | 5,800 |
| Comparative Example 8 | R-13 | S-5 | 100 | — | — | C-1 | 20 | E-2 | 5.0 | G-1 | 5,800 |

Evaluations

The chemically amplified resist materials of Examples and Comparative Examples were evaluated for the sensitivity and the nanoedge roughness according to the following procedure through forming a resist pattern.

Formation of Resist Pattern

The chemically amplified resist material (R-1) of Example 1 was spin-coated onto a silicon wafer in "CLEAN TRACK ACT-8" available from Tokyo Electron Limited, and subjected to PB at 100° C. for 60 sec to form a resist film having an average thickness of 50 nm. Subsequently, the resist film was irradiated with an electron beam using a simplified electron beam writer ("HL800D" available from Hitachi, Ltd., power: 50 KeV, current density: 5.0 ampere/cm$^2$) to permit patterning. By using a mask, the patterning formed a line and space pattern (1L 1S) configured with a line part having a line width of 150 nm and a space part formed by neighboring line parts with an interval of 150 nm. After the irradiation with the electron beam for patterning, following operation (a) or (b) was carried out.

Operation (a): Without Floodwise Exposure

After the irradiation with the electron beam, PEB was carried out at 110° C. for 60 sec in the CLEAN TRACK ACT-8. Then, a development was carried out according to the puddle procedure at 23° C. for 1 min using a 2.38% by mass aqueous tetramethylammonium hydroxide (THAM) solution in the CLEAN TRACK ACT-8. Following the exposure, the substrate was washed with pure water, followed by drying, whereby a positive resist pattern was formed.

Sensitivity

An exposure dose at which a line and space pattern (1 L 1S) configured with a line part having a line width of 150 nm and a space part formed by neighboring line parts with an interval of 150 nm was formed to give a line width of 1:1 was defined as "optimal exposure dose", and the "optimal exposure dose" was used as a standard for the sensitivity. The sensitivity was evaluated to be: "A (favorable)" in the case of the optimal exposure dose being no less than 35 µC/cm$^2$; and "B (unfavorable)" in the case of greater than 35 µC/cm$^2$. Measured values of the optimal exposure dose and evaluation results of the sensitivity are shown in Table 5.

Nanoedge Roughness

Figure 2:
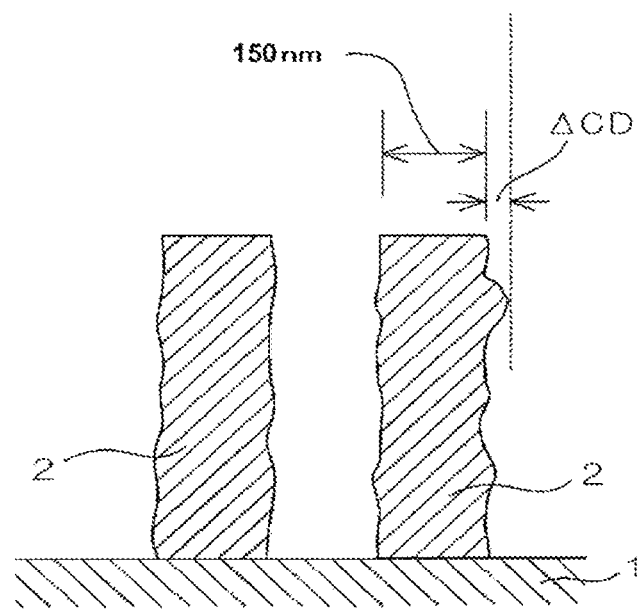
FIG. 2 shows a schematic cross sectional view illustrating the nanoedge roughness of the pattern.

The line patterns of the line and space pattern (1L 1S) were observed using a high-resolution FEB critical dimension measurement device (S-9220, available from Hitachi, Ltd.) at arbitrary twenty points on the line pattern. With respect to the points at which the observation was made, as shown in FIGS. 1 and 2, a difference "ΔCD" between an intended line width of 150 nm and a line width in an area in which irregularities generated along side lateral surface 2a of the line part 2 of the pattern formed on the substrate (silicon wafer) 1 was most significant was measured. The average value of the ΔCD of the twenty points was used as a standard for the nanoedge roughness. The nanoedge roughness was evaluated to be: "AA (extremely favorable)" in the case of the average value of ΔCD (nm) being no greater than 12.0 nm; "A (favorable)" in the case of greater than 12.0 nm and no greater than 14.0 nm; and "B (unfavorable)" in the case of greater than 14.0 nm. It is to be noted that the irregularities shown in FIGS. 1 and 2 are exaggerated. The average values of the ΔCD and evaluation results of the nanoedge roughness are shown in Table 5.

TABLE 5

| | Chemically amplified resist material | Evaluation results of operation (a) | | | | Evaluation results of operation (b) | | | |
|---|---|---|---|---|---|---|---|---|---|
| | | sensitivity | | nanoedge roughness | | sensitivity | | nanoedge roughness | |
| | | optimum exposure dose ($\mu$C/cm$^2$) | evaluation | average value of $\Delta$CD (nm) | evaluation | optimum exposure dose ($\mu$C/cm$^2$) | evaluation | average value of $\Delta$CD (nm) | evaluation |
| Example 1 | R-1 | 43.6 | B | 13.1 | A | 27.3 | A | 13.7 | A |
| Comparative Example 1 | R-2 | 42.6 | B | 13.4 | A | 41.4 | B | 13.5 | A |
| Example 2 | R-3 | 44.1 | B | 13.2 | A | 31.2 | A | 13.8 | A |
| Comparative Example 2 | R-4 | 43.2 | B | 13.3 | A | 42.0 | B | 13.6 | A |
| Example 3 | R-5 | 46.2 | B | 12.4 | A | 23.5 | A | 12.8 | A |
| Comparative Example 3 | R-6 | 45.2 | B | 12.2 | A | 42.3 | B | 12.7 | A |
| Example 4 | R-7 | 55.9 | B | 11.5 | AA | 25.3 | A | 11.9 | AA |
| Comparative Example 4 | R-8 | 57.2 | B | 11.7 | AA | 26.3 | A | 14.3 | B |
| Comparative Example 5 | R-9 | 58.2 | B | 11.4 | AA | 57.7 | B | 11.6 | AA |
| Example 5 | R-10 | 48.2 | B | 13.2 | A | 24.9 | A | 13.4 | A |
| Comparative Example 6 | R-11 | 47.6 | B | 13.2 | A | 36.2 | B | 13.5 | A |
| Comparative Example 7 | R-12 | 47.2 | B | 13.0 | A | 25.2 | A | 14.4 | B |
| Comparative Example 8 | R-13 | 46.2 | B | 13.5 | A | 46.2 | B | 13.6 | A |

As shown in Table 5, the chemically amplified resist materials of Examples were superior in the nanoedge roughness in both the operations (a) and (b), the operation (a) being a conventional pattern-forming method in which a patternwise exposure was carried out, and the operation (b) being a pattern-forming method in which a floodwise exposure was further carried out. In addition, the chemically amplified resist materials of Examples exhibited significantly improved sensitivity in the operation (b) than the sensitivity in the operation (a), clearly indicating that the chemically amplified resist materials of Examples can be suitably used for pattern-forming methods in which both the patternwise exposure and the floodwise exposure are carried out.

On the other hand, the chemically amplified resist materials of Comparative Examples not containing the radiation-sensitive sensitizer generating agent (b) exhibited comparative sensitivity in the operation (a) and nanoedge roughness to those of Examples; however, the sensitivity in the operation (b) was almost equivalent to that in the operation (a), failing to indicate any significant improvement of the sensitivity in the operation (b). In addition, the chemically amplified resist materials of Comparative Examples containing the radiation-sensitive sensitizer generating agent (b) which includes the acetal protecting group that fails to satisfy the requirement of the present invention exhibited a favorable sensitization effect per se in the operation (b); however, it was ascertained that the nanoedge roughness was deteriorated, or the sensitization effect in the operation (b) was limited.

As described in the foregoing, the chemically amplified resist material and the resist pattern-forming method of the embodiments of the present invention enable both sensitivity and lithography performances to be attained at a high level in a case where a radioactive ray having a wavelength of no greater than 250 nm such as EUV, an electron beam, an ion beam, a KrF excimer laser beam and an ArF excimer laser beam is used as patterning exposure light. Therefore, the chemically amplified resist material and resist pattern-forming method can be suitably used in photoresist processes in which further microfabrication is in progress hereafter.

Obviously, numerous modifications and variations of the present invention are possible in light of the above teachings. It is therefore to be understood that within the scope of the appended claims, the invention may be practiced otherwise than as specifically described herein.

The invention claimed is:

1. A chemically amplified resist material comprising:
   a polymer component that is capable of being made soluble or insoluble in a developer solution by an action of an acid; and
   a generative component that is capable of generating a radiation-sensitive sensitizer and an acid upon an exposure,
   wherein the generative component comprises:
   a radiation-sensitive acid-and-sensitizer generating agent and a radiation-sensitive sensitizer generating agent;
   the radiation-sensitive sensitizer generating agent and a radiation-sensitive acid generating agent; or
   all the radiation-sensitive acid-and-sensitizer generating agent, the radiation-sensitive sensitizer generating agent and the radiation-sensitive acid generating agent, wherein,
   the radiation-sensitive acid-and-sensitizer generating agent is capable of generating, upon an exposure to a first radioactive ray having a wavelength of no greater than 250 nm without an exposure to a second radioactive ray having a wavelength of greater than 250 nm, an acid and a radiation-sensitive sensitizer that absorbs the second radioactive ray, but the radiation-sensitive acid-and-sensitizer generating agent substantially does not generate the acid and the radiation-sensitive sensitizer upon an exposure to the second radioactive ray without an exposure to the first radioactive ray, the radiation-sensitive sensitizer generating agent is capable of generating, upon the exposure to the first radioactive ray without the exposure to the second radioactive ray, the radiation-sensitive sensitizer that absorbs the second radioactive ray, but the radiation-sensitive sensitizer generating agent substantially does not generate the radiation-sensitive sensitizer upon the exposure to the second radioactive ray without the exposure to the first radioactive ray, and
   the radiation-sensitive acid generating agent is capable of generating the acid upon the exposure to the first radioactive ray without the exposure to the second radioactive ray, but the radiation-sensitive acid generating agent substantially does not generate the acid upon the exposure to the second radioactive ray without the exposure to the first radioactive ray, and wherein the radiation-sensitive sensitizer generating agent comprises a compound represented by formula (B):

(B)

wherein, in the formula (B), $R^{B1}$ and $R^{B2}$ each independently represent a hydrogen atom, a halogen atom, an amino group or a monovalent organic group that comprises a carbon atom which bonds to the carbon atom to which $R^{B3}O$ and $R^{B4}O$ bond, or $R^{B1}$ and $R^{B2}$ taken together represent a cyclic structure having 3 to 30 ring atoms together with the carbon atom to which $R^{B1}$ and $R^{B2}$ bond; and $R^{B3}$ and $R^{B4}$ each independently represent a monovalent organic group having 1 to 20 carbon atoms, or taken together represent a cyclic structure having 4 to 30 ring atoms together with O—C—O to which $R^{B3}$ and $R^{B4}$ bond, wherein at least one of $R^{B3}$ and $R^{B4}$ comprises a halogen atom, a nitro group, a cyano group, a formyl group, a carboxy group, a sulfo group, or a combination thereof, or the cyclic structure having 4 to 30 ring atoms is a spiro cyclic structure, a fused cyclic structure or a bridged cyclic structure.

2. The chemically amplified resist material according to claim 1, wherein $R^{B1}$ and $R^{B2}$ in the formula (B) each independently represent: a hydrogen atom, a halogen atom, an amino group, a phenyl group, a naphthyl group, an anthracenyl group, an alkoxy group having 1 to 5 carbon atoms, an alkylthio group having 1 to 5 carbon atoms, a phenoxy group, a naphthoxy group, an anthracenoxy group, an amide group, an unsaturated hydrocarbon group having 1 to 30 carbon atoms, or a carbonyl group to which an alkyl group having 1 to 12 carbon atoms bonds; or a group obtained by substituting at least a part of hydrogen atoms included in the phenyl group, the naphthyl group, the anthracenyl group, the alkoxy group, the alkylthio group, the phenoxy group, the naphthoxy group, the anthracenoxy group or the unsaturated hydrocarbon group, and optionally, $R^{B1}$ and $R^{B2}$ bond to each other via a linking group, and $R^{B1}$ and $R^{B2}$ taken together represent a cyclic structure together with the carbon atom to which $R^{B1}$ and $R^{B2}$ bond and the linking group, wherein the linking group is a single bond, a double bond, or a bond comprising any one of —$CH_2$—, —O—, —S—, —$SO_2$—, —$SO_2NH$—, —C(=O)—, —C(=O)O—, —NHCO—, —NHC(=O)NH—, —$CHR^g$—, —$CR^g{}_2$—, —NH— and —$NR^g$—, wherein $R^g$ represents: a phenyl group; a phenoxy group; a halogen atom; a saturated or unsaturated linear, branched or cyclic hydrocarbon group having 1 to 30 carbon atoms; an alkoxy group having 1 to 5 carbon atoms, a hydroxy group or a phenoxy group substituted with an alkyl group having 1 to 5 carbon atoms; or a saturated or unsaturated linear, branched or cyclic hydrocarbon group having 1 to 30 carbon atoms, or a phenyl group substituted with an alkoxy group having 1 to 5 carbon atoms or a hydroxy group.

3. The chemically amplified resist material according to claim 1, wherein the compound represented by the formula (B) is represented by formula (B-I) or formula (B-II):

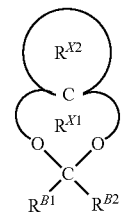

(B-I)

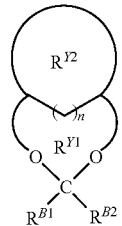

(B-II)

wherein, in the formulae (B-I) and (B-II), $R^{B1}$ and $R^{B2}$ are as defined in the formula (B), in the formula (B-I), $R^{x1}$ represents a group having a monocyclic structure having 4 to 20 ring atoms; and $R^{x2}$ represents a group having a cyclic structure having 3 to 20 ring atoms, and in the formula (B-II), $R^{Y1}$ represents a group having a monocyclic structure having 5 to 20 ring atoms; $R^{Y2}$ represents a group having a cyclic structure having 3 to 20 ring atoms; and n is an integer of 0 to 3.

4. The chemically amplified resist material according to claim 1, wherein the polymer component comprises a first polymer comprising a structural unit which comprises a group that is capable of generating a polar group upon dissociation of an acid-labile group by an action of an acid.

5. The chemically amplified resist material according to claim 4, wherein the first polymer comprises a structural unit that comprises a fluorine atom, or the polymer component comprises a second polymer that is different from the first polymer, the second polymer having a structural unit that comprises a fluorine atom.

6. The chemically amplified resist material according to claim 1, wherein the generative component is different from the polymer component.

7. The chemically amplified resist material according to claim 6, wherein a content of the generative component with respect to a total solid content is no less than 5% by mass and no greater than 40% by mass.

8. The chemically amplified resist material according to claim 1, wherein $R^{B1}$ and $R^{B2}$ each independently represent a phenyl group substituted with an alkoxy group having 1 to 5 carbon atoms or with an alkyl group having 1 to 5 carbon atoms.

9. The chemically amplified resist material according to claim 1, wherein $R^{B1}$ and $R^{B2}$ each independently represent a phenyl group substituted with an alkoxy group having 1 to 3 carbon atoms.

10. The chemically amplified resist material according to claim 1, wherein $R^{B1}$ and $R^{B2}$ each represent a phenyl group substituted with a methoxy group.

11. The chemically amplified resist material according to claim 1, wherein $R^{B1}$ and $R^{B2}$ are identical.

12. The chemically amplified resist material according to claim 1, wherein $R^{B1}$—C—$R^{B2}$ in formula (B) forms a partial structure represented by one of formulae (XXVII) to (XXX):

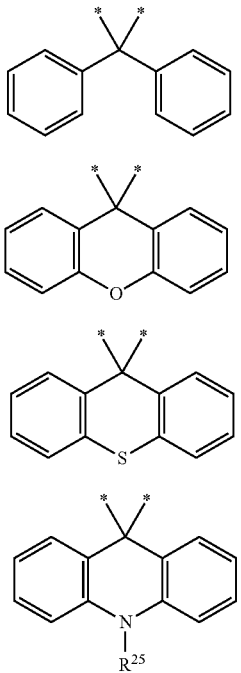

(XXVII)

(XXVIII)

(XXIX)

(XXX)

wherein in the formulae (XXVII) to (XXX), * denotes a site of binding to $OR^{B3}$ or $OR^{B4}$, $R^{25}$ represents an alkyl group having 1 to 5 carbon atoms, and one or more hydrogen atoms of the aromatic ring in the formulae (XXVII) to (XXX) may be substituted with an alkoxy group having 1 to 5 carbon atoms or an alkyl group having 1 to 5 carbon atoms, and the aromatic ring in the formulae (XXVII) to (XXX) may bind to another aromatic ring to form a naphthalene ring or an anthracene ring.

13. The chemically amplified resist material according to claim 12, wherein the partial structure is represented by formula (XXVII).

14. The chemically amplified resist material according to claim 12, wherein the partial structure is represented by

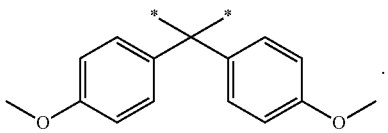

15. The chemically amplified resist material according to claim 1, wherein $R^{B3}$ and $R^{B4}$ are identical.

16. The chemically amplified resist material according to claim 1, wherein at least one of $R^{B3}$ and $R^{B4}$ comprises a nitro group.

17. The chemically amplified resist material according to claim 1, wherein an amount of the compound represented by formula (B) is at least 60 mol % with respect to a total amount of the radiation-sensitive sensitizer generating agent.

18. The chemically amplified resist material according to claim 1, wherein an amount of the compound represented by formula (B) is at least 70 mol % with respect to a total amount of the radiation-sensitive sensitizer generating agent.

19. The chemically amplified resist material according to claim 1, wherein an amount of the compound represented by formula (B) is 100 mol % with respect to a total amount of the radiation-sensitive sensitizer generating agent.

20. A resist pattern-forming method comprising:
applying the chemically amplified resist material according to claim 1 on at least one face of a substrate to form a resist film;
patternwise exposing the resist film to a radioactive ray having a wavelength of no greater than 250 nm;
floodwise exposing to a radioactive ray having a wavelength of greater than 250 nm, the resist film patternwise exposed;
baking the resist film floodwise exposed; and
developing with a developer solution, the resist material film baked.

* * * * *